United States Patent [19]
Dean

[11] Patent Number: 5,641,487
[45] Date of Patent: Jun. 24, 1997

[54] CONTRACEPTIVE VACCINE BASED ON ALLOIMMUNIZATION WITH ZONA PELLUCIDA POLYPEPTIDES

[75] Inventor: Jurrien Dean, Bethesda, Md.

[73] Assignee: The Government of the United States of America as represented by the Secretary Department of Health and Human Services, Washington, D.C.

[21] Appl. No.: 38,948

[22] Filed: Mar. 26, 1993

Related U.S. Application Data

[63] Continuation-in-part of Ser. No. 930,462, Aug. 20, 1992, abandoned, which is a continuation of Ser. No. 364,379, Jun. 12, 1989, abandoned.

[51] Int. Cl.⁶ .......................... A61K 39/00; A61K 38/00; C12P 21/04; C07K 2/00
[52] U.S. Cl. ................ 424/184.1; 435/69.3; 530/300; 530/326; 514/2; 514/13; 514/14; 514/21
[58] Field of Search ................. 424/184.1; 435/69.3; 530/300, 326; 514/2, 13, 14, 21

[56] References Cited

U.S. PATENT DOCUMENTS

| | | | |
|---|---|---|---|
| 3,992,520 | 11/1976 | Gwatkin | 424/85 |
| 4,795,634 | 1/1989 | Grimes | 424/85.9 |
| 4,996,297 | 2/1991 | Dunbar | 530/395 |

OTHER PUBLICATIONS

Alexander et al. (Ed). 1990. Gamete Interaction: Prospects for Immunocontracephon. pp. 313–326. Wiley–Liss.
Schwoebel et al. 1992. Biol. of Reprod. 47:857–65.
Yurewicz et al. 1986. Adv. Exptal Med & Biol 207:407–27.
Tung et al. 1999. FASEB J. 5(5):A1088.
Ragliupathy. et al. 1992. Current Opin. Immunol. 4:597–602.
Marx 1978. Contraception: An Antipregnancy Vaccine. Science 200:1258.
Sacco, 1987, Zona Pellucida: Current Status as a Candidate Antigen . . . AJRIM. 15:122–130.
Kinloch et al. 1988. Primary Structure of the Mouse Sperm . . . PNAS. 85:6409–6413.
Henderson et al. 1988. Contraceptive Potential of Antibodies to the Zona Pellucida. J. Reprod. Fert. 83:325–343.
Ringuette et al. 1988 Molecular Analysis of cDNA Coding for ZP3 . . . Developmental. Biol. 127:287–95.
Carella v. Starlight Archery, 231 USPQ 644, 646 (1986).
Li–Fang Liang and Jurrien Dean, Conservation of Mammalian Secondary Sperm Receptor Genes Enables the Promoter of the Human Gene to Function in Mouse Oocytes, Developmental Biology 156, 1993, pp. 399–408.
Jurrien Dean, Biology of Mammalian Fertilization: Role of the Zona Pellucida, The Journal of Clinical Investigation, Inc., vol. 89, Apr. 1992, pp. 1055–1059.
Stephen J. Beebe et al., Recombinant Mouse ZP3 Inhibits Sperm Binding and Induces the Acrosome Reaction, Developmental Biology 151, 1992, pp. 48–54.

Sung Hee Rhim et al., Autoimmune Disease of the Ovary Induced by a ZP3 Peptide from the Mouse Zona Pellucida, The American Society for Clinical Investigation, Inc. vol. 89, Jan. 1992, pp. 28–35.
Li–Fang Liang et al., Oocyte–Specific Expression of Mouse Zp–2: Developmental Regulation of the Zone Pellucida Genes, Molecular and Cellular Biology, Apr. 1990, pp. 1507–1515.
R. Dwayne Lunsford et al., Genomic Mapping of Murine Zp–2 and Zp–3, Two Oocyte–Specific Loci Encoding Zona Pellucida Proteins, Genomics 6, 1990, pp. 184–187.
Margaret E, Chamberlin and Jurrien Dean, Human homolog of the mouse sperm receptor, Proc. Natl. Acad. Sci. USA, vol. 87, Aug. 1990, pp. 6014–6018.
Sarah E. Millar et al., Vaccination with a Synthetic Zona Pellucida Peptide Produces Long–Term Contraception in Female Mice, Science, vol. 246, 17 Nov. 1989, pp. 935–938.
Margaret E. Chamberlin and Jurrien Dean, Genomic Organization of a Sex Specific Gene: The Primary Sperm Receptor of the Mouse Zona Pellucide, Developmental Biology 131, 1989, pp. 207–214.
Maurice J. Ringuette et al., Molecular Analysis of cDNA Coding for ZP3, a Sperm Binding Protein of the Mouse Zona Pellucida, Developmental Biology 127, 1988, 287–295.
Caroline C. Philpott et al., Oocyte–Specific Expression and Developmental Regulation of ZP3, the Sperm Receptor of the Mouse Zona Pellucida, Developmental Biology 121, 1987, pp. 568–575.
Maurice J. Ringuette et al., Oocyte–specific gene expression: Molecular characterization of a cDNA coding for ZP–3 the sperm receptor of the mouse zona pellucida, Proc. Natl. Acad. Sci. USA, vol. 83, Jun. 1986, pp. 4341–4345.

(List continued on next page.)

*Primary Examiner*—James C. Housel
*Assistant Examiner*—N. M. Minnifield
*Attorney, Agent, or Firm*—Morgan & Finnegan, L.L.P.

[57] ABSTRACT

The present invention relates to contraceptive vaccines based on cloned zona pellucida genes and the strategy of alloimmunization with zona pellucida polypeptides. In particular, the present invention relates to a contraceptive vaccine for use in a mammalian female comprising a polypeptide which displays at least one epitope for binding of an antibody that inhibits fertilization of an oocyte by a sperm. This epitope is from a zona pellucida protein of the species in which the said vaccine is used. This invention relates, more particularly, to such vaccines wherein the zona pellucida protein is the ZP3 protein or the mouse or homologues of the protein in some other mammalian species. Further, this invention comprehends vaccines comprising a synthetic peptide that displays an epitope for such an antibody that inhibits fertilization. In addition, this invention relates to cloned DNA segments variously encoding the mouse ZP3 protein or the human ZP3 protein.

6 Claims, 15 Drawing Sheets

OTHER PUBLICATIONS

Iain J. East et al., Monoclonal Antibodies to the Murine Zona Pellucida Protein with Sperm Receptor Activity: Effects on Fertilization and Early Developmental Biology 109, 1985, pp. 268–273.

Iain J. East et al., Scintigraphu of Normal Mouse Ovaries with Monoclonal Antibodies to ZP–2, the Major Zona Pellucida Protein, Science, vol. 225, 31 Aug. 1984, pp. 938–941.

Iain J. East et al., Monoclonal Antibodies to the Major Protein of the Murine Zona Pellucida: Effects on Fertilization and Early Development, Developmental Biology 104, 1984, pp. 49–56.

Iain J. East and Jurrien Dean, Monoclonal Antibodies as Probes of the Distribution of ZP–2, the Major Sulfated Glycoprotein of the Murine Zona Pellucida, The Journal of Cell Biology, vol. 98, Mar. 1984, pp. 795–800.

Satoru Shimizu et al., In Vitro Biosynthesis of Three Sulfated Glycoproteins of Murine Zonae Pellucidae by Oocytes Grown in Follicle Culture, Journal of Biologial Chemistry, vol. 258 No. 9, May. 10, 1983, pp. 5858–5863.

```
5' CT GAG CCC AGC TGT ACT CCA GGC GGG ACC ATG GCG TCA AGC TAT TTC CTT TGT GTC CTC CTG TGT GGA GGC CCC GAG CTG TGC
                                         30                60
                                         Met Ala Ser Ser Tyr Phe Leu Cys Val Leu Leu Cys Gly Gly Pro Glu Leu Cys

AAT TCC CAG ACT CTG TGG CCT CTT TTG CCG GGT GGA ACT CCC ACC CCA GTG GGG TCC TCA CCT GTG AAG GTG GAG TGT CTG GAA GCT GAA
                   120                              150
Asn Ser Gln Thr Leu Trp Pro Leu Leu Pro Gly Gly Thr Pro Thr Pro Val Gly Ser Ser Pro Val Lys Val Glu Cys Leu Glu Ala Glu

CTA GTG GTG ACT GTC AGT AGA GAC CTT TTT GGC ACG GGG AAG CTG GTG CAG CCC GAC CTC ACC CTT GGC TCA GAG GGT TGT CAG CCC
                   210                              240
Leu Val Val Thr Val Ser Arg Asp Leu Phe Gly Thr Gly Lys Leu Val Gln Pro Asp Leu Thr Leu Gly Ser Glu Gly Cys Gln Pro

CGG GTG TCC TTG GAT ACC AGG TTC AAC GCC GTG CAG TTG CAC GAG TGC AGC AGG GTG CAG ATG ACG AAA GAT GCC CTG GTG
              300
Arg Val Ser Leu Asp Thr Arg Phe Asn Ala Val Gln Leu His Glu Cys Ser Arg Val Gln Met Thr Lys Asp Ala Leu Val
                   330                              390

TAC AGC ACC TTC CTA CTC CAC GAC CCT GTG AGT GGC CCT CGC ATC CTC AGG ACT AAC CGT GTG GAG GTA CCC ATT GAG TGC CGA
                                         420
Tyr Ser Thr Phe Leu Leu His Asp Pro Val Ser Gly Pro Arg Ile Leu Arg Thr Asn Arg Val Glu Val Pro Ile Glu Cys Arg

TAC CCC AGG CAG GGC AAT GTG AGC AGC CCT ATC CAG CCC ACC TGG GTT CCC TTC AGA GCC ACT GTG TCC TCA GAG GAG AAA CTG GCT
                   480                              510
Tyr Pro Arg Gln Gly Asn Val Ser Ser Pro Ile Gln Pro Thr Trp Val Pro Phe Arg Ala Thr Val Ser Ser Glu Glu Lys Leu Ala

TTC TCT CTT CGC CTG ATG GAG GAG AAC ACT GAG AAA TCG GCT CCC ACC TTC CAC CTG GGA GAG GTA GCC CAC CTC CAG GCA GAA
                   570                              600
Phe Ser Leu Arg Leu Met Glu Glu Asn Thr Glu Lys Ser Ala Pro Thr Phe His Leu Gly Glu Val Ala His Leu Gln Ala Glu

GTC CAG ACT GGA AGC CAC CTG CAG TTT GTG GAC CAC TGC GTG ACG CCT TCA CCT TTG CCA GAC CCG AAC TCC CCC
                   660                              690
Val Gln Thr Gly Ser His Leu Gln Phe Val Asp His Cys Val Ala Thr Pro Ser Pro Leu Pro Asp Pro Asn Ser Pro
```

FIG. 1A

```
TAT GAC TTC ATC GTG GAC TTC CAC GGT TGC CTT GTG GAT GGT CTA TCT GAG AGC TTT CAA GTC CCC AGA CCC CGG CCA GAG
Tyr Asp Phe Ile Val Asp Phe His Gly Cys Leu Val Asp Gly Leu Ser Glu Ser Phe Gln Val Pro Arg Pro Arg Pro Glu
                                        750                           780
ACT CTC CAG TTC ACG GTG GAT GTA TTC CAT TTT GCC AGA AAT ACG CTC TAC ATC ACC TGC CAT CTC AAA GTC GCG CCA GCT
Thr Leu Gln Phe Thr Val Asp Val Phe His Phe Ala Arg Asn Thr Leu Tyr Ile Thr Cys His Leu Lys Val Ala Pro Ala
                          840                            870
AAC CAG ATC CCC GAT AAG AAA CTC AAC AAG ACT TCC GAG AGT TGG CCA GTA GAG GGT GAT GCT GAC ATC TGT
Asn Gln Ile Pro Asp Lys Lys Leu Asn Lys Thr Ser Phe Asn Lys Thr Ser Gln Ser Trp Pro Val Glu Gly Asp Ala Asp Ile Cys
                                          930                        960
GAT TGC TGC AGC CAT GGC AAC TGT AGT AAT TCA AGC TCT TCA CAG TTC CAG ATC CAT GGA CCC CGG CAG TGG TCC AAG GTT TCT CGA
Asp Cys Cys Ser His Gly Asn Cys Ser Asn Ser Ser Ser Ser Gln Phe Gln Ile His Gly Pro Arg Gln Trp Ser Lys Val Ser Arg
                                              1020                             1050
AAC CGC AGG CAC GTG ACC GAT GAA GCT GTG ACT GAT ATA TTC CTT GGA AAG GCC AAC GAG CAG ACT GTG GAA GGC TGG
Asn Arg Arg His Val Thr Asp Glu Ala Val Thr Asp Ile Phe Leu Gly Lys Ala Asn Asp Gln Thr Val Glu Gly Trp
                      1110                             1140
ACT GCT TCT CAA ACC TCT GTG GCT CTT GGG TTA GGC CTG GCA TTC GGA CTG GCA GCT ATA GTC CTT GCT GTC ACC
Thr Ala Ser Gln Thr Ser Val Ala Leu Gly Leu Gly Leu Ala Phe Gly Leu Ala Ala Ile Val Leu Ala Val Thr
                 1200                                 1230
AGG AAG TGT CAC TCC TCT TCC TAC CTT GTA TCC CTT CCG CAA TAA AAG AAG AAA CTC A 3'
Arg Lys Cys His Ser Ser Ser Tyr Leu Val Ser Leu Pro Gln
                         1290
```

```
CAC CTC GGC GCT TTG GTG GTA CCT TCC AAC ATG GCG AGG TGG CAG AGG AAA GCA TCT GTA AGC TCT CCG TGC GGC AGG AGC ATC TAC AGG     90
                                    Met Ala Arg Trp Gln Arg Lys Ala Ser Val Ser Ser Pro Cys Gly Arg Ser Ile Tyr Arg

TTT CTT TCC CTC TTA TTC ACC CTT GTG ACT TCA GTG AAC TCA GTA AGC CTT CCT CAG TCC GAG AAT CCT GCC TTC CGA GGC ACT CTC ATT    180
Phe Leu Ser Leu Leu Phe Thr Leu Val Thr Ser Val Asn Ser Val Ser Leu Pro Gln Ser Glu Asn Pro Ala Phe Arg Gly Thr Leu Ile

TGT GAC AAA GAC GAA GTG AGA ATT GAA TTT GAC ATG GAA AAA TGG TCA AAT CCT TCT GTG GTG GAT ACC CTT GGT AGT GAA    270
Cys Asp Lys Asp Glu Val Arg Ile Glu Phe Asp Met Glu Lys Trp Ser Asn Pro Ser Val Val Asp Thr Leu Gly Ser Glu

ATT TTG AAC TGC ACT TAT GCT CTG GAC TTG GAA AGG TTC GTC CTG AAG TTC CCT TAC CTG ACC GAG ACC TGC ACT ATA AAA GTG GTT GGA TAC    360
Ile Leu Asn Cys Thr Tyr Ala Leu Asp Leu Glu Arg Phe Val Leu Lys Phe Pro Tyr Glu Thr Cys Thr Ile Lys Val Val Gly Tyr

CAG GTG AAC ATC AGA GTG GGG GAC ACC ACT GAT GAC ATG AGA TAT CTA TCT TTC TGT CCA GCT ATT CAA GCA GAG    450
Gln Val Asn Ile Arg Val Gly Asp Thr Thr Asp Val Arg Tyr Lys Asp Met Tyr His Phe Cys Pro Ala Ile Gln Ala Glu

ACC CAT GAG ATT TCA GAA ATT GTC TGC AGG AGA GAT CTA ATC TCT TTC CCA CAA CTT TTC CTG CTG GAT GAA AAC    540
Thr His Glu Ile Ser Glu Ile Val Cys Arg Arg Asp Leu Ile Ser Phe Pro Gln Leu Phe Ser Arg Leu Ala Asp Glu Asn

CAG AAT GTA TCT GAG ATG TGG GGA ATT GTT AAG GTT CTG CCC TTG AAG GAT GCC CAC ATT CTG CCC TTG AAG GAT GCA ATA GTA CAA GGA    630
Gln Asn Val Ser Glu Met Trp Gly Ile Val Lys Val Leu Pro Leu Lys Asp Ala His Ile Leu Pro Leu Lys Asp Ala Ile Val Gln Gly

TTT AAT CTT GAT TAC AGC CAG CTC CAC GTC CCA GCC AAT GCT ACT GGA ATA GTT CAC TAT GTG CAA GAG AGC AGC TAT    720
Phe Asn Leu Asp Tyr Ser Gln Leu His Val Pro Ala Asn Ala Thr Gly Ile Val His Tyr Val Gln Glu Ser Ser Tyr

CTC TAT ACT GTG CAG CTG ATT GAC CTC TTG TTC TCA ACC ACT GGG CAG AAG ATC GTC TTC TCA CAC GCT ATC TGC GCA CCA GAT CTT TCT    810
Leu Tyr Thr Val Gln Leu Ile Asp Leu Leu Phe Ser Thr Thr Gly Gln Lys Ile Val Phe Ser His Ala Ile Cys Ala Pro Asp Leu Ser
```

FIG. 3A

```
                                  840                                          870                                          900
GTG GCT TGT AAT GCT ACA CAC ATG ACT CTC ACT ATA CCA GAA TTT CCT GGG AAG CTA GAG GTG TCT GTG GAC TTT GGA CAA TGG AGC ATC CCT
Val Ala Cys Asn Ala Thr His Met Thr Leu Thr Ile Pro Glu Phe Pro Gly Lys Leu Glu Val Ser Val Asp Phe Gly Gln Trp Ser Ile Pro
                                  930                                          960                                          990
GAG GAC CAA TGG CAT GCC AAT GGA GAA ACA AAT GAC TTG AGA TTG AAT GGC TTG AGA TTC AGA AAA TCT CTC CTG AAA ACT AAA CCC
Glu Asp Gln Trp His Ala Asn Gly Glu Thr Asn Asp Leu Arg Leu Asn Gly Leu Arg Phe Arg Lys Ser Leu Leu Lys Thr Lys Pro
                                  1020                                         1050                                         1080
TCT GAA AAA TGT CCA TTC TAC CAG TTC TCT CTC AAG CTG ACC TTC TAC TTC CAA GGG AAC ATG CTA TCC ACA GTG ATA GAT
Ser Glu Lys Cys Pro Phe Tyr Gln Phe Ser Leu Lys Leu Thr Phe Tyr Phe Gln Gly Asn Met Leu Ser Thr Val Ile Asp
                                  1110                                         1140                                         1170
CCT GAG TGC CAC TGT GAG TCA CCA GTC TCT ATA GAT GAA GAG CTG TGT GCA CAG GAT GGG TTT ATG GAC TTT GAG GTC TAC AGC CAC CAA ACA
Pro Glu Cys His Cys Glu Ser Pro Val Ser Ile Asp Glu Glu Leu Cys Ala Gln Asp Gly Phe Met Asp Phe Glu Val Tyr Ser His Gln Thr
                                  1200                                         1230                                         1260
AAA CCC GGA CTG AAC CTG GAC ACC CTC GTG CTG GGA AAT TCC TCT TGC CAG CCT ATT TTC AAG GTG CAG TCT GTG GGG CTT GCA AGG TTT
Lys Pro Gly Leu Asn Leu Asp Thr Leu Val Leu Gly Asn Ser Ser Cys Gln Pro Ile Phe Lys Val Gln Ser Val Gly Leu Ala Arg Phe
                                  1290                                         1320                                         1350
CAC ATA CCT CTG AAT GGA TGT GGA ACA AGG CAG AAA TTT GAA GGT GAT AAA GTC ATC TAT GAG AAT GAA ATA CAT GCT CTC TGG GAA AAC
His Ile Pro Leu Asn Gly Cys Gly Thr Arg Gln Lys Phe Glu Gly Asp Lys Val Ile Tyr Glu Asn Glu Ile His Ala Leu Trp Glu Asn
                                  1380                                         1410                                         1440
CCA TCC AAC ATT GTA TTC AGA AAC AGC GAG ATG ACA GTA TTC TAC ATC AGA GAC AGT ATG CTA AAT GCC CAT
Pro Ser Asn Ile Val Phe Arg Asn Ser Glu Met Thr Val Arg Cys Tyr Tyr Ile Arg Asp Ser Met Leu Asn Ala His
                                  1470                                         1500                                         1530
GTC AAA GGA CAT CCT TCT CCA GAG GCC TTT GTA TTC CTA AAG CTG GTG CTG GTG CCA GAG CAA TCC TAC CAA CGG
Val Lys Gly His Pro Ser Pro Glu Ala Phe Val Phe Leu Lys Leu Val Leu Val Pro Asp Ser Tyr Gln Arg
                                  1560                                         1590                                         1620
CCT TAC AGG AAG GAT GAG TAC CTC CTA GTG TAC AGG TAC CTG GTC CCA ATC TAC CGC CAG CCA GTG AAG GTC TTG AGC AGG AAC GAT CCC AAC
Pro Tyr Arg Lys Asp Glu Tyr Leu Leu Val Arg Tyr Leu Val Pro Ile Tyr Arg Gln Pro Val Lys Val Leu Ser Arg Asn Asp Pro Asn
```

FIG. 3B

```
ATC AAG CTG GTC TTA GAT GAC TGC TGG GCA ACT TCT TCT GAG GAC CCG GCC TCT GCG CCT CAG TGG CAG ATT GTC ATG GAT GGC TGT GAA
Ile Lys Leu Val Leu Asp Asp Cys Trp Ala Thr Ser Ser Glu Asp Pro Ala Ser Ala Pro Gln Trp Gln Ile Val Met Asp Gly Cys Glu
                                        1650                            1680                                        1710

TAT GAA CTG GAC AAC TAC CGC ACT ACT TTC CAC CCA GCT TTC TCT GCA GCC CAT TCC GGT CAC TAC CAG AGG TTT GAT GTG AAG ACT
Tyr Glu Leu Asp Asn Tyr Arg Thr Thr Phe His Pro Ala Phe Ser Ala Ala His Ser Gly His Tyr Gln Arg Phe Asp Val Lys Thr
                    1740                            1770                            1800

TTT GCC TTT GTA TCA GAG GCA CGG TCC CTC AGC CTG ATC TAC TTC CAC TGC AGT GCC TTG ATC AAC CAA GTC TCT CTT GAC TCC
Phe Ala Phe Val Ser Glu Ala Arg Ser Leu Ser Leu Ile Tyr Phe His Cys Ser Ala Leu Ile Asn Gln Val Ser Leu Asp Ser
                1830                            1860                            1890

CCT CTG TGC TCT GTG ACT TGC CCT GCA TCA CTG AGG AGC AAA CGA GAG GCC AAC AGA GAC ACA ATG ACG GTT AGC CTT CCA GGA CCT
Pro Leu Cys Ser Val Thr Cys Pro Ala Ser Leu Arg Ser Lys Arg Glu Ala Asn Arg Asp Thr Met Thr Val Ser Leu Pro Gly Pro
            1920                            1950                            1980

ATT CTC TTG CTG TCA GAT GTC TCT TCA AAA GGT GTT GAC CCC AGC AGC TCT GAG ATT ATT ACC AAG GAT ATT GCC AAG GAT ATT GCT
Ile Leu Leu Leu Ser Asp Val Ser Ser Lys Gly Val Asp Pro Ser Ser Ser Glu Ile Thr Lys Asp Ile Ala Lys Asp Ile Ala
        2010                            2040                            2070

TCT AAA ACA CTG GCT GCT GTG GCA CTA GTG GGC TCA GCT GTC ATT CTA GGC TTC ATC TGT TAC CTG TAT AAG AAA AGA ACT ATA AGG
Ser Lys Thr Leu Ala Ala Val Ala Leu Val Gly Ser Ala Val Ile Leu Gly Phe Ile Cys Tyr Leu Tyr Lys Lys Arg Thr Ile Arg
    2100                            2130                            2160

TTC AAT CAC TGA TTG GAC TTG CAA ATA AAG AGA CTG CAG TC
Phe Asn His
            2190
```

Amino Acid Residue

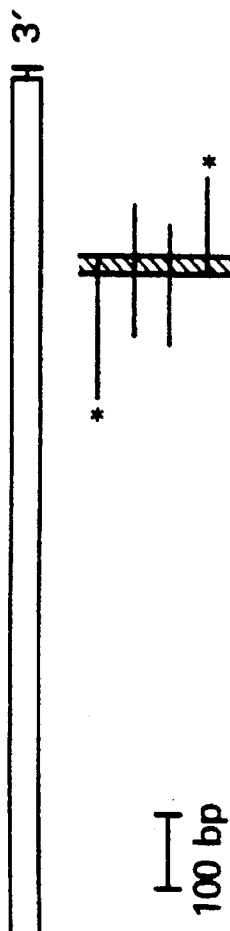
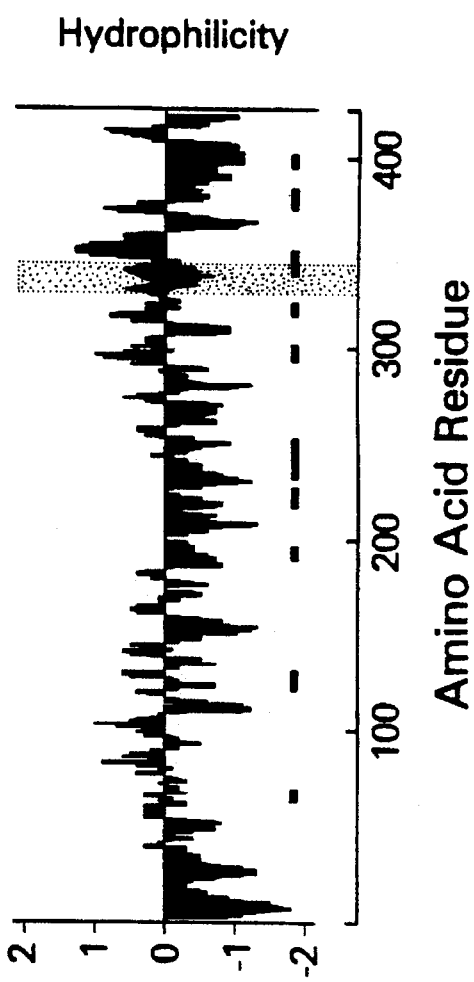
FIG. 7A
FIG. 7B
FIG. 7C

```
                    328                                                              343
Mouse    NH2-Cys-Ser-Asn-Ser-Ser-Ser-Ser-Ser-Gln-Phe-Gln-Ile-His-Gly-Pro-Arg-Gln-COOH
Human    NH2-Cys-Gly-Thr-Pro-Ser-His-Ser-Arg-Arg-Gln-Pro-His-Val-Met-Ser-Gln-COOH
                    327                                                         342
```

FIG. 9A

```
                114                                                 129
Mouse    NH2-Ile-Arg-Val-Gly-Asp-Thr-Thr-Thr-Asp-Val-Arg-Tyr-Lys-Asp-Asp-Met-COOH
Human    NH2-Ile-Arg-Val-Met-Asn-Asn-Ser-Ala-Ala-Leu-Arg-His-Gly-Ala-Val-Met-COOH
                118                                                 133
```

FIG. 9B

CONTRACEPTIVE VACCINE BASED ON ALLOIMMUNIZATION WITH ZONA PELLUCIDA POLYPEPTIDES

The subject application is a Continuation-In-Part of U.S. patent application Ser. No. 07/930,462, filed on Aug. 20, 1992, now abandoned and hereby incorporated in its entirety by reference. U.S. patent application Ser. No. 07/930,462 is a continuation of U.S. patent application Ser. No. 07/364,379, filed on Jun. 12, 1989 and now abandoned.

BACKGROUND OF THE INVENTION

1. Technical Field

The present invention relates to contraceptive vaccines based on cloned zona pellucida genes and the strategy of alloimmunization with zona pellucida polypeptides. In particular, the present invention relates to a contraceptive vaccine for use in a mammalian female comprising a polypeptide which displays at least one epitope for binding of an antibody that inhibits fertilization of an oocyte by a sperm. This epitope is from a zona pellucida protein of the species in which the said vaccine is used.

This invention relates, more particularly, to such vaccines wherein the zona pellucida protein is either the mouse ZP2 protein, the mouse ZP3 protein, the human ZP2, the human ZP3 protein, or homologues of these proteins found in other mammalian species. Further, this invention includes vaccines comprising a synthetic peptide that displays an epitope for such an antibody that inhibits fertilization. In addition, this invention relates to cloned DNA segments variously encoding the mouse ZP3 or ZP2 proteins, or the human ZP2 or ZP3 proteins.

2. Background Information

There is currently much interest in the development of a safe and effective contraceptive vaccine for control of diverse mammalian populations. Contraceptive vaccines would be useful under certain circumstances where relatively long-term but not permanent contraception is desired without the need for frequent intervention, for example, in pets including cats and dogs, in agriculturally important livestock such as cattle and pigs, and in human beings. A contraceptive vaccine preferably should have an effect which is long-lasting and highly specific. Further, to minimize possibilities for birth defects in the event of failed contraception, the antigen which is selected as the immunogen should produce contraceptive antibodies that inhibit fertilization of the egg by a sperm rather than by an abortifacient mechanism involving disruption of early development. In addition, the vaccine preferably should induce an immunological response that is sufficient to be effective for contraception without eliciting a cytotoxic response that might result in abnormal reproductive function.

The mammalian zona pellucida, which surrounds growing oocytes and ovulated eggs, has been recognized as a potential immunogen for a contraceptive vaccine (C. J. Henderson, et al., *J. Reprod. Fert.* 83:325–343 (1988); B. S. Dunbar, 1983, Mechanisms and Control of Animal Fertilization, J. F. Hartmann, ed., pp. 140–175, Academic Press, New York; A. T. Sacco, *Am. J. Reprod. Immunol. Microbiol.* 15:122 (1987); Millar et al., Targeting of zona pellucida for immunocontraception, in *Immunology of Reproduction*, Naz, R. K. (ed.), pp. 293–313 (1993)). At birth the mouse ovary contains 10,000–15,000 oocytes in the prophase of the first meiotic division. As cohorts (10–15) of these oocytes enter into a two week growth phase, they synthesize and secrete zona proteins to form the extracellular zona pellucida which ultimately reaches a thickness of 7 µm in the fully grown oocyte. The zona is unique to the ovary, being highly antigenic and accessible to circulating antibody during the two week intra-ovarian oocyte growth phase prior to meiotic maturation and ovulation.

Passive immunization of mice or hamsters with anti-zona sera has been shown to produce reversible contraception without obvious side effects. For example, U.S. Pat. No. 3,992,520 to Gwatkin discloses, inter alia, an anti-serum composition for short-term control of fertility comprising antibody obtained by immunizing an animal with water solubilized zona pellucida of a distinct donor species. This method requires isolation of large amounts of a relatively scarce natural antigen which would not be feasible for certain mammals such as humans. Further, long-term administration of antibodies from a foreign (i.e., "heterologous") species leads to induction of reactive antibodies that will inhibit the contraceptive action of the contraceptive antibodies. Further, administration of serum or products isolated from serum carries inherent risks of transmission of blood-born diseases.

Structural information about the zona pellucida has been available for some years. The mouse zona, for instance, is composed of three sulfated glycoproteins, designated ZP1, ZP2 and ZP3, (J. D. Bleil et al., *Dev. Biol.* 76:185 (1980); S. Shimizu et al., *J. Biol. Chem.* 258:5858 (1983)) which play important roles in fertilization and early development and have average $M_r$s of 200,000, 140,000, and 85,000, respectively. ZP2 and ZP3 appear to be complexed into long filaments which are cross-linked by ZP1 in the zona matrix providing structural integrity to the zona pellucida. Sperm initially bind to ZP3 via O-linked oligosaccharide chains and continued binding involves ZP2 as a secondary sperm receptor. Subsequently, ZP3 induces lysis of the sperm's acrosome which releases enzymes (such as glycosidases and proteases) which are thought to be important for the penetration of the zona pellucida by sperm. Following fertilization, both ZP2 and ZP3 are biochemically modified to prevent additional sperm binding and thereby to facilitate the post-fertilization block to polyspermy.

The zona pellucida in other mammals besides the mouse is known to comprise several distinct glycoproteins components with apparent sizes and, hence naming terminologies, that do not necessarily correspond directly to the mouse ZP1 (185–200 kDa), ZP2 (120–140 kDa) and ZP3 (83 kDa) proteins. The human zona pellucida is composed of three proteins designated ZP1 (90–110 kDa), ZP2 (64–76 kDa) and ZP3 (57–73 kDa) (Shabanowitz et al., *J. Reprod. Fertil.* 82:151–61 (1988); Shabanowitz, 43:260–70 (1990)) and other species in which zona proteins have been characterized include hamster (Moller et al., 137:276–86 (1990), pig (Dunbar et al., *Biol. Reprod.* (1981); Hedrick et al., *Dev. Biol.* 121:478–88 (1987); Yurewicz et al., *J. Biol. Chem.* 262:564–71 (1987), rabbit (Dunbar et al., *Biol. Reprod.* 24:1111–24 (1981) and horse (Millar et al., *J. Reprod. Fert.* 96:815–25 (1992)). The correspondence of specific zona proteins among different species is becoming clearer as additional information on the primary amino acid sequence is deduced from cloned zona pellucida genes (Ringuette et al., *Proc. Natl. Acad. Sci. U.S.A.* 83:4341–45 (1986); Ringuette et al., *Dev. Biol.* 127:287–95 (1988); Chamberlin et al., *Proc. Natl. Acad. Sci. U.S.A.* 87:6014–18 (1990); Chamberlin et al., *Dev. Biol.* 131:207–14 (1989); Liang et al., *Mol. Cell. Biol.* 10:1507–15 (1990); Liang et al., *Dev. Biol.* 156:399–408 (1993); Kinloch et al., *Dev. Biol.* 142:414–21 (1988); Schwoebel et al., *J. Biol. Chem.*

266:7214–19 (1991); Kinloch et al., *Dev. Biol.* 142:414–21 (1990)) and direct sequencing of peptides derived from zona pellucida proteins (Ringuette et al., supra (1986); Yurewicz et al., *Mol. Reprod. Dev.* 33:182–88 (1992)).

In light of the identification of the distinct murine zona pellucida polypeptides, ZP1, ZP2 and ZP3, further experiments on passive immunization with contraceptive antibodies have been conducted. Specifically, rat anti-mouse ZP2 and anti-mouse ZP3 monoclonal antibodies were injected into female mice and were found to bind specifically to the zonae surrounding growing, intra-ovarian oocytes. After ovulation, the binding of the antibody to the zona persisted; and the presence of these antibodies precluded fertilization by preventing sperm from penetration of the zona pellucida. This contraceptive effect was long-term, lasting approximately 15 mouse estrus cycles, but was eventually reversible. There was no evidence of any adverse effect on the development of fertilized embryos to term and no evidence of abnormal ovarian histology or function. However, the antibody binding sites (i.e., "epitopes") recognized on mouse ZP2 and ZP3 by five different rat anti-mouse monoclonal anti-bodies that were tested are not present on other mammalian zonae pellucidae (East et al., *J. Cell Biol.* 98:795–800 (1984); East et al., *Dev. Biol.* 104:49–56 (1984); and East et al., *Dev. Biol.* 109: 268–73 (1985)). This species specificity limits the usefulness of these particular antibodies as contraceptive agents essentially to murine species. In addition, even if analogous murine anti-ZP2 or anti-ZP3 antibodies that inhibit fertilization could be identified for ZP2 or ZP3 of non-murine species, there are inherent side-effects from the repeated administration of heterologous antibodies, as noted above.

There have been several studies on active immunization using preparations of isolated zona pellucidae to immunize rodents, rabbits, and primates (C. J. Henderson, et al., *J. Reprod. Fert.* 83:325 (1988); R. B. L. Gwatkin, et al., 1977, *Fert. Steril.* 28:871 (1977); Drell et al., *Biol. Reprod.* 30:435–44 (1984); Sacco et al., *Biol. Reprod.* 36:481–90 (1987); Jones et al., *J. Reprod. Fertil.* 95:513–25 (1992)).

Further, the U.S. Patent to Gwatkin cited above (U.S. Pat. No. 3,992,520) also discloses a vaccine for the immunological control of fertility in female mammals that consists of an aqueous solution of water solubilized zona pellucida prepared by heating mammalian zone pellucida at 65°–100° C. in an aqueous medium. One example therein describes a bovine antigen preparation intended for use in humans.

U.S. Pat. No. 4,996,297 of Dunbar is limited to three rabbit cDNA sequences S1, P2, and P3 thought to encode rabbit zona proteins, to the use of these cDNAs to produce polypeptides that contain epitopes on three rabbit zona proteins (50 kDa, 75 kDa, and 80 kDa), and to the use of the recombinant polypeptides to vaccinate other mammals in order to elicit antibodies that bind to that mammal's zona pellucida for contraception (i.e., heteroimmunization).

Japanese Patent 63,150,299 discloses a pig zona pellucida antigen for use as a contraceptive vaccine for pigs or humans that is characterized as a glycoprotein of 20 to 30 kDa in molecular weight which can be extracted from soluble pig zona pellucida with 8.5M urea and 2% 2-mercaptoethanol.

Despite positive results under experimental conditions, methods of preparing a vaccine from natural zona pellucida materials are clearly difficult if not outright impractical for commercial use, particularly in the human case, due to limited sources of antigen and to difficulties in quality control of such poorly defined vaccines. Further, widespread ovarian histopathology and dysfunction were reported in rabbits, dogs and primates after active immunization with zonae pellucidae or extracted antigens (see, for example, R. B. L. Gwatkin, et al., *Gamete Res.* 1:19 (1980); A. T. Sacco, *Am. J. Reprod. Immunol. Microbiol.* 15:122 (1977)). Several studies have suggested that both the dose and the purity of the immunogen contributed to these abnormalities, two properties that are particularly difficult to control in such relatively crude antigen preparations.

The effect of the genetic origin of the zona pellucida antigen on its ability to immunize a given species against conception has been examined in several studies. For instance, the efficacies of contraceptive immunizations with pig and rabbit zonae pellucidae on fertility in rabbits was compared. This comparison of results with "alloimmunization" (literally "self-immunization", using antigen from the same species, i.e., an "alloantigen") with those of "heteroimmunization" (using antigen from another species, i.e., an "heterologous" antigen) suggested (D. M. Wood et al., *Biol. Reprod.* 25:439–450 (1981)) that heteroimmunization of rabbits with porcine zonae is more effective in reducing fertility than alloimmunization with rabbit zonae. More recent work using immunoaffinity purified antibodies to zona pellucida to compare immune responses in alloimmunization of male and female rabbits has continued to support the greater effectiveness for contraception of heteroimmunization with zona pellucida antigens. (S. M. Skinner, et al., *J. Reproductive Immunology* 12:81–92 (1987)).

Another general approach toward providing a vaccine related to any antigen involves the use of a particular type of antibody, called an "anti-idiotypic" antibody, as an immunogen to actively immunize an animal. Anti-idiotypic antibodies are antibodies directed to the antigen binding site of another antibody; accordingly, the antigen binding site of the anti-idiotypic antibody mimics or represents an image of the site on the antigen that is bound by the other antibody. U.S. Pat. No. 4,795,634 to Grimes et al. (equivalent of WO 87/05,516) discloses a vaccine that comprises anti-idiotypic antibodies to anti-zona pellucida antibodies to express images of zona pellucida antigens. This vaccine suffers from drawbacks including the fact that anti-idiotypic antibodies are generally difficult and expensive to prepare in amounts and purity satisfactory for vaccine usage, particularly in human applications. Further, heteroimmunization with antigens comprising antibodies from another species may induce predominantly antibodies to sites on the antibody other than the desired target, the antigen binding site. In other words, the desired antigen binding site may not constitute an "immunodominant" antigenic site (or "determinant") for the vaccine antibody protein in a species different from that which produced the vaccine protein (see below for a discussion on the basis of immunodominance). (See also U.S. Pat. No. 4,996,297 of Dunbar et al.)

Another technique for producing vaccines that is known generally in the art is the use of specific isolated polypeptides as antigens, or of peptides representing portions of such polypeptides, in place of crude antigen preparations comprising aqueous extracts of target tissues. Accordingly, European Patent EP-0117934 to Stevens discloses a modified antigen for use in fertility control comprising an unspecified antigen from the zona pellucida, or a peptide having a sequence corresponding to at least part of the sequence of such a zona pellucida antigen, which antigen or peptide has been chemically modified outside the body of the animal. The modified antigen has a greater capacity to induce antibodies than the unmodified antigen from which it is derived. According to the specification and claims, such modification includes coupling the antigen or peptide through a maleimido linkage to a suitable "carrier" protein that is biologically foreign to the animal to be vaccinated and of size sufficient to elicit antibody response. Neither this European application nor any related applications, as yet published, teaches specific zona pellucida polypeptides or peptides that are suitable for use as contraceptive vaccines.

In light of the complexities, difficulties and uncertainties of all the contraceptive vaccines described above, there is yet a need for a simpler, safer, cheaper, more defined and effective contraceptive vaccine. The present invention is based on the premise that vaccination with a "self" zona protein (alloimmunization) is most likely to elicit antibodies that will cross-react with the native zona pellucida and prevent fertilization. Furthermore, by using relatively short peptides as immunogens, the adverse effects on ovarian structure and functions, at least some of which can result from a T cell mediated autoimmune response, can be avoided. However, the success of this approach depends on knowledge of the primary amino acid sequence of the zona pellucida proteins. Because of the paucity of biological material, this sequence information can only be obtained by cloning cDNAs encoding the zona proteins and deducing the amino acid sequence from the nucleic acid sequence. Toward this end, the present inventor and associates have recently constructed a mouse ovarian cDNA expression library and isolated two overlapping ZP3 cDNA clones (M. J. Ringuette et al., *Proc. Natl. Acad. Sci. USA* 83:4341 (1986)), one of which expresses a fusion protein recognized by an anti-ZP3 monoclonal antibody (East et al., *Dev. Biol.* 109: 268 (1985)).

The identity of these clones was confirmed by a comparison of the amino acid sequence encoded by a 60 nucleotide stretch of their nucleic acid sequence with the terminal amino acid sequence (20 amino acids) of a large internal fragment isolated from the ZP3 protein (Ringuette et al., supra 1986)). This fragment was isolated from purified ZP3, following digestion with a protease, by affinity chromatography using an anti-ZP3 monoclonal antibody. Therefore, it was clear that this fragment was capable of expressing an epitope for a contraceptive antibody; however, the location of that epitope within scores of amino acid residues was not known, and as disclosed herein, is distinct from the 20 amino acid sequence obtained. More importantly, the ability of this proteolytic cleavage fragment to serve as an immunogen in a vaccine was not known, nor was there any practical means for preparing sufficient material from natural sources to test that cleavage fragment further.

A first attempt to utilize the cloned mouse ZP3 cDNA described above to produce a vaccine was unsuccessful (S. M. Chamow and J. Dean, 1987, abstract of presentation to the American Society of Biological Chemists). This effort involved testing of the recombinant ZP3-β-galactosidase fusion protein, which contained most of the ZP3 amino acids as well as a larger portion of β-galactosidase and was generated according to well known methods in genetic engineering that have successfully produced other antigens with native immunoreactivity. Immunization with this particular fusion protein, however, failed to induce detectable antibodies that would react with native ZP3; reactivity was detected only after reduction of disulfide bonds and denaturation.

The basis of this failure to induce anti-ZP3 contraceptive antibodies, despite that fact that the cDNA clearly encoded a proteolytic cleavage fragment that reacted with such an antibody, is not entirely clear. It may be that, under the conditions of immunization, the portion of the fusion protein that encoded the contraceptive antibody epitope did not assume the proper conformation to react with such antibodies. In other Words, although the fusion protein surely encoded the amino acids that formed the epitope in the native ZP3 protein, it may be that those amino acids did not exhibit (i.e., did not "display") that epitope in this instance. It is also possible that epitopes for other antibodies, which were located on the β-galactosidase moiety of the fusion, may have been immunodominant over the contraceptive antibody epitopes and thus prevented a detectable contraceptive antibody response (see discussion of immunodominance below). Finally, a combination of these effects and others may have united to prevent the desired contraceptive antibody response to the fusion product of the recombinant DNA which expressed most of the ZP3 polypeptide. These results clearly illustrate the unpredictability of the immunogenicity of a polypeptide under any given set of conditions, no matter how efficacious they may be for other antigens, and the need for experimental determination of the necessary physical form of the amino acids that encode an epitope (e.g., polypeptide size and nature of attached amino acid sequences) to display that epitope and, further, to induce antibodies to it.

Accordingly, it is an object of the present invention to find an efficacious way to use contraceptive antibodies and cloned genes encoding zona pellucida proteins to develop contraceptive vaccines for use in a mammalian female. More particularly, it is an object of this invention to provide such vaccines comprising polypeptides that include defined amino acid sequences that are selected for their ability to display epitopes for contraceptive antibodies.

Additional immunological analyses of the individual ZP polypeptide components have been carried out. For example, specific monoclonal and polyclonal antibodies have been employed to define distinct antigens of the porcine zonae pellucidae, leading to the suggestion that there are both unique and shared antigenic determinants present in the individual components of the zona pellucida, but that the immunodominant determinants appear to be unique to each glycoprotein (T. M. Timmons, et al., *Biology of Reproduction* 36:1275–1287 (1987)). Finally, there has been a report of an effort to molecularly clone cDNAS encoding specific antigenic sites from rabbit ZP proteins using antibodies that recognize determinants found on ZP antigens of several species (P. Cheung et al., 1987, abstract of a presentation at the twenty-seventh annual meeting of the American Society for Cell Biology, St. Louis, Mo., November 16–20, *J. Cell Biol.* 105, no. 4 part 2, 334A). This abstract reported in part that:

"These studies demonstrated that cross-species affinity purification of antibodies is an effective method for isolating cDNA clones expressing antigens which are shared among different mammalian species."

However, no specific nucleotide or amino acid sequences were disclosed in this abstract, nor was the contraceptive potential of the antibodies discussed; indeed, there was no mention of any contraceptive vaccine.

In a speculative exposition on the use of recombinant DNA and synthetic peptide technologies for development of a human contraceptive vaccine from porcine zona pellucida antigens (C. J. Henderson, et al., *J. Reprod. Fert.* 83:325 (1988)), which was entitled "The future . . . ", the identification of amino acid sequences displaying epitopes for contraceptive vaccines on a particular porcine polypeptide is anticipated, although absolutely no sequences of the polypeptide are disclosed. Nevertheless, this reference goes on to hypothesize that known vaccine technologies, including synthetic peptides and vaccinia virus expression vectors, will provide successful human vaccines based on this particular porcine polypeptide that is known to be immunologically related to human zona pellucida antigens. Furthermore, while asserting that monoclonal antibodies to this polypeptide that exert a contraceptive effect "will be extremely important in defining the epitopes with contraceptive potential . . . ", this report also notes that, despite obtaining monoclonal antibodies reactive with this polypeptide, the authors "have failed to generate a monoclonal antibody with contraceptive effect; this is in accord with other published reports . . . ."

Although a complete exposition of the current theoretical basis of immunogenicity and antigenicity of polypeptides is beyond the scope of the present disclosure, a brief discussion of selected principles and terms of this active art will facilitate further understanding of the instant invention. [In this application, absent an express statement to the contrary, each use of the term "polypeptide" encompasses any polymer comprising two or more amino acids coupled by peptide linkages (i.e., dipeptides, oligopeptides, peptides, polypeptides) as well as proteins consisting of multiple polypeptide subunits.]

Accordingly, it should be noted, first, that the necessary and sufficient properties of a polypeptide for inducing antibodies cannot be predicted for any given set of conditions (e.g., for a particular species, or for presentation in a certain form). Nevertheless, much more has been learned about this subject in the past decade than is reflected in any of the art cited so far herein, and it is a further object of the present invention to exploit aspects of this knowledge for design of advantageous contraceptive vaccines.

In particular, comprehension of the present invention will be aided by the now widely held view that the nature and level of the immune response to a polypeptide depends on its interactions with at least two distinct classes of immune system cells, namely B-cells and T-cells. In simple terms, the role of B-cells in immunity may be thought of as recognition of the specific sites on macromolecules to which antibodies are produced and subsequent production of those antibodies. These B-cell recognition sites, which provide the main basis for immune recognition of non-self molecules and are also called B-cell epitopes, are of a size corresponding to about that of the antigen binding site on an antibody, typically of a diameter equivalent to the length of a peptide containing about four to six amino acids.

[It may be noted here that there exists a formal distinction between the epitope for a B-cell and that of its related antibody. In other words, due to complex biological mechanisms that intervene between the recognition by a B-cell of a given site on an antigen and the consequent production of antibodies to that site, it is possible that the ultimate antibody recognition site may not be precisely identical to the initially recognized B-cell epitope. However, for the present purposes, a B-cell epitope may be considered to be essentially the same structure as the binding site for the corresponding antibody.]

The functions of T-cells, on the other hand, relate in large measure to helping to activate antibody production by B-cells upon initial exposure to an antigen, as well as to enhancing their antibody response upon subsequent reexposures (i.e., to "immune memory" or the "amnestic" response). To play their roles in immunity, T-cells must also recognize specific sites on an antigen to which antibodies are produced, and such T-cell epitopes are about the same size as B-cell epitopes.

B-cell and T-cell epitopes on any given polypeptide, however, need not comprise the same amino acid residues.

In fact, it will be appreciated by those of ordinary knowledge in the current art of peptide immunology at the molecular level, that even in a peptide consisting of only half a dozen amino acids, there may coexist several different B-cell epitopes (comprising, for instance, from two to four atoms that contact complementary structures on the antibody) and one or more distinct T-cell epitopes which may or may not include atoms of amino acids also included in a B-cell epitope.

It is also well known that the vast majority of small peptides (containing six to twenty amino acids, for instance) that have been tested for induction of antibodies are considerably less potent immunogens than the larger proteins from which they have been derived, despite ample ability of the peptides to bind to antibodies directed against those larger proteins. Certain chemical modifications of a peptide, particularly coupling of the peptide to a larger proteinaceous "carrier", generally enhance the immune response to a small peptide.

Although the role of such a carrier still may not be fully understood in all respects, it has been clearly established, in particular, that there is no specific minimum size requirement for peptides in general to induce a substantial immune response. Rather, it is now widely believed that a major function of the carrier is to provide T-cell epitopes in close association with the B-cell epitopes on the short peptide which is statistically unlikely to contain both T-cell and B-cell sites recognized by the immune system of any given individual.

It may also be noted here that it has been shown that a T-cell epitope taken from one protein, in the form of a short peptide, may be combined with a short peptide comprising a B-cell epitope of another protein, to form a single peptide that induces a more complete and higher level immune response than either peptide alone.

More broadly, it is now widely accepted that the capability of any individual to mount any immune response to a given epitope, as defined by a precise configuration of a small number of atoms, depends ultimately on the genetic make-up of the immune system genes which separately control the specificities of antigen recognition by B-cells and T-cells. Further, it is understood that the ability of a given B-cell epitope to induce cognate antibodies (i.e., antibodies which recognize that epitope) also depends upon the context within which that epitope is presented to the immune system, in terms of both associated T-cell epitopes and other B-cell epitopes. The latter sites may be "immunodominant" relative to the selected B-cell epitope of interest, that is, they may contend more effectively for the attention of the immune system than the selected B-cell epitope and thereby distract limited system resources from mounting the desired response to that selected epitope. In other words, B-cell epitopes that do not induce detectable antibodies in the presence of other, so-called immunodominant epitopes, which frequently occur in large polypeptides, often do induce significant levels of cognate antibodies when presented in a different context that lacks such immunodominant sites, on a short peptide, for example.

In conclusion, it is a further object of the present invention to exploit various consequences of the above noted characteristics of and distinctions between B-cell and T-cell epitopes, as well as methods for predicting and actually detecting amino acid sequences that serve as T-cell or B-cell epitopes. These will be discussed further below, as needed, in relation to the description of the present invention.

SUMMARY OF THE INVENTION

The recent molecular cloning, by the present inventor, of DNA segments corresponding to the mouse ZP3 and ZP2 genes, the human ZP3 and ZP2 genes, and the subsequent characterization of the nucleotide sequences of their messenger RNAs (mRNAs) and the amino acid sequences encoded thereby, have provided sufficient molecular detail of zona proteins to enable a new contraceptive approach. This strategy is based on active alloimmunization with a zona pellucida polypeptide which includes an amino acid sequence that is selected to display at least one epitope for binding of an antibody that inhibits fertilization of an oocyte by a sperm.

The complete nucleotide sequence of the mouse ZP3 messenger RNA and the amino acid sequence encoded thereby has been disclosed previously by the present inventor and associates (M. J. Ringuette et al., Dev. Biol. 127:287–296 (1988), published Jun. 13, 1988, the entire contents of which are hereby incorporated herein by reference). The complete nucleotide sequence of the mouse ZP2 (Liang et al., Mol. Cell. Biol. 10:1507–15 (1990)), the human ZP3 (Chamberlin et al., Proc. Natl. Acad. Sci. U.S.A. 87:6014–18 (1990)) and the human ZP2 Liang et al., Devel. Biol. 156:399–408 (1993) messenger RNAs and the amino acid sequences encoded thereby have also been disclosed and the entire contents of the published documents are hereby incorporated herein by reference.

The present inventor and associates have also reported (M. Chamberlin et al., 1987, abstract of a presentation at the twenty-seventh annual meeting of the American Society for Cell Biology, St. Louis, Mo., November 16–20, J. Cell Biol. 105, no. 4 part 2, 334A) that mouse genomic clones of the ZP3 gene and a human genomic DNA clone of the ZP3 gene have been isolated by virtue of their homology to the previously isolated murine ZP3 cDNAS. However, this abstract does not disclose specific nucleotide or amino acid sequences of any mouse or human DNA clone, nor does it even mention any concept of a contraceptive vaccine. Further, the mouse and human ZP2 cDNA sequences have not been disclosed previously.

Enabled by an oligonucleotide probe based on the short ZP3 cDNA sequence that was published by the present inventor and associates (Ringuette et al., supra (1986)), and subsequent to publication of the complete mouse ZP3 cDNA sequence (M. J. Ringuette et al., Dev. Biol. 127:287 (1988)), others have also reported isolation and sequences of genomic DNA clones of a mouse ZP3 gene and the amino acid sequence encoded therein (R. A. Kinloch et al., 1988, Proc. Natl. Acad. Sci. U.S.A. 85:6409–413 (1988)). This information was also used to isolate genomic DNA clones of hamster ZP3 and, by comparison with previously described mouse ZP3 genes, to deduce the amino acid sequence of the resultant polypeptide chain (Kinloch et al., Devel. Biol. 142:414–21 (1990)). Independently, others have reported the isolation of a cDNA encoding rc55, a rabbit zona pellucida protein (Schwoebel et al., J. Biol. Chem. 266:7214–19 (1991)), that does not appear to be the homologue of either mouse ZP2 or ZP3.

Whereas the prior art on contraceptive vaccines based on zona pellucida antigens has been and remains primarily focused on heteroimmunization, the present invention relates to contraceptive vaccines based on cloned zona pellucida genes and the strategy of alloimmunization with polypeptides including defined amino acid sequences that are selected for displaying epitopes to contraceptive antibodies. The advantages of this approach include the ability to produce and utilize those immunogens displaying the most effective B-cell epitopes for inhibition of fertilization regardless of whether or not they happen to be conserved in several species. Further, this vaccine strategy minimizes the likelihood of inducing antibodies with deleterious cross-reactivity with epitopes on molecules other than zona pellucida polypeptides. Ultimately, by reducing in the vaccine the number of B-cell epitopes that produce antibodies which, even though they bind to a zona pellucida antigen, do not block conception, this invention focuses the immune response to the vaccine on precisely those amino acids that are most critically situated to facilitate the contraceptive effect of antibodies. Further, by focusing on those epitopes that are most useful for contraceptive purposes, the present invention minimizes potential interference with establishment of effective immunity to those critical contraceptive epitopes from extraneous epitopes that may be immunodominant to those critical sites and, therefore, may prevent an adequate contraceptive antibody response to them. In addition, by focusing on these epitopes, the potential for adverse immunological response due to the induction of autoimmune responses can be minimized (Rhim et al., J. Clin. Invest. 89:28–35 (1992)).

It is understood that, in the practice of the present invention, epitopes may be used which happen to be conserved in the zona pellucida proteins of more than one species. However, in contrast to previous efforts to employ zona pellucida antigens in vaccines wherein the first concern has been to identify cross-reacting epitopes in heterologous antigens without initial regard for the functionality of such epitopes in inducing contraceptive antibodies, as described in some references cited herein above, it will be appreciated that use of conserved epitopes in the instant invention is entirely incidental to the goal of providing epitopes that are effective for inducing contraceptive antibodies in the particular target species intended for a given vaccine.

Accordingly, the present invention relates to a contraceptive vaccine for use in a mammalian female comprising a polypeptide which includes an amino acid sequence that is selected to display at least one epitope for binding of an antibody that inhibits fertilization of an oocyte by a sperm. This contraceptive antibody epitope is an epitope for which there is a functional homolog displayed on a zona pellucida protein that originates from the species in which the said vaccine is used. The zona pellucida protein displaying the functionally homologous epitope advantageously is either a ZP3 protein or a ZP2 protein or a ZP1 protein.

In other words, both the amino acid sequence of a polypeptide of this vaccine and a zona pellucida protein display epitopes which are functionally homologous in that they both are able to bind the same antibody that inhibits fertilization of an oocyte by a sperm. The fact that this vaccine polypeptide and a zona pellucida protein both display functionally homologous binding sites for the same antibody does not imply, however, that these binding sites are encoded by the same amino acid sequence in each instance, i.e., the polypeptides displaying the two epitopes are not necessary structurally homologous at the level of amino acid sequences encoding the epitopes.

By the phrase "originating from" it is meant that the zona pellucida protein is encoded in the genome of the species in which the said vaccine is used.

It will be understood from the foregoing Background that the nomenclature of zona pellucida proteins comprising ZP1, ZP2 and ZP3 has been defined in the mouse system and that other nomenclature or no nomenclature may be used in other mammalian systems. However, the present inventor has clearly demonstrated that the genes and mRNAS and, hence, the amino acid sequences of the major murine zona pellucida proteins (for example, the ZP3 and ZP2 proteins of the mouse) are conserved throughout diverse mammalian species (see below). In light of this high degree of structural similarity, a high degree of functional homology is also to expected in terms of the ability of homologous positions to serve as epitopes of contraceptive antibodies. Accordingly, the terms "ZP3 protein", "ZP2 protein", and "ZP1 protein" contemplate not only the murine forms of these highly conserved zona pellucida proteins, but also the homologous counterparts of any other mammalian species, regardless of any other terminology by which such other proteins may be known in the art.

Contraceptive antibodies suitable for the practice of the present invention may be generated using zona pellucida antigens from natural sources, according to various published procedures. Alternatively, such antibodies may be produced advantageously by immunization with a polypeptide produced in a recombinant expression system comprising a DNA segment of the present invention. Various methods for identifying antibodies, including monoclonal antibodies, that inhibit the fertilization of an oocyte by a sperm have also been published (e.g., East et al., *Dev. Biol.* 109:268 (1985)).

In the polypeptide of the vaccine of this invention, the amino acid sequence which displays an epitope for a contraceptive antibody may include all or part of the same amino acid sequence responsible for displaying the functionally identical epitope on a zona pellucida protein. In some cases, a single epitope for binding a given antibody comprises more than one contiguous amino acid sequence of a polypeptide (see discussion of "discontinuous epitope", below); accordingly, the present invention contemplates that the polypeptide of the vaccine may include at least one amino acid sequence of a zona pellucida protein that displays a functionally homologous epitope.

An amino acid sequence displaying an epitope for an available contraceptive antibody may be selected from all the sequences in a zona pellucida protein using a known contraceptive antibody. For example, a contraceptive antibody may be used to isolate a peptide displaying its epitope from a proteolytic digest of a zona pellucida protein by means of affinity chromatography methods that are well known in the art.

Alternatively, a DNA sequence encoding an amino acid sequence which displays an epitope for a contraceptive antibody may be isolated by standard genetic engineering approaches. These involve screening of clones of fragments of a gene for a zona pellucida protein for the ability to express an amino acid sequence that binds the contraceptive antibody. In addition, if sufficient zona proteins can be produced by standard recombinant DNA techniques, it may be possible to determine the 3-dimensional structure by standard biochemical techniques (e.g. nuclear magnetic resonance, and X-ray diffraction).

Yet another way to identify an amino acid sequence that displays the epitope of a contraceptive antibody is to employ the well known strategy of chemical synthesis of every distinct peptide that could possibly display an antibody epitope. For instance, technology is commercially available for the rapid synthesis and antibody reactivity testing of all peptides of six amino acids that occur sequentially in the sequence of a protein and overlap by one amino acid. In the practice of the present invention, the sequences to be synthesized are determined advantageously from the nucleotide sequence of a cloned gene for a zona pellucida protein.

In another embodiment of this aspect of the present invention, the amino acid sequence that displays the epitope for a contraceptive antibody in the vaccine may be some type of analog of the amino acid sequence for that epitope on the zona pellucida protein.

One type of analog that this embodiment includes is a synthetic peptide known as a "mimotope" by H. M. Geysen, the inventor of the technology used to create such analogs, for which kits of materials are now commercially available. In a substantial number of cases, this synthetic epitope generation approach produces amino acid sequences that are functional analogs of known epitopes for a given antibody, and these analogs can induce other antibodies that recognize the same epitope as the original selected antibody. These analog sequences, however, usually do not contain the amino acids in the natural amino acid sequence that displays the selected epitope. Thus, this type of analog sequence mimics a naturally occurring structure that displays an epitope, hence, the term "mimotope". An important feature of this particular aspect of this embodiment of the present invention is that it is not necessary to identify the natural amino acid sequence displaying the epitope of the desired contraceptive antibody; in fact, this method can produce small peptide analogs of natural epitopes comprising amino acids located in distinct positions of a protein that are separated by many amino acids (i.e., so-called "discontinuous epitopes" as opposed to those epitopes encoded by a single short continuous amino acid sequence).

In the term "analog", this aspect of the present invention also contemplates the application of well known principles of sequence conservation during the evolution of protein families to identify epitopes for contraceptive antibodies in a selected zona pellucida protein for which such antibodies are not yet available. If the amino acid sequence of this zona pellucida protein is highly homologous to that of related protein from another species, and if epitopes for such contraceptive antibodies have been defined in the sequence of this latter protein, then the general structural homology between the two proteins may be used to indicate those sequences in the selected protein that display epitopes for contraceptive antibodies that are analogous to those known for the second protein.

In other words, when two short, distinct amino acid sequences are known to occupy the same position in two proteins of substantially homologous structure (i.e., overall amino acid sequence and, consequently, three-dimensional conformation), then if one of the two sequences displays an epitope for an antibody with a particular biological effect, the other sequence has a high probability of displaying epitopes for other antibodies with the same biological effect. According to this aspect of this invention, a known epitope for a contraceptive antibody is embodied by an amino acid sequence identified in a mouse ZP3 protein by screening cloned fragments of a cloned DNA for expression of suitable epitopes, and one analog of this amino acid sequence is embodied by the sequence of amino acids that occupies the homologous position in the human ZP3 protein. A second epitope for a known contraceptive antibody is embodied by an amino acid sequence identified in a mouse ZP2 protein as above and one analog of this amino acid sequence is embodied by the sequence of amino acids which occupies the homologous position in the human ZP3 protein. This human analog of a mouse ZP3 or ZP2 epitope (which also may be considered to be a "homologue" of that epitope), is to be incorporated into a vaccine for use in human beings, of course, according to the alloimmunization aspect of the present invention.

It is understood that chemically synthesized peptides may be used advantageously as polypeptides of the present invention, especially since the synthesis of such peptides comprising 30 to 50 or even more amino acids can now be achieved on scales sufficient for vaccine purposes (in batches of 1 gram or more, for example). One such synthetic peptide is embodied by a mouse ZP3 peptide and a mouse ZP2 peptide that are described below.

It should be particularly noted that the polypeptides of the present invention do not include idiotypic antibodies or large fragments of such antibodies, since the disadvantages of using such polypeptides to present epitopes of zona pellucida proteins has been discussed above in the Background in regard to prior art on such antibodies. However, the present invention does contemplate smaller polypeptides comprising mainly those amino acid sequences of such idiotypic antibodies that actually comprise the analog of the original zona pellucida protein epitope.

Further, as will be appreciated from the Background discussion of immunogenicity of polypeptides, the immunogenicity of polypeptides or peptides of the present invention in terms of raising higher titers of contraceptive antibodies with greater affinities for their epitopes, particularly such immunogenicity of small (synthetic) peptides, may be enhanced advantageously by covalent coupling to another polypeptide or peptide, especially to another amino acid sequence displaying a T-cell epitope. In addition, it will be appreciated that, as is customary for vaccines, the polypeptides of the present invention will be delivered in a pharmacologically acceptable vehicle. Vaccines of the present invention may also advantageously comprise effective amounts of immunological adjuvants that are known to enhance the immune response to immunogens in general, particularly adjuvants that enhance the immunogenicity of small synthetic peptides.

In another aspect, the present invention further relates to certain DNA segments that encode mouse ZP3 or ZP2 proteins and human ZP3 or human ZP2 proteins. This invention also relates to cultures of recombinant cells containing a DNA segment of this invention and to methods for the synthesis and isolation of polypeptides and peptides of this invention.

The present invention also relates to recombinant DNA molecules comprising a DNA segment of this invention and a vector. A number of vectors may be utilized such as, for example, the vaccinia virus.

In particular, the present invention includes a contraceptive vaccine for use in a mammalian female comprising a polypeptide which consists essentially of the mouse zona pellucida 3 (ZP3) amino acid sequence Cys-Ser-Asn-Ser-Ser-Ser-Ser-Gln-Phe-Gln-Ile-His-Gly-Pro-Arg-Gln or a homologous mammalian amino acid sequence derived from a homologous region of a ZP3 protein. The mammalian amino acid sequence is included in a zona pellucida protein originating from the species in which the vaccine is used. The vaccine also includes a pharmacologically acceptable vehicle. It must be noted that portions of the sequence may also be utilized in the vaccine.

The homologous mammalian amino acid sequence in the vaccine may be, for example, Cys-Gly-Thr-Pro-Ser-His-Ser-Arg-Arg-Gln-Pro-His-Val-Met-Ser-Gln. This sequence is derived from a human ZP3 protein. It should be noted that portions of the 16 amino acid sequence may be utilized in the vaccine.

Additionally, the present invention relates to a contraceptive vaccine for use in a mammalian female comprising a polypeptide which consists essentially of the mouse zona pellucida 2 (ZP2) amino acid sequence Ile-Arg-Val-Gly-Asp-Thr-Thr-Thr-Asp-Val-Arg-Tyr-Lys-Asp-Asp-Met or a homologous mammalian amino acid sequence derived from a homologous region of a ZP2 protein. The mammalian amino acid sequence is included in a zona pellucida protein originating from the species in which the vaccine is used. The vaccine also includes a pharmacologically acceptable vehicle. Portions of the 16 amino acid sequence may be utilized in the vaccine.

The homologous mammalian amino acid sequence referred to above may be, for example, Ile-Arg-Val-Met-Asn-Asn-Ser-Ala-Ala-Leu-Arg-His-Gly-Ala-Val-Met and is derived from a human ZP2 protein. It should be noted that portions of the 16 amino acid sequence may also be utilized in the vaccine.

Each of the above-vaccines may include an effective amount of an adjuvant. Furthermore, the mammalian female may be a cat, a dog, a pig, a cow, or a woman. It is important to note that the polypeptide is derived from the same species to which it is administered in vaccine form.

The present invention also relates to a contraceptive vaccine comprising a polypeptide which consists essentially of a synthetic peptide corresponding to the mouse zona pellucida (ZP3) amino acid sequence Cys-Ser-Asn-Ser-Ser-Ser-Ser-Gln-Phe-Gln-Ile-His-Gly-Pro-Arg-Gln or a synthetic peptide corresponding to a homologous mammalian amino acid sequence derived from a homologous region of a ZP3 protein, for binding of an antibody that inhibits fertilization of an egg by a sperm. The mammalian amino acid sequence, as noted above, is included in a zona pellucida protein originating from the species in which said vaccine is used. The vaccine may further comprise a pharmacologically acceptable vehicle. Portions of the 16 amino acid sequence may also be used.

The homologous mammalian amino acid sequence may be, for example, Cys-Gly-Thr-Pro-Ser-His-Ser-Arg-Arg-Gln-Pro-His-Val-Met-Ser-Gln and is derived from a human ZP3 protein. Portions of the homologous sequence may be utilized in the vaccine.

The present invention also relates to a contraceptive vaccine comprising a polypeptide which consists essentially of a synthetic peptide corresponding to the mouse zona pellucida (ZP2) amino acid sequence Ile-Arg-Val-Gly-Asp-Thr-Thr-Thr-Asp-Val-Arg-Tyr-Lys-Asp-Asp-Met or a synthetic peptide corresponding to a homologous mammalian amino acid sequence derived from a homologous region of a ZP2 protein, for binding of an antibody that inhibits fertilization of an egg by a sperm. The mammalian amino acid sequence is included in a zona pellucida protein originating from the species in which the vaccine is used. The vaccine may further comprise a pharmacologically acceptable vehicle. It should be noted that portions of the sequence shown above may be utilized in the vaccine.

The homologous mammalian amino acid sequence may be, for example, Ile-Arg-Val-Met-Asn-Asn-Ser-Ala-Ala-Leu-Arg-His-Gly-Ala-Val-Met which is derived from a human ZP2 protein. Portions of this sequence may be utilized in the vaccine.

Additionally, the present invention also includes a DNA segment encoding the mouse ZP3 protein or a portion thereof, a DNA segment encoding the mouse ZP2 protein or a portion thereof, a DNA segment encoding the human ZP3 protein or a portion thereof, and a DNA segment encoding the human ZP2 protein or a portion thereof.

The invention also encompasses a recombinant DNA molecule comprising a DNA segment encoding the human ZP3 or human ZP2 protein, or a portion of each protein, and a vector. Additionally, the invention includes cultures of host cells transformed or transfected with the recombinant DNA molecules or constructs.

The invention also includes a method of producing at least a portion of a human ZP3 or human ZP2 protein comprising culturing the above-cells under conditions such that the protein is produced and isolating said protein from culture media or from the cells.

The invention also includes an antibody specific for a protein having the amino acid sequence of the human ZP3 or ZP2 protein or a portion thereof. This antibody inhibits fertilization of a human oocyte by a sperm.

Furthermore, the invention also includes the purified proteins encoded by the DNA segments referred to above. All U.S. patents and publications referred to herein are hereby incorporated by reference.

The present invention may be understood more readily by reference to the following detailed description of specific embodiments and the Examples and Figures included therein.

BRIEF DESCRIPTION OF THE DRAWINGS

FIG. 1: Nucleic Acid Sequence of Mouse ZP3 cDNA (SEQ ID NO:1) and Deduced Amino Acid Sequence (SEQ ID NO:2) of Mouse ZP3 Protein.

Figure 5:
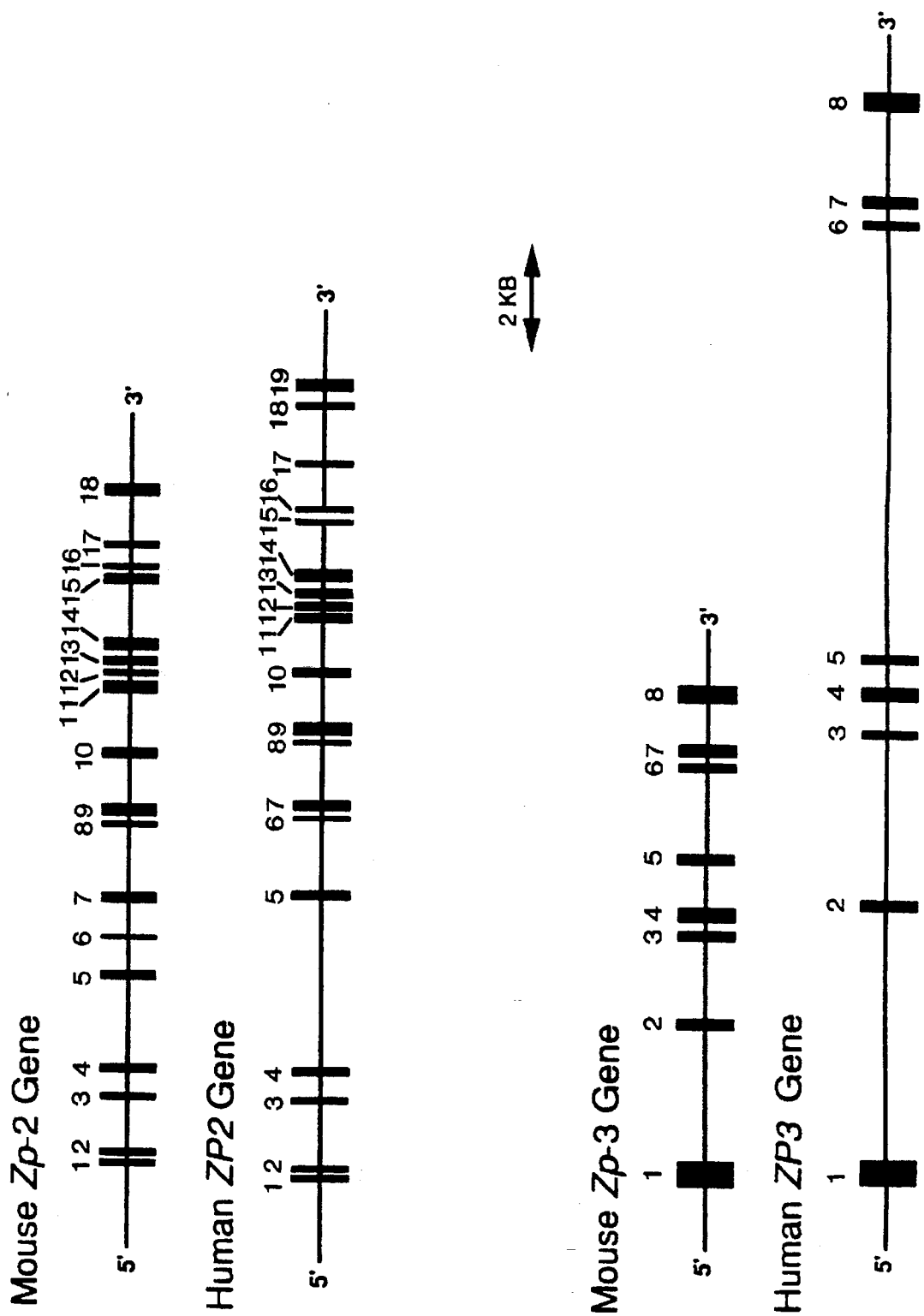

The nucleic acid sequence of near-full-length cDNAs and exon 1 of the Zp-3 gene were used to deduce the structure of the ZP3 mRNA and resultant protein. The initiation and termination codons are boxed, and the polyadenylation signal is overlined. The single 1272-nt open reading frame is translated into a 424 amino acid ZP3 protein in line 2. The proposed 22-amino acid signal peptide is indicated by a wavy line, and the arrow points to the proposed signal peptidase cut site. Amino acid sequences which were experimentally determined by isolation and direct sequencing of an internal ZP3 peptide are underlined with a dashed line. The 6 potential N-linked glycosylation sites (Asn-X-Thr/Ser) are underlined with a solid line (Ringuette et al., *Dev. Biol.* 127:287–95 (1988)).

Figure 2A:
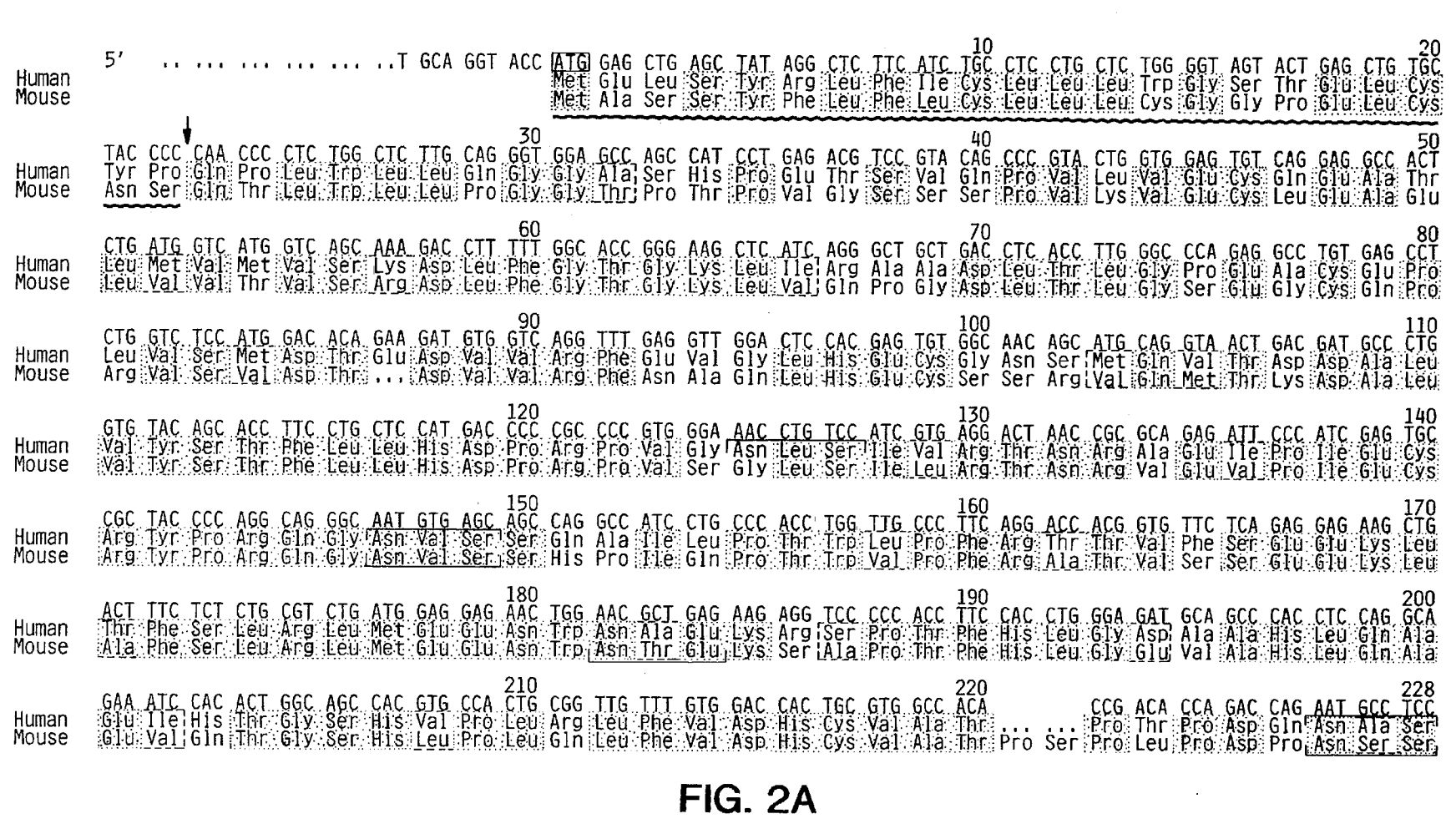
Figure 2B:
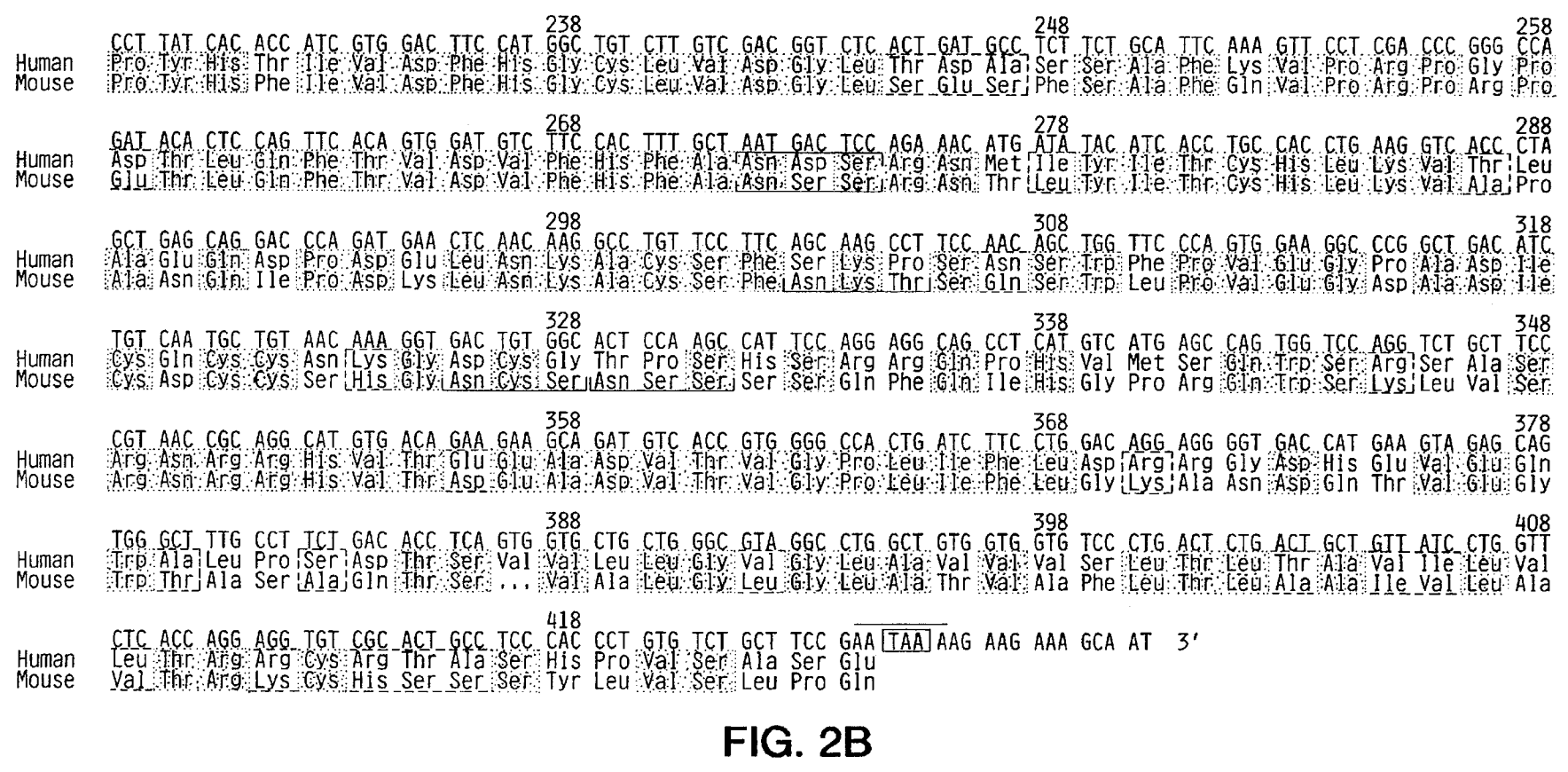

FIG. 2: Nucleic Acid Sequence of Human ZP3 cDNA (SEQ ID NO:3) and Deduced Amino Acid Sequence of Human ZP3 Protein (SEQ ID NO:4) Compared to the Amino Acid Sequence of Mouse ZP3 Protein (SEQ ID NO:5).

The first line is the nucleic acid sequence of human ZP3 mRNA containing 1289 nt determined from human cDNA and genomic sequences (Chamberlin et al., *Proc. Natl. Acad. Sci. USA* 87:6014–18 (1990)). The initiation and stop codons are boxed, and the polyadenylation signal overlined. The single 1272-nt open reading frame is translated into a 424-amino acid peptide in the second line and aligned in the third line with the 424 amino acids of mouse ZP3 protein (Ringuette et al., *Dev. Biol.* 127:287–95 (1988)). Identical amino acid residues in mouse and human ZP3 are shaded; conserved changes (Dayhoff et al., *Proc. Natl. Acad. Sci. USA* 76:2170–74 (1979)) are enclosed in boxes with dotted lines. The putative 22-amino acid signal peptide is indicated by a wavy line, and the arrow points to the proposed signal peptidase cut site. The four potential N-linked glycosylation sites [Asn-Xaa-(Thr or Ser)] of human ZP3 are bracketed from above, and the six potential sites of mouse ZP3 are bracketed from below. Three of the sites are conserved between the two species.

FIG. 3: Nucleic Acid Sequence of Mouse ZP2 cDNA (SEQ ID NO:6) and Deduced Amino Acid Sequence of Mouse ZP2 Protein (SEQ ID NO:7).

The nucleic acid sequence of the near-full-length cDNAs and exon 1 of the Zp-2 gene were used to deduce the structure of the ZP2 mRNA and resultant protein. The initiation and termination codons are boxed, and the polyadenylation signal is overlined. The single 2139 nucleotide open reading frame is translated into a 713 amino acid protein in line 2. The 34-amino acid signal peptide is indicated by a wavy line, and the arrow points to the signal peptidase cut site. Amino acid sequences which were experimentally determined by isolation and direct sequencing of an N-terminal and an internal ZP2 peptide are underlined with a dashed line. The 7 potential N-linked glycosylation sites (Asn-X-Thr/Ser) are underlined with a solid line (Liang et al., *Mol. Cell. Biol.* 10:1507–15 (1990)).

Figure 4A:
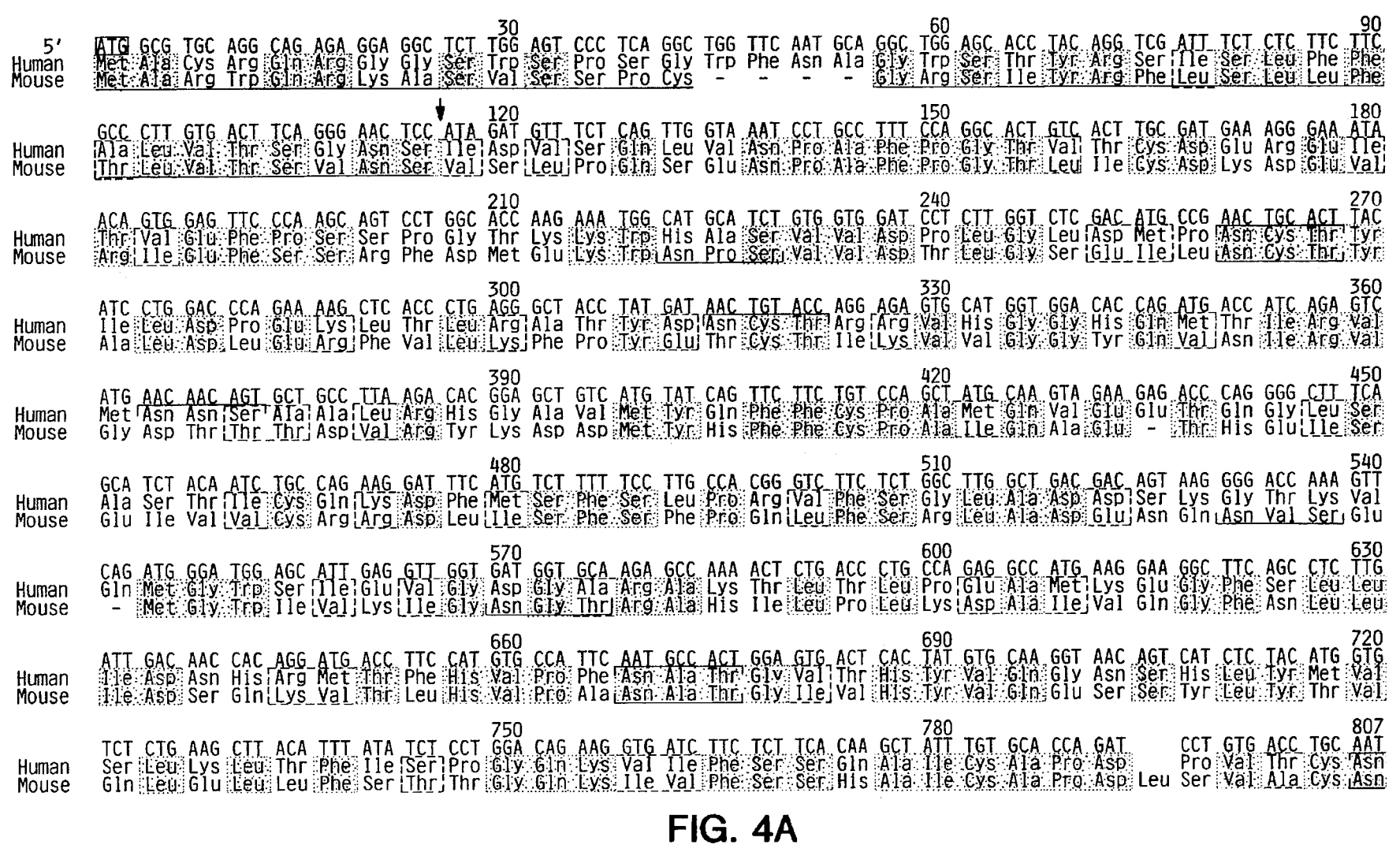
Figure 4B:
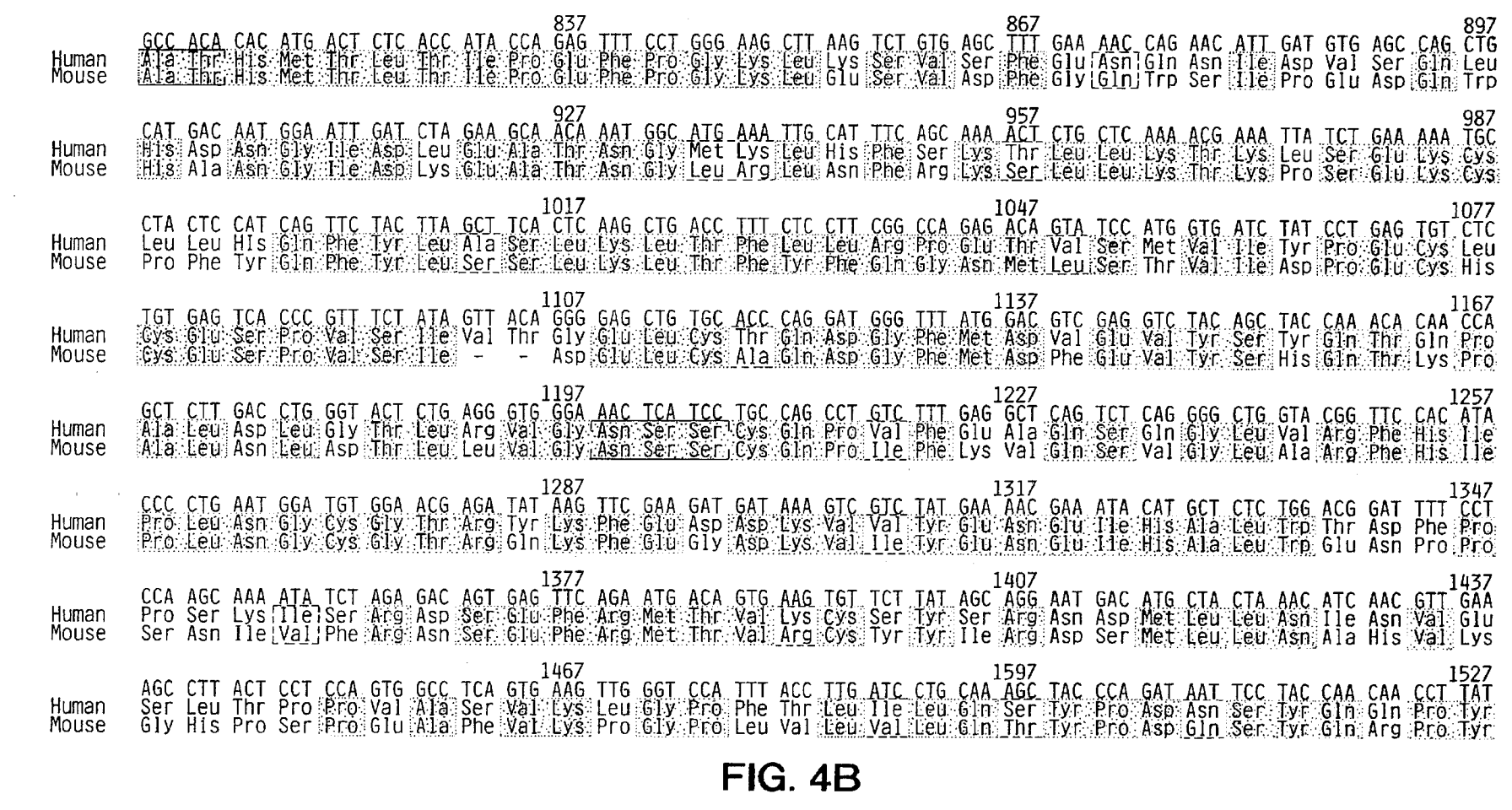
Figure 4C:
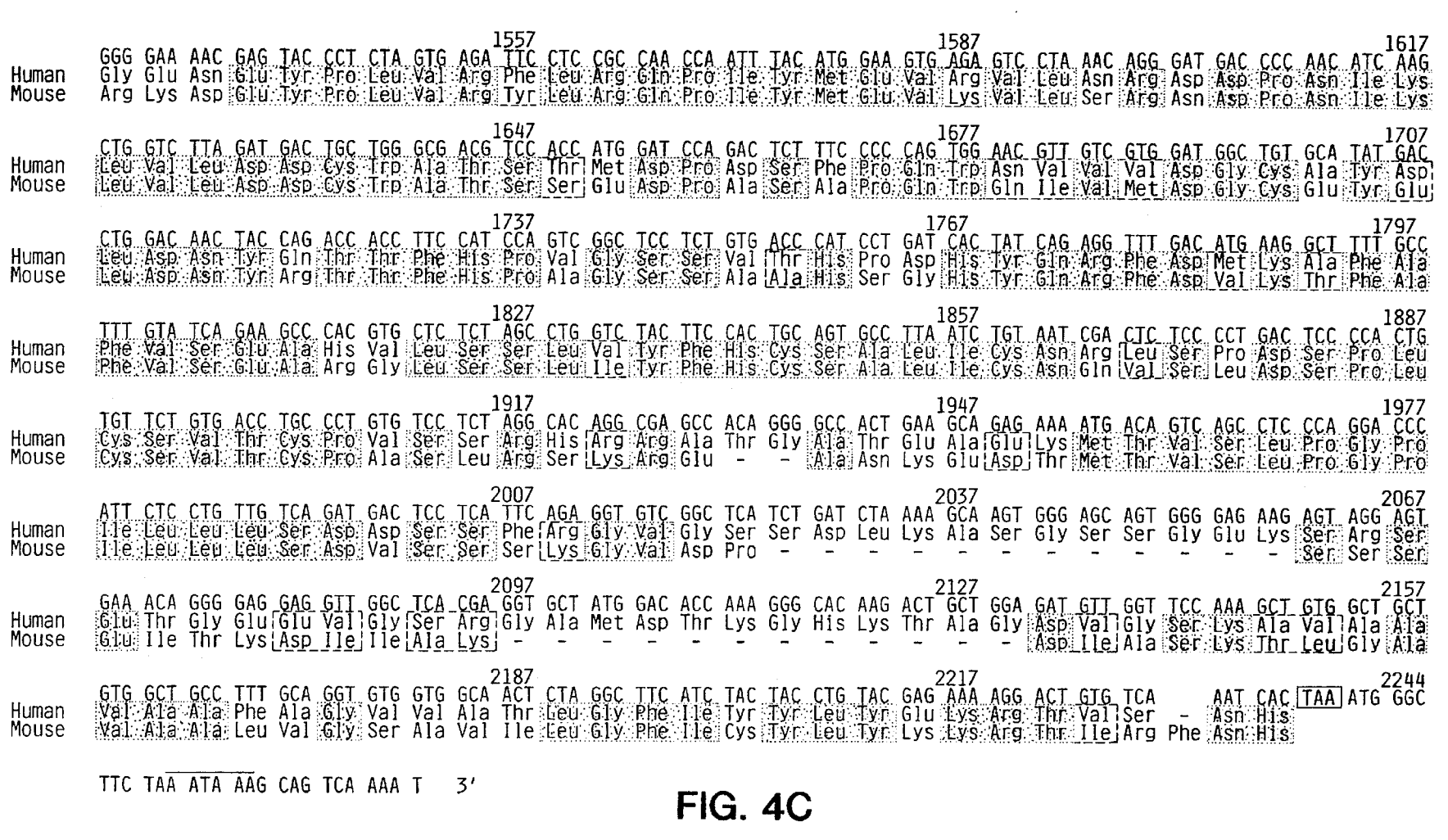

FIG. 4: Nucleic Acid Sequence of Human ZP2 cDNA (SEQ ID NO:8) and Deduced Amino Acid Sequence of Human ZP2 Protein (SEQ ID NO:9) Compared to the Amino Acid Sequence of Mouse ZP2 Protein (SEQ ID NO:10).

The nucleic acid sequence of the near-full-length cDNAs and exon 1 of the ZP2 gene were used to deduce the structure of the ZP2 mRNA and resultant protein (Liang et al., *Dev. Biol.* 156:399–408 (1993)). The initiation and termination codons are boxed, and the polyadenylation signal is overlined. The single 2235 nucleotide open reading frame is translated into a 745 amino acid protein in line 2 and aligned in line 3 with the 713 amino acid mouse ZP2 (Liang et al., *Mol. Cell. Biol.* 10:1507–15 (1990)). The putative 38-amino acid signal peptide is underlined, and the arrow points to the predicted signal peptidase cut site. Identical amino acid residues between human and mouse ZP2 are shaded; conserved changes (Dayhoff et al., *Proc. Natl. Acad. Sci. USA* 76:2170–74 (1979)) are enclosed in boxes with dotted lines. The potential N-linked glycosylation sites (Asn-X-Thr/Ser) are marked in bold brackets.

FIG. 5: Exon Maps of Mouse and Human ZP2 Genes and of Mouse and Human ZP3 Genes.

Dark vertical bars represent the exons. The double-headed arrow represents 2 kbp of genomic DNA. Mouse Zp-2 is a single copy gene containing 18 exons which span 12.1-kbp (Liang et al., *Mol. Cell. Biol.* 10:1507–15 (1990)). Human ZP2 contains 19 exons, spanning 14-kbp (Liang et al., supra (1993)). Mouse Zp-3 is a single copy gene spanning 8.6-kbp and containing 8 exons (Chamberlin et al., *Dev. Biol.* 131:207–14 (1989) ). Human ZP3 spans 18.3-kbp and contains 8 exons (Chamberlin et al., *Proc. Natl. Acad. Sci. USA* 87:6014–18 (1990)). The size and distribution of the exons is well conserved between the two species for both ZP2 and for ZP3 genes.

Figure 6A:
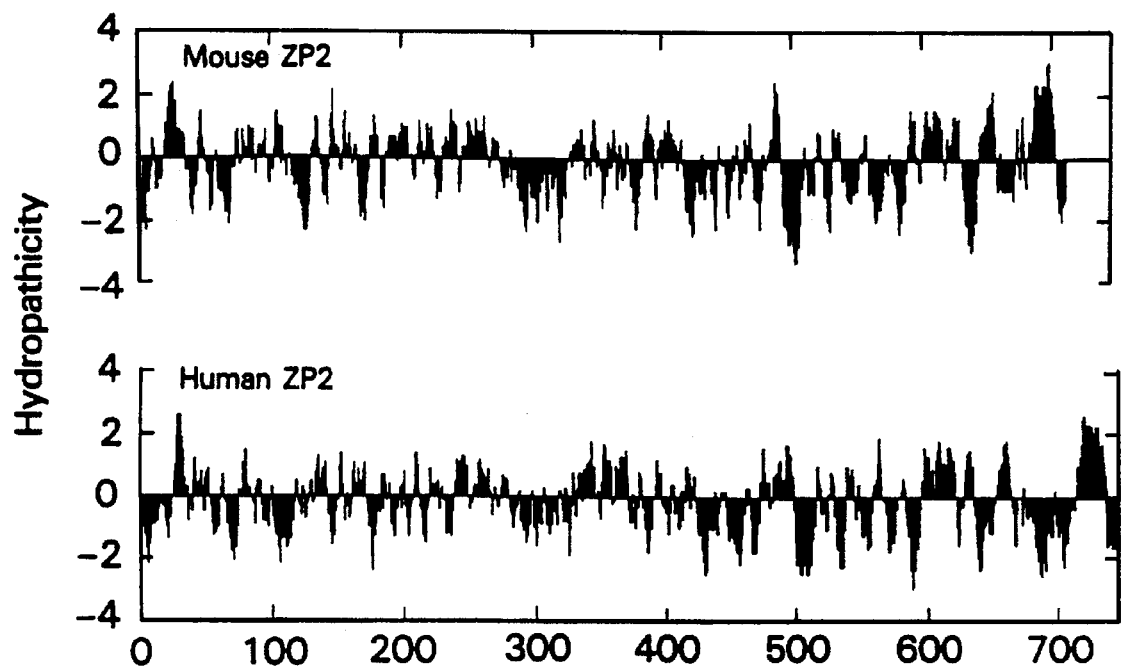
Figure 6B:
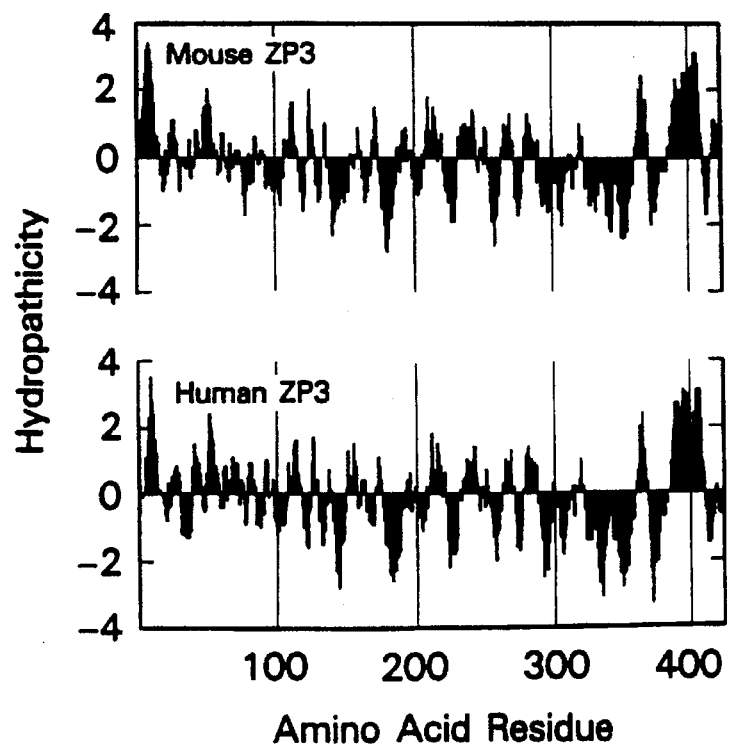

FIG. 6: Comparison of the Secondary Structures of Mouse and Human ZP2 Proteins and of Mouse and Human ZP3 Proteins.

The hydropathicity of the 713 amino acid mouse ZP2 (Liang et al., *Mol. Cell. Biol.* 10: 1507–15 (1990) and 745 amino acid human ZP2 (Liang et al., *Dev. Biol.* 156:399–408 (1993)), determined by the Kyte and Doolittle algorithm (Kyte et al., *J. Mol. Biol.* 157: 105–32 (1982)), indicates the overall similarity of the two proteins. Both have major hydropathic peaks in their signal peptides and near their carboxyl termini. The hydropathicity of the 424 amino acid mouse ZP3

(Ringuette et al., *Dev. Biol.* 127: 287–295 (1988)) and 424 amino acid human ZP3 (Chamberlin et al., 87:6014–18 (1990)), determined by the Kyte and Doolittle algorithm (Kyte et al., supra), indicates the overall similarity of these two proteins. Both have major hydropathic peaks in their signal peptides and near their carboxyl termini.

FIG. 7: The Definition of a Potential Zona Pellucida Peptide for Use as a Contraceptive Vaccine by Screening a ZP3 Epitope Library with a Monoclonal Antibody Specific to ZP3.

(A) Schematic representation of the 1317 nucleotide ZP3 mRNA. The single 1272-nt open reading frame is indicated by an open bar. The lines below the mRNA represent eight positive cDNA clones isolated from the ZP3 epitope library by the monoclonal antibody to ZP3. The clones are aligned on the ZP3 cDNA and the hatched bar indicates the sequence common to all positive clones.

(B) The DNA sequence of the overlapping regions among the eight positive clones and the corresponding amino acid sequence (bold) are shown. The one additional COOH-terminal and eight additional $NH_2$-terminal amino acids shown flanking the epitope were included in the peptide used for immunization.

(C) Hydrophilicity of the deduced 424-amino acid ZP3 protein was plotted with a seven-residue moving average. Horizontal filled-in bars beneath the hydrophilicity indicate amphipathic α helical segments predicted by an 11-residue moving average. The speckled vertical bar represents the 16-amino acid peptide shown in 7B) that was used to immunize experimental animals (Millar et al., *Science* 246:935–38 (1989)).

Figure 8A:
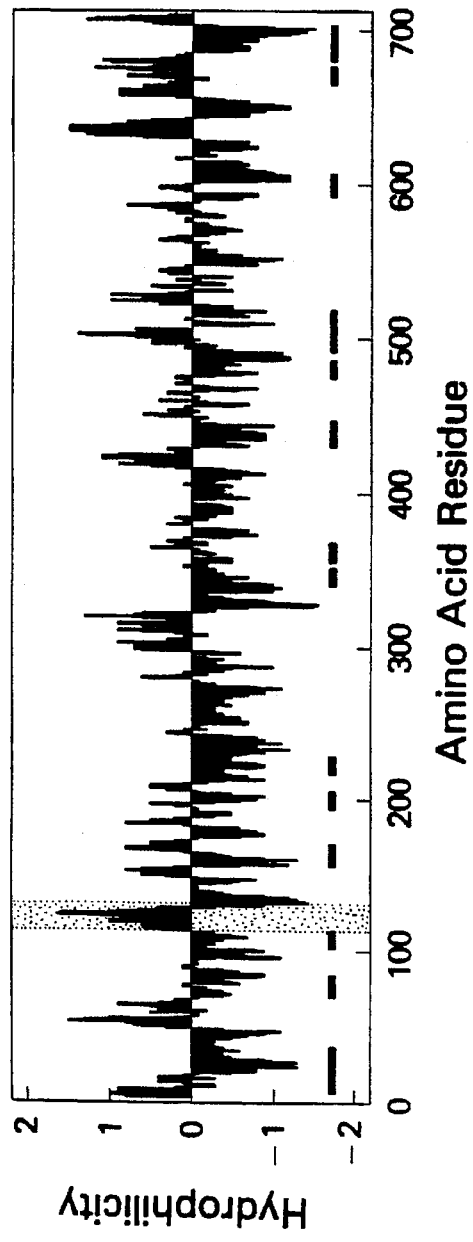
Figure 8B:
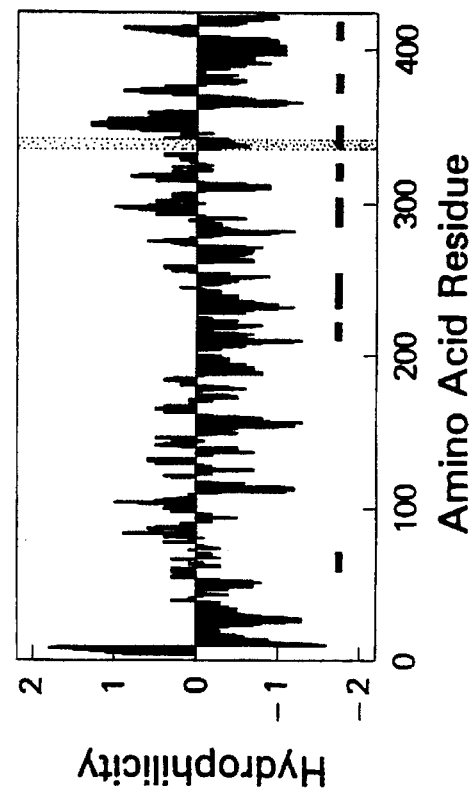

FIG. 8. Localization of Two Monoclonal Antibody Binding Sites on Mouse ZP2 and ZP3.

(A) Hydrophilicity of the 713-amino acid ZP2 protein plotted with a seven-residue moving average. Horizontal filled-in bars beneath the hydrophilicity plot indicate amphipathic α helical segments predicted by an 11-residue moving average. The speckled vertical bar represents the 16-amino acid peptide that is the binding site of a monoclonal antibody specific to mouse ZP2.

(B) Hydrophilicity of the 424-amino acid ZP3 protein plotted with a seven-residue moving average. Horizontal filled-in bars beneath the hydrophilicity plot indicate amphipathic α helical segments predicted by an 11-residue moving average. The speckled vertical bar represents the 7-amino acid peptide that is the binding site of a monoclonal antibody specific to mouse ZP3.

FIG. 9: Alignment of the Mouse ZP3 (SEQ ID NO:11) and ZP2 (SEQ ID NO:12) Epitopes with the Homologous Portions Of the Human ZP2 (SEQ ID NO:13) and ZP3 (SEQ ID NO:14) Proteins.

(A) Mouse ZP3 amino acids 328–343 aligned with human ZP3 amino acids 327–342 (see FIG. 2).

(B) Mouse ZP2 amino acids 114–129 aligned with human ZP2 amino acids 118–133 (see FIG. 4).

DESCRIPTION OF SPECIFIC EMBODIMENTS

The present invention relates in part to DNA segments having sequences that encode mouse and human ZP3 and ZP2 proteins. An embodiment of this aspect of the invention includes cDNA and genomic clones that encode at least a portion of the complete nucleotide sequence of the mouse ZP3 mRNA and the protein encoded thereby which has been described by the present inventor in Example 1, below, and has been published (Ringuette et al., *Dev. Biol.* 127:287–95 (1988); Chamberlin et al., *Dev. Biol.* 131:207–14 (1989)).

A second embodiment of this aspect of the invention includes cDNA and genomic clones that encode at least a portion of the complete nucleotide sequence of the mouse ZP2 mRNA and the protein encoded thereby which has been described by the present inventor in Example 1, below, and has been published (Liang et al., *Mol. Cell. Biol.* 10:1507–15 (1990)).

A third embodiment of this aspect of the invention includes cDNA and genomic clones that encode at least a portion of the complete nucleotide sequence of the human ZP3 mRNA and the protein encoded thereby which has been described by the present inventor in Example 1, below, and has been published (Chamberlin et al., *Proc. Natl. Acad. Sci. USA* 87:6014–18 (1990)).

A fourth embodiment of this aspect of the invention include cDNA and genomic clones that encode at least a portion of the complete nucleotide sequence of the human ZP2 mRNA and the protein encoded thereby which has been described by the present inventor in Example 1, below, and has been published (Liang et al., *Dev. Biol.* 156:399–408 (1993)).

A summary of this information follows:

Genomic Organization and Conservation of the Zona Pellucida Genes: Mouse Zp-2 and Zp-3 are each present in a single copy in the mouse genome and are present on different chromosomes. Zp-2 is located on chromosome 7, 11.3±3.2 cM distal to the Tyr locus and Zp-3 is located on chromosome 5, 9.2±2.9 cM distal to the Gus locus (Lunsford et al., *Genomics* 6:184–87 (1990)). Mouse Zp-2 contains 18 exons that range in size from 45 bp to 190 bp separated by 17 introns (81 bp to 1490 bp) and spans 12.1-kbp of DNA (FIG. 5) (Liang et al., supra (1990)). The 8.6-kbp long mouse Zp-3 gene contains 8 exons ranging in size from 92 bp to 338 bp and has introns whose lengths are between 125 bp and 2320 bp (FIG. 5) (Chamberlin et al., *Dev. Biol.* 131:207–14 (1989)). The intron-exon boundaries of both genes contain consensus splice donor/acceptor sites (Breathnach et al., *Annu. Rev. Biochem.* 50:349–83 (1981)).

The genes encoding ZP2 and ZP3 are conserved among mammals. Taking cross-hybridization of nucleic acid sequences as a criteria, the degree of conservation of Zp-3 is variable with pig and rabbit being less related to mouse than rat, dog, cow and human zona genes (Ringuette et al., *Proc. Natl. Acad. Sci. U.S.A.* 83:4341–45 (1986)). The human homolog of Zp-2 and Zp-3 have been isolated using standard genetic engineering approaches well known in the art by virtue of their homology to the previously isolated murine ZP2 and ZP3 cDNAs. The human ZP2 gene is composed of 19 exons (FIG. 5) whose nucleic acid sequence is 70% the same and encodes a 745 amino acid protein that is 60% identical to that of its mouse counterpart (FIG. 4) (Liang et al., *Dev. Biol.* 156:399–408 (1993)). The mouse and human ZP3 genes each contain 8 exons. The coding sequence of the mouse and human genes are 74% the same and each encodes a 424 amino acid peptide that is 67% identical (FIG. 2) (Chamberlin et al., *Proc. Natl. Acad. Sci. U.S.A.* 87:6014–18 (1990)).

ZP2 mRNA and Protein: The structure of mouse ZP2 was deduced from near-full-length cDNA clones and genomic clones containing exon 1. The ZP2 mRNA is 2201 nt long with very short 5' (30 nt) and 3' (32 nt) untranslated regions (FIG. 3). A transcript of approximately 2.4-kbp is observed by Northern blot analysis of oocyte RNA suggesting that ZP2 mRNA contains a poly(A) tail of approximately 200 nt (Liang et al., *Mol. Cell. Biol.* 10:1507–15 (1990)). ZP2 mRNA has a single open reading frame of 2139 nt initiated at an ATG within the ANNATG motif associated with vertebrate initiator codons (Kozak, Cell 44:283–93 (1986); Cavener, *Nucleic Acids Res.* 15:1353–61 (1986)). The open reading frame encodes a polypeptide of 713 amino acids with a molecular weight of 80,217 daltons, the amino acid composition of which is 10.8% acidic, 9.5% basic, 10.2% aromatic and 34.8% hydrophobic.

The first 34 amino acids of the deduced polypeptide are absent from the N-terminal amino acid sequence obtained from SDS-PAGE purified ZP2 protein and presumably represent a signal peptide. The amino acids at the −1 and −3 position from the presumptive signal peptidase cleavage site are Ser and Asn, respectively. The positions of these two amino acids are similar to other eukaryotic signal peptidase cleavage sites (Perlman et al., *J. Mol. Biol.* 167:391–409 (1983)) and are in accordance with the (−3, −1) rule of signal peptidase cleavage sites proposed by von Heijne (Von Heijne, *J. Mol. Biol.* 184:99–105 (1985); Von Heijne, *Nucleic Acids Res.* 14:4683–90 (1986)). The resultant core polypeptide secreted into the extracellular matrix would have a molecular weight of 76,373 daltons. The ZP2 amino acid sequence contains seven possible N-linked glycosylation sites (Asn-X-Ser/Thr), and more than 100 potential O-linked glycosylation sites (Liang et al., supra (1990)).

The human and mouse ZP2 mRNAs and proteins are well conserved. The human ZP2 mRNA contains an open reading frame of 2235 nt that can code for a polypeptide of 82,356 daltons containing 745 amino acids (10.2% acidic, 11.5% basic, 9.4% aromatic and 50.3% hydrophobic). Human and mouse ZP2 amino acid sequences are 60.7% identical. Examination of human ZP2 protein revealed a potential signal peptidase cleavage site which contains-amino acids at the −1 and −3 positions that are in accordance with the (−3, −1) rule proposed by yon Heijne (Von Heijne, *J. Mol. Biol.* 184:99–105 (1985); Von Heijne, *Nucleic Acids Res.* 14:4683–90 (1986)). Cleavage at the presumptive signal peptidase site would give rise to a signal sequence of 38 amino acids (4 residues longer than mouse ZP2) and a resultant protein with a predicted molecular mass of 78,200 daltons. The deduced polypeptide chain contains six potential N-linked glycosylation sites (Asn-X-Ser/Thr), four of which are conserved in the mouse ZP2 polypeptide (FIG. 4). The predicted hydropathicity of the human and mouse ZP2 proteins are quite similar, reflecting both amino acid identity and conservative amino acid substitutions (FIG. 6). The conservation of all 20 cysteine residues in the mature human and mouse proteins suggests that at least some of these residues participate in disulfide bonds important for tertiary structure. An additional exon found in human ZP2 (FIG. 5) encodes a 28 amino acid hydrophilic region (residues 671–698) near the carboxyl terminus.

ZP3 mRNA and Protein: Primer extension studies and S1 nuclease protection assays were used to define the 5' terminus of the mouse ZP3 mRNA. Similar to ZP2 mRNA, the 1317 nt ZP3 mRNA has short 5' (29 nt) and 3' (16 nt) untranslated regions (FIG. 1). The latter is so abbreviated that the TAA termination codon is embedded within the consensus AATAAA polyadenylation signal (Ringuette et al., *Dev. Biol.* 127:287–95 (1988)). It is not clear what the role, if any, that these short untranslated regions play in gene expression nor whether they are important for processing ZP2 and ZP3 transcripts. This short untranslated region is a characteristic of both ZP2 (mouse and human) and ZP3 (mouse and human) mRNAs. The mouse ZP3 mRNA in oocytes is 1.5-kb, indicating that it has a poly(A) tail of 200 nt, and is indistinguishable in size from that of rat and rabbit (Ringuette et al., supra (1988)). Taken together, these data suggest that the overall structure of ZP3 mRNA is conserved among mammals.

The polypeptide deduced from the single open reading frame of mouse ZP3 mRNA is 46,307 daltons consisting of 424 amino acids (9% acidic, 7.3% basic, 7.5% aromatic and 31.4% hydrophobic). The N-terminal amino acid of the secreted glycoprotein is blocked to Edman degradation, but using the sliding window/matrix scoring method of yon Heijne (Von Heijne, supra (1985); Von Heijne, supra (1986)), a potential signal peptide of 22 amino acid has been identified (Ringuette et al., supra (1988)). The resultant secreted protein would have a molecular weight of 43,943 daltons, consistent with the reported 44,000 dalton ZP3 core protein (Bleil et al., *Dev. Biol.* 76:185–202 (1983)).

The human and mouse ZP3 mRNAs and proteins are well conserved. The human ZP3 mRNA contains an open reading frame of 1272 nt that can code for a polypeptide of 47,032 daltons containing 424 amino acids (12% acidic, 8% basic, 7% aromatic and 32% hydrophobic). Human and mouse ZP3 amino acid sequences are 67% identical. Examination of human ZP3 protein revealed a potential signal peptidase cleavage site which contains amino acids at the −1 and −3 positions that are in accordance with the (−3, −1) rule proposed by von Heijne (Von Heijne, supra (1985); Von Heijne, supra (1986)). Cleavage at the presumptive signal peptidase site would give rise to a signal sequence of 22 amino acids and a resultant protein with a predicted molecular mass of 44,399 daltons. The deduced polypeptide chain contains four potential N-linked glycosylation sites (Asn-X-Ser/Thr), three of which are conserved in the mouse ZP3 polypeptide (FIG. 2). The predicted hydropathicity of the human and mouse ZP3 proteins are quite similar, reflecting both amino acid identity and conservative amino acid substitutions (FIG. 6). The conservation of all 13 cysteine residues in the mature human ZP2 and ZP3 epitopes along with their human homologues are shown in FIG. 9.

In brief, a cDNA encoding ZP3 was randomly fragmented and 200–500 bp fragments were cloned into the expression vector λgt11. This epitope library was screened with the aforementioned anti-ZP3 contraceptive monoclonal antibody and the positive clones were used to map a seven amino acid epitope (amino acids 336–342) on mouse ZP3 recognized by the antibody. The homologous region on human ZP3 is contained in amino acids 335–341.

In a similar fashion, a cDNA encoding ZP2 was randomly fragmented to create a second epitope library which was screened with the aforementioned anti-ZP2 contraceptive monoclonal antibody. Positive clones were used to define a 16 amino acid epitope (amino acids 114–129) on mouse ZP2 recognized by the antibody. The homologous region on human ZP2 is contained in amino acids 118–133.

Of course, it must be noted that a shorter portion of the 7 amino acid sequence that displays the ZP3 epitope or the 16 amino acid sequence that displays the ZP2 epitope might also be an effective peptide for purposes of the present invention. Furthermore, certain analogues (e.g., those sequences with ends that are chemically modified to neutralize charges) might provide effective peptides for the practice of the present invention.

Female mice were immunized with a synthetic peptide containing the ZP3 epitope, as described in Example 4, and the resultant circulating anti-ZP3 antibodies bound to the oocytes of immunized animals producing long-lasting contraception. As evidence that the effectiveness of alloimmunization with a zona pellucida peptide is not limited to the ZP3 protein, additional female and mouse proteins suggests that at least some of these residues participate in disulfide bonds important for tertiary structure.

Conservation of Zona Protein Structure: The data in FIGS. 2, 4, 5, and 6 clearly show the high homology of the mouse and human ZP3 and ZP2 sequences, as would be expected from the extensive nucleic acid hybridization observed between mouse ZP3 cDNA and genomic DNAs from a variety of other mammalian species (see Example 2). From this structural homology data, and further standard analyses thereof (e.g., predictions of secondary structure, hydropathicity, or surface accessibility), it would be apparent to one of average skill in the art of protein structure and immunology that the mouse and human ZP3 proteins must also exhibit throughout their entire sequences, an extremely high level of functional homology with respect to locations that are able to induce and bind contraceptive antibodies. Thus, although epitopes for contraceptive antibodies on each protein may comprise short amino acid sequences which are not precisely conserved between the two proteins, the human sequences corresponding to such epitopes on the mouse protein are also expected to induce functionally homologous antibodies, even though the mouse and human antibodies might only recognize their respective alloantigens.

It will be obvious, of course, to one of ordinary skill in the art of genetic engineering, that the above ZP3 and ZP2 sequences may vary slightly (i.e., be mutated) from one inbred mouse strain to another, or from one individual in an outbred population (e.g., one human being) to another, without materially affecting the immunological character of the corresponding zona pellucida protein and, therefore, without departing from the scope of the DNAs of the present invention as conveyed, for example, by the use of the terms "the mouse ZP3 protein" or "the human ZP3 protein" or "the mouse ZP2 protein" or "the human ZP2 protein".

The DNA segments of the present invention variously enable development of different embodiments of the main aspect of the present invention, namely contraceptive vaccines for use in a mammalian female comprising a polypeptide which includes an amino acid sequence that is selected to display at least one epitope for binding of an antibody that inhibits fertilization of an oocyte by a sperm. This contraceptive antibody epitope is an epitope for which there is a functional homolog displayed on a zona pellucida protein that originates from the species in which the vaccine is used. The zona pellucida protein displaying the functionally homologous epitope advantageously is either a ZP3 protein or a ZP2 protein or a ZP1 protein.

A principal embodiment of this aspect of this invention are two contraceptive antibody epitopes that are displayed either on the mouse ZP3 or the mouse ZP2 protein. Synthetic peptides containing either of these epitopes, when coupled to a carrier protein, for example, KLH, will elicit antibodies after alloimmunizations that react with the zona pellucida. FIG. 7 outlines the definition of the mouse ZP3 epitope for a contraceptive antibody, which is described in further detail in Example 3, below. A similar strategy was employed to define the mouse ZP2 epitope for a second contraceptive antibody. The mice were immunized with a synthetic peptide containing the ZP2 epitope, as described in Example 4. This vaccination also elicited antibodies that bound to the zona pellucida proteins.

The reversibility of the contraceptive effect, described in Example 4, can be accounted for by resting oocytes entering into the growth phase and synthesizing a zona pellucida in the presence of low-levels of circulating anti-zona antibodies which appear to decline after immunization with the vaccine is terminated. When ovulated, these oocytes would be coated lightly, if at all, with anti-zona antibodies and would, therefore, be capable of being fertilized.

Studies have demonstrated that repeated immunization of female mice with a mouse ZP3 peptide-KLH conjugate results in long-term infertility in the majority of cases. The production of anti-zona pellucida antibodies occurs despite the fact that the zona peptide is a self antigen (alloantigen). Immune tolerance has been postulated to occur in the neonatal period of development and involves both the functional inactivation of B cells and the deletion of T cells which recognize self antigens. The lack of detectable zona proteins in the ovary until 2–3 days after birth, or their inaccessibility to the developing immune system, may account for the continued presence of lymphocytes capable of recognizing at least one ZP3 epitope.

In regard to the eventual reversibility of the contraceptive immunization, it is curious that having mounted an immunological response against the ZP3 peptide-KLH conjugate, the immune system does not continue to be stimulated by the endogenous ZP3 protein. The following hypotheses may account for this phenomenon in whole or in part, and, therefore, aid in understanding the present invention; but these theoretical explanations should not be construed to limit the scope of the present invention in any way. Nevertheless, it may be speculated that one or more of the following may be involved in the reversibility of the contraceptive immunization: 1) The localization of the zona proteins uniquely to the ovary coupled with the lack of capillaries beyond the basement membrane surrounding the follicles, may physically preclude lymphocytes from interacting with and being stimulated by the zona pellucida; 2) The 16 amino acid ZP3 peptide portion of the immunogen provides a B-cell epitope but may not contain T-cell epitopes (which may, instead, be provided by the KLH moiety) to stimulate helper T-cell functions. Thus, the endogenous ZP3 protein, although containing the same ZP3 peptide, would not contain the T-cell epitopes of the carrier protein that, according to this hypothesis, could be important for mounting an anti-ZP3 peptide response; 3) The ovary may be part of an immunologically protected region and mechanisms that suppress the immunological rejection of the embryo (which contains paternal and, thus, foreign antigens) also function in the ovary.

It is particularly important to note that immunization with the ZP3 peptide vaccine did not result in either structural or functional abnormalities of the mouse ovary (viz normal histology and the ability of vaccinated females to subsequently have litters). In this regard, of course, the use of a synthetic ZP3 peptide as a vaccine precludes any possible minor contamination with other ovarian immunogens. In addition, the physical barrier of the follicular basement membrane and the extra-cellular site of the zona protein may contribute to the absence of an immunocytotoxic response in the ovary. It should be noted that a nearby, partially overlapping T cell epitope is able to elicit an inflammatory response in some but not other inbred strains of mice known to be susceptible to autoimmune oophoritis (Rhim et al., *J. Clin. Invest.* 89: 28–35 (1992)). The potential to elicit an antibody response in the absence of an ovarian inflammatory response may be an additional advantage of this invention (Millar et al., Targeting of zona pellucida for immunocontraception, in *Immunology of Reproduction*, Naz, R. K. (ed) pp. 293–313 (1993)).

The mouse ZP3 epitope recognized by the monoclonal antibody used to develop this vaccine is not detected immunologically in hamster, guinea pig, cat or dog ovaries. Thus, this ZP3 peptide would not be expected to act as a contraceptive in other mammalian species, including human beings, although the ability of this antibody to bind to the human ZP3 protein has not been tested. However, the strategy of the present invention of using vaccination with "self" zona peptides can be applied to other species by taking advantage of the highly conserved nature of the zona genes among mammals. As noted above, the human homologues of the mouse ZP3 and ZP2 genes have been characterized, and the high degree of structural homology is one indication of comparable functional homology in relation to epitopes for contraceptive antibodies.

Accordingly, using the deduced primary amino acid sequence of the human ZP3 and ZP2 proteins, by the practice of the present invention without undue experimentation, it is believed that one of ordinary skill in the art of polypeptide structure and immunology can identify in the human or other mammalian ZP3 and ZP2 proteins the region homologous to the mouse ZP3 and ZP2 peptides described herein. Alternatively, one of such skill may use computer algorithms to predict additional epitopes which may be potential immunogens (T. P. Hopp and K. R. Woods, *Proc. Natl. Acad. Sci. USA* 78:3824 (1981); H. Maragalit, et al. *J. Immunol.* 138:2213 (1987); J. B. Rothbard and W. R. Taylor, *EMBO J.* 7:93 (1988)), or test a large array of peptides representative of the polypeptide chain for epitopes of contraceptive antibodies using well known methods (H. M. Geysen et al. *Proc. Natl. Acad. Sci. USA* 81:3998 (1984); R. A. Houghten, *Proc. Natl. Acad. Sci. USA* 82:5131 (1985); H. M. Geysen, et al. *Science* 235:1184 (1987); E. Norrby, et al. *Proc. Natl. Acad. Sci. USA* 84:6572 (1987)).

Further, as noted previously, one skilled in the art of synthetic peptide vaccines can also develop "mimotopes" of epitopes to available contraceptive antibodies. According to this approach, first, the ability of any desired antibody to bind to essentially every possible sequence of two amino acids that naturally appear in proteins is tested. Upon identification of a pair of amino acids with detectable binding of the antibody, the sequence surrounding those two amino acids is progressively and systematically varied, by the inclusion of each of the naturally occurring amino acids as well as some amino acids not found in natural proteins, until continued testing of antibody binding identifies a short peptide displaying an epitope with sufficient affinity for the selected antibody to be used for the desired purpose.

Thus, the approach of this invention of alloimmunization with epitopes of zona proteins is expected to have wide application in the design of future contraceptive vaccines for the control of mammalian populations.

The present invention can be illustrated by the use of the following non-limiting examples.

EXAMPLE 1

Determination of the Primary Structure of Mouse and Human Zona Pellucida Proteins by Cloning and Characterizing the Mouse and Human ZP3 and ZP2 Genes A cDNA library was made from poly(A)$^+$ RNA isolated from mouse ovaries tissues using techniques standard to the field (Ringuette et al., *Proc. Natl. Acad. Sci. USA* 83:4341–45 (1986)). Eco RI linkers were added to the ends of the cDNAs and the library was cloned into Eco RI site of lambda gt11. The library was packaged and used to infect *E. coli* Y1090 cells which were mixed with agarose and plated in agar-filled petri dishes using standard techniques. The lytic phase was induced by a temperature shift from 37° C. to 42° C. Nitrocellulose filters, impregnated with isopropyl β-D-thiogalactoside, were used to induce expression of β-galactosidase fusion proteins by λgt11 recombinants. Those containing ZP2 or ZP3 epitopes were detected with a rabbit antisera that had been raised against heat solubilized mouse zonae pellucidae. The positive clones were plaque purified and tested for their ability to express fusion proteins that reacted with rat monoclonal antibodies specific to either ZP2 or ZP3. Two λgt11 recombinants reacted with a monoclonal antibody specific to ZP3 (Ringuette et al., supra (1986); Ringuette et al., *Dev. Biol.* 127:287–95 (1988)) and one λgt11 recombinant reacted with a monoclonal antibody specific to ZP2 (Liang et al., *Mol. Cell. Biol.* 10:1507–15 (1990)).

Mouse ZP3: The cDNA insert from a single λgt11 clone was subcloned (pZP3.1) and used to rescreen the library to obtain additional cDNAs. The 5' most 46 nt were determined from a genomic clone and the transcription initiation site was determined by procedures standard to the field (Ringuette et al., supra (1988)). These sequences were used to determine the structure of the mouse ZP3 mRNA and the resultant protein. The ZP3 mRNA is a 1317 nt polyadenylated transcript that contains a single open reading frame encoding a 424 amino acid polypeptide chain with a predicted mass of 46,307 Da. The identity of the cDNA clone was confirmed by comparison of its deduced amino acid sequence with that of a 20 amino acid sequence obtained from an internal peptide of purified ZP3 protein. A predicted signal peptidase cut site after amino acid 17 would result in a polypeptide with a mass of 43,943 Da (Ringuette et al., supra 1988). The 83,000 Da mass of the native, secreted ZP3 sulfated glycoprotein reflects post-translational modifications of the polypeptide chain. Additional characteristics of this protein have been noted above.

Mouse ZP2: The cDNA insert from a single λgt11 clone was subcloned (pZP2.1) and used to rescreen the library to obtain additional cDNAs that contained sequences that encoded the entire polypeptide chain (Liang et al., *Mol. Cell. Biol.* 10:1507–15 (1990)). The 5' most 21 nt were determined from a genomic clone, and the transcription initiation site was determined by procedures standard to the field. These sequences were used to determine the structure of the mouse ZP2 mRNA and the resultant protein. The ZP3 mRNA is a 2201 nt polyadenylated transcript that contains a single open reading frame encoding a 713 amino acid polypeptide chain with a predicted mass of 80,217 Da. The identity of the clone was confirmed by comparison of its deduced amino acid sequence with that of a 16 amino acid sequence from a N-terminal peptide and with that of a 10 amino acid sequence obtained from an internal peptide of purified ZP2 protein. The first 34 amino acids represent a signal peptide, the cleavage of which would result in a polypeptide with a mass of 76,373 Da (Liang et al., supra (1990)). The 120–140,000 Da mass of the native, secreted ZP2 sulfated glycoprotein reflects post-translational modifications of the polypeptide chain.

EXAMPLE 2

Conservation of the Zona Pellucida Genes Among Mammals, Specifically Mouse and Human Mouse Zp-3 genomic clones were isolated from a λJ1 library containing mouse B10A genomic DNA inserts by screening with mouse ZP3 cDNA (Chamberlin et al., *Dev. Biol.* 131:207–14 (1989)). Characterization of two overlapping clones revealed that the single copy Zp-3 gene contains 8 exons spanning 8.6-kbp. Exon sequences confirmed the previously described coding region of the ZP3 mRNA (Ringuette et al., *Dev. Biol.* 127:287-95 (1988); Chamberlin et al., supra (1989)). A mouse Zp-2 genomic clone was isolated from the same λJ1 library by screening with mouse ZP2 cDNA (Liang et al., *Mol. Cell. Biol.* 10:1507-15 (1990)). The single copy Zp-2 gene contains 18 exons spanning 12.1-kbp. Exon sequences confirmed the previously described coding region of the ZP2 mRNA (Liang et al., supra (1990)).

DNA was isolated from seven mammalian species: mouse, rat, rabbit, dog, pig, cow and human. After digestion with a restriction enzyme (e.g., Bam H1) and transfer to a membrane by Southern blotting, the DNAs were probed with mouse ZP3 cDNA using standard techniques. Although stronger hybridization was detected with rat, dog, cow and human than with rabbit and pig DNA, cross-hybridization was detected with DNA from all mammalian species (Ringuette et al., *Proc. Natl. Acad. Sci. USA* 83:4341-45 (1986)). Similar results were obtained using ZP2 cDNA probes. Mouse ZP3 cDNA probes cross-hybridized with rat and rabbit ovarian poly(A)$^+$ RNA on Northern blots and all three species have transcripts of similar size (Ringuette et al., supra (1988)). Taken together, these data suggest that the zona genes are well conserved among mammals. To further substantiate this hypothesis, human ZP2 and human ZP3 genes and their RNA transcripts were isolated and characterized.

Human ZP3: A Charon 4A human genomic library was screened with mouse ZP3 cDNA under low stringency to allow cross-hybridization with the heterologous probe (Chamberlin et al., *Proc. Natl. Acad. Sci. USA* 87:6014-18 (1990)). A single recombinant phage was isolated and characterized. This clone contained exons 1-5 of the human ZP3 gene. The remaining 6-8 exons were cloned from genomic DNA using the polymerase chain reaction and oligonucleotide primers from human exons 6 and 8 (determined from human ZP3 cDNA, see below). The human ZP3 genes contains 8 exons, the sizes of which have near identity with those of mouse Zp-3, and the human gene spans approximately 18.3-kbp (Chamberlin et al., supra (1990)).

Poly (A)$^+$ RNA was isolated from a human ovary and used in a RT-PCR reaction (reverse transcription to make a single strand cDNA template, followed by exon specific oligonucleotide primers in the polymerase chain reaction) to construct full-length cDNA clones representative of the human ZP3 transcript) (Chamberlin et al., supra (1990)). The human ZP3 transcript has a single 1272 nt open reading frame, the nucleic acid sequence of which is 74% identical to that of the mouse ZP3 transcript. The human transcript encodes a 424 amino acid polypeptide ZP3 protein with a calculated molecular mass of 47,032 Da that is 67% identical to that of the mouse ZP3 protein. The hydropathicity profiles of the human and mouse ZP3 proteins are remarkably similar and reflect the conserved nature of the allowable amino acid substitutions (Chamberlin et al., supra (1990)). Additional characteristics of this protein have been noted above.

Human ZP2: A Charon 4A human genomic library was screened with mouse ZP2 cDNA under low stringency to allow cross-hybridization with the heterologous probe (Liang et al., *Dev. Biol.* 156: 399-408 (1993)). Three overlapping recombinant phages were isolated and characterized. These clones contained the entire 14.0-kbp human ZP2 locus which is made up of 19 exons. Overall, these coding regions are 70% identical to those of mouse Zp-2. In addition, human ZP2 contains an extra exon of 84 bp (exon 18) that is not found in mouse ZP2 cDNA. Sequence analysis of mouse Zp-2 intron 17 revealed a region of 76 bp that shares a 70% sequence homology with human ZP2 exon 18 (Liang et al., supra (1993)).

Poly (A)$^+$ RNA was isolated from a human ovary and used in a RT-PCR reaction (reverse transcription to make a single strand cDNA template, followed by exon specific oligonucleotide primers in the polymerase chain reaction) to construct cDNA clones representative of the human ZP2 transcript) (Liang et al., supra (1993)). In addition, human ovarian mRNA was used in the construction of an ovarian cDNA library using the Uni-ZAP cDNA library construction system (Stratagene). The library was screened with the aforementioned human ZP2 cDNA probes to isolate additional cDNA clones that, together with those obtained with the RT-PCR, represented near full-length cDNAs. The nucleic acid sequence of these clones revealed that the human ZP2 transcript has a single 2235 nt open reading frame that is 74% identical to that of the mouse ZP2 transcript. The human transcript encodes a 745 amino acid ZP2 protein with a calculated molecular mass of 82,356 Da that is 60.7% identical to that of the mouse ZP2 protein (Liang et al., supra (1993)). The hydropathicity profiles of the human and mouse ZP2 proteins are remarkably similar and reflect the conserved nature of the allowable amino acid substitutions. Additional characteristics of this protein have been noted above.

These two examples demonstrate that the primary amino acid sequence of the zona pellucida proteins (ZP3, ZP2, ZP1) can be deduced from cloned zona genes (cDNAs and/or genomic clones). This data would not otherwise be available because the paucity of biological material makes impossible the direct determination of the zona protein sequences. Furthermore, this example demonstrates that the conservation of the zona genes among mammals permit the zona genes of one species (e.g. mouse) to be used to clone and characterize the zona genes of another species (e.g. human). Cross-hybridization data to genomic DNA from seven mammalian species further indicate that a similar strategy can be used to determine the primary protein structures of the zona proteins from any mammal.

Further, this invention provides cDNA and genomic clones that can be used to express recombinant zona proteins of mouse and human ZP2 and ZP3 in their entirety or in parts thereof. It will be obvious to those in the field that this can be done using a variety of viral or plasmid based vectors in a variety of prokaryotic and eukaryotic cell lines and in the production of transgenic animals. Such recombinant zona proteins may be of use as diagnostic reagents for the assessment of male fertility or lack thereof and for providing sufficient amounts of zona proteins for further biochemical characterization of structure-function correlates of the zona proteins.

EXAMPLE 3

Identification of ZP3 and ZP2 Peptides Capable of Eliciting Antibodies that Bind to the Zona Pellucida Protein in the Same Species Prior to this invention, it had not been demonstrated that a peptide comprised of a portion of a zona protein from a particular species could elicit antibodies in that same species that would bind to the native zona pellucida structure and prevent fertilization. The success of demonstrating the efficacy of this approach is based on two aspects of this invention: the determination of the primary amino acid sequence of the mouse and human ZP2 and ZP3 proteins by cloning the cognate genes (Ringuette et al., *Dev. Biol.* 127:287–95 (1988); Chamberlin et al., *Dev. Biol.* 131:207–14 (1989); Liang et al., *Mol. Cell. Biol.* 10:1507–15 (1990); Chamberlin et al., *Proc. Natl. Acad. Sci. USA* 87:6014–18 (1990); Liang et al., *Dev. Biol.* 156:399–408 (1993)), and the identification of candidate regions on the zona proteins to test the efficacy of this contraceptive strategy. In addition, the determination that the zona pellucida proteins are well conserved between mouse and human indicates that the three-dimensional structures of ZP2 and ZP3 in different mammalian species will have near identity. Thus, regions of the zona proteins identified as potential vaccine candidates in one species (e.g. mouse) will be effective in other species (e.g. humans). These regions need not have identical amino acid sequence but need only be located in the homologous region of the zona pellucida matrix of each particular species.

As indicated above, once the primary amino acid sequence of a protein is known, a variety of strategies can be used to identify candidate peptides for testing as contraceptive vaccines. An example of one strategy is provided in the invention.

The first candidate peptide was identified on mouse ZP3 by screening an epitope expression library derived from a ZP3 cDNA with a monoclonal antibody specific to the ZP3 protein.

A 1.0 kb cDNA known to contain the epitope recognized by the anti-ZP3 monoclonal antibody (Ringuette et al., supra (1986)) was cut into random fragments which were size selected (200 bp) and cloned into the λgt11 expression vector. More specifically, the cDNA insert of pZP3.1 was digested with DNase in the presence of 15 mM $MgCl_2$ and 200 bp size selected fragments (V. Mehra, D. Sweetwer and R. A. Young, *Proc. Natl. Acad. Sci. USA* 83:7013 (1986)) were ligated into Lambda ZAP (Strategene). *E. coli* BB4 cells were infected with the un-amplified epitope library and screened (Ringuette et al., supra (1986)), with an anti-ZP3 monoclonal antibody (East et al., *Dev. Biol.* 109: 268 (1985) ). Positive clones were plaque purified and the sequence of the insert DNA was determined from isolated plasmid DNA (F. Sanger, S. Nicklen, et al., *Proc. Natl. Acad. Sci. USA* 74:5463 (1977)).

A synthetic peptide displaying an epitope for a contraceptive antibody. The nucleic acid sequence of the cDNA inserts from 8 positive clones was determined (FIG. 7A). The 24 nucleotides common to the eight clones code for a seven amino acid peptide which must contain the epitope recognized by the antibody (FIG. 7B). The peptide represents amino acids 336–342 which is immediately adjacent to the most hydrophilic portion of ZP3 (FIG. 7C). A 16 amino acid peptide (ZP3 amino acids 328–343) containing the epitope ($NH_2$-CYS-SER-ASN-SER-SER-SER-SER-GLN-PHE-GLN-ILE-HIS-GLY-PRO-ARG-GLN-COOH) was synthesized (Merrifield, R. B., *J. Amer. Soc.,* 85:2149 (1963)) on a Model 430A, Applied Biosystems Solid Phase Synthesizer, deprotected and released from the phenylacetamidomethyl resin with anhydrous hydrogen fluoride containing 10% anisole and 10% thiophenol at 0° C. for 2 hr. The crude peptide was purified by HPLC on a Vydac C4 Column and conjugated to keyhole limpet hemocyanin by coupling the amino terminal cysteine to KLH through a maleimido linkage (Lerner, R. A. et al., *Proc. Natl. Acad. Sci. USA,* 78:3403 (1981)).

Immunogenicity of the synthetic peptide vaccine. Sixteen NIH random bred Swiss mice were immunized intraperitoneally with 100 λg of the ZP3 peptide-KLH conjugate (1 mg/ml) in an equal volume of complete Freund's adjuvant and then boosted at 10–14 day intervals with 100 λg of conjugated peptide in incomplete Freund's adjuvant. Circulating anti-zona pellucida antibodies were detected using solubilized whole zona in an ELISA. Flexible ELISA plates were coated with purified, acid solubilized zona (J. D. Bleil and P. M. Wassarman, *J. Cell Biol.* 102:1363 (1986)) at 100 ng per well, blocked with 1% bovine serum albumin in Tris HCl, pH 7.5, 0.15M NaCl (TBS), and incubated with sera diluted 1:104 in the same. The plates were washed several times with TBS/1% Tween-20, incubated with horse radish peroxidase (HRP) conjugated goat anti-mouse antibody, washed as before, and developed using a Horseradish Peroxidase Substrate Kit (Bio-Rad). The response was quantified by measuring absorbance at 414 nm.

A plateau level of the average response was reached after five immunizations. It should be noted that there was variation of the amount of circulating anti-zona pellucida antibodies among the animals with the difference between the high and low responders being almost six-fold. Control animals were immunized with KLH alone using an identical regimen and had no detectable circulating anti-zona antibodies.

The reactivity of sera from immunized animals with individual zona proteins was analyzed using Western blots of purified zonae separated by SDS-PAGE. Isolated mouse zona were acid solubilized and separated by SDS-PAGE using 10% acrylamide (U. K. Laemmli, *Nature* 227:680 (1970)). Proteins were transferred to nitrocellulose (W. N. Burnette, *Analyt. Biochem.* 112:195 (1980)) and the filters soaked in TBS/1% BSA. Sera or antibodies were diluted in TBS/1% BSA/0.1% Tween and individual lanes were probed with: pre-immune sera diluted 1:50; immune sera from KLH immunized mice diluted 1:50; immune sera from ZP3 peptide-KLH immunized mice diluted 1:50; rat anti-mouse ZP3 monoclonal antibody (East et al., *Dev. Biol.* 109:268–73 (1985)) diluted 1:50; and rabbit anti-mouse zona pellucida polyclonal antisera (East et al., supra (1985)) diluted 1:50. Filters were washed in TBS/0.1% Tween and incubated with HRP-labeled second antibody of the appropriate specificity (Jackson Immunoresearch) diluted 1:1000 in TBS/BSA/Tween. Nitrocellulose-bound antibodies were visualized using 4-chloro-1-naphthol.

Sera from animals immunized with the ZP3 peptide-KLH conjugate reacted with a single zona protein which co-migrated with ZP3. No reaction with any of the zona proteins was detected with pre-immune or control sera.

To determine whether anti-peptide antibodies recognize zona in its native state as well as in acid-solubilized and SDS-denatured preparations, sera from experimental and control animals were used to stain unfixed frozen sections of mouse ovary. Ovaries were removed and immediately frozen in Tissue-Tek O.C.T. Compound (Lab-Tek Products) on dry ice. Five µm sections were mounted on gelatin coated slides, treated with 1% BSA in PBS for 15 min at 20° C. and rinsed in PBS. Sections were treated for one hour with undiluted serum from immunized mice, rinsed in PBS and stained for 30 min at 20° C. with FITC-conjugated goat anti-mouse IgG (Jackson ImunoResearch Laboratories) diluted 1:50 in PBS/BSA. Sections were rinsed with PBS, mounted in Fluormount-S (FisherBiotech) and photographed using Ektachrome 200 film.

Using a fluorescein-conjugated second antibody, mouse antibodies from experimental mice were detected binding to the zonae surrounding developing oocytes, indicating that the circulating anti-zona antibodies are capable of binding native ZP3 protein. There was no detectable fluorescence of sections stained with sera from control mice.

As evidence that alloimmunization with a zona pellucida peptide is not limited to the ZP3 protein, a second candidate peptide was identified on mouse ZP2 by screening an epitope expression library derived from a ZP2 cDNA with a monoclonal antibody specific to the ZP2 protein using the techniques described above. Specifically, a 0.9-kbp cDNA (pZP2.1) known to contain the epitope recognized by an anti-ZP2 monoclonal antibody (Liang et al., *Mol. Cell. Biol.* 10:1507–15 (1990)) was digested with DNAse to create random fragments that were cloned into Lambda ZAP (Stratagene) to create an expression epitope library. The library was screened with the monoclonal antibody specific to mouse ZP2 and the nucleic acid sequence of positive clones was determined. The 54 bp common to the positive clones must encode the epitope recognized by the antibody. The peptide represents amino acids 114–129 which are coincident with the major hydrophilic portion of ZP2 (FIG. 8).

The 17 amino acid peptide (ZP2 amino acids 114–129) containing the epitope ($NH_2$-Ile-Arg-Val-Gly-Asp-Thr-Thr-Thr-Asp-Val-Arg-Tyr-Lys-Asp-Asp-Met-COOH) was synthesized by Merrifield solid phase synthesis (see above) with an N-terminal cysteine with which it was coupled to keyhole limpet hemocyanin. Female mice immunized intraperitoneally with 100 λg of the ZP3 peptide-KLH conjugate (1 mg/ml) in equal volume of complete Freund's adjuvant and then boosted at 10–14 day intervals with 100 λg of conjugated peptide in incomplete Freund's adjuvant. Circulating anti-zona antibodies were detected in an ELISA as described above. After 6 immunizations, four of five female mice developed anti-zona antibodies at titers comparable to those immunized with the ZP3 peptide. These data demonstrate the ability to the ZP2 peptide to elicit antibodies that cross-react with zona pellucida from the same species

EXAMPLE 4

A Contraceptive Vaccine Comprising a Synthetic Peptide with a ZP3 Epitope

To determine if the circulating anti-ZP3 antibodies were of sufficient titer to bind to the zonae surrounding growing oocytes of the experimental mice, plastic embedded sections of ovaries isolated from four females immunized with ZP3-KLH conjugate were stained with horse radish peroxidase (HRP) conjugated anti-mouse antibody. Dissected ovaries were fixed for one hour in 1% glutaraldehyde, rinsed in PBS and embedded in JB4 plastic. Endogenous antibody was detected in 4 μm sections using an anti-mouse streptavidin-HRP kit (Zymed).

Mouse anti-zona pellucida antibodies were observed coating the zonae of the oocytes in the sections examined. There were no detectable anti-zona antibodies in ovaries isolated from four control (KLH alone injected) mice. The ovarian sections of both the treated and control animals contained only normal follicles and cell types with no evidence of inflammation or cellular cytotoxicity. The antisera of the ZP3-KLH immunized animals did not react with other mouse tissue including brain, liver, spleen, kidney, heart, lung, intestine, testis or muscle (data not shown) which indicates that immunization with the peptide conjugate elicits a response that is specific for the zona pellucida.

Effectiveness of the synthetic peptide vaccine for contraception. The fertility of the remaining 12 experimental and 12 control mice was tested by mating them continuously with proven males. Two weeks after the last immunization, proven males were individually and continuously caged with experimental and control mice at a ratio of 1:1. The percentage of animals having given birth to a litter versus the duration of continuous mating was compared for animals injected with ZP3 peptide-KLH and KLH alone. The titer of anti-ZP antibodies of three groups of ZP3 peptide-KLH immunized mice at the beginning of the mating period were averaged and, in order of increasing average titers, were as follows: group 1, gave birth within 1 month (3 animals); group 2, gave birth between 4 and 7 months (3 animals); and group 3, did not give birth to litters within the 9 month study (6 animals).

In summary, all of the control (KLH alone injected) mice gave birth to litters within three and a half weeks of the introduction of males. Three of the experimental, ZP3 peptide-KLH injected mice also gave birth within this period. These mice were among those that had the lowest titers (<0.2 $A_{414}$ units) of anti-zona antibodies prior to mating. In the remainder of the experimental mice, a contraceptive effect was observed that lasted between 16 and 36 weeks at which time the study was terminated. Three of these animals gave birth to litters after 16 to 24 weeks and had intermediate anti-zona antibody titers. The remaining animals which remained infertile for the duration of the study had the highest initial titers and even 9 months after the last immunization had detectable circulating anti-zona antibodies.

The litter sizes of the ZP3-KLH treated animals which eventually became fertile ranged from 1–5 pups (average 2.8) whereas those treated with KLH alone had litters of 1–9 pups (average 5.2). Both groups had fewer than the normal 7–14 pups (average 10) which may be due, in part, to the adverse effects of intra-peritoneal administration of Freund's adjuvant on fecundity. In addition, the smaller litters of the KLH-ZP3 treated animals could be accounted for by the observed persistent low levels of circulating anti-zona antibodies some of which were detected binding to the zonae surrounding their intra-ovarian oocytes. Despite the presence of these low levels of anti-zona antibodies, these animals, when re-mated, gave birth to litters within three and a half weeks.

The foregoing invention has been described in some detail for purposes of clarity and understanding. It will also be obvious that various combinations in form and detail can be made without departing from the scope of the invention.

What is claimed is:

1. The contraceptive vaccine for use in a mammalian female comprising an amino acid sequence for binding of an antibody that inhibits fertilization of an egg by a sperm, said amino acid sequence comprising a peptide consisting of mouse zona pellucida 3 (ZP3) amino acid sequence Cys-Ser-Asn-Ser-Ser-Ser-Ser-Gln-Phe-Gln-Ile-His-Gly-Pro-Arg-Gln (amino acid residues 328 to 343 of SEQ. ID No. 2) and conservatively modified variants thereof;

or a homologous region of a ZP3 protein originating from a mammalian species which said vaccine is used and conservatively modified variants of said homologous region; and a pharmacologically acceptable vehicle.

2. The contraceptive vaccine of claim 1 wherein said homologous region is Cys-Gly-Thr-Pro-Ser-His-Ser-Arg-Arg-Gln-Pro-His-Val-Met-Ser-Gln and said sequence is derived from a human ZP3 protein.

3. The contraceptive vaccine according to claim 1, wherein said mammalian female in which said vaccine is used is selected from the group consisting of:

a cat, a dog, a pig, a cow, and a human.

4. The contraceptive vaccine according to claim 1, further comprising an effective amount of an adjuvant.

5. A contraceptive vaccine for use in a mammalian female comprising an amino acid sequence for binding of an antibody that inhibits fertilization of an egg by a sperm, said amino acid sequence comprising a synthetic peptide consisting of mouse zona pellucida 3 (ZP3) amino acid sequence Cys-Ser-Asn-Ser-Ser-Ser-Ser-Gln-Phe-Gln-Ile-His-Gly-Pro-Arg-Gln (amino acid residues 328 to 343 of SEQ. ID No. 2) and conservatively modified variants thereof;

or a synthetic peptide derived from a homologous region of a ZP3 protein originating from a mammalian species which said vaccine is used and conservatively modified variants of said homologous region; and a pharmacologically acceptable vehicle.

6. The contraceptive vaccine of claim 5 wherein said homologous region is Cys-Gly-Thr-Pro-Ser-His-Ser-Arg-Arg-Gln-Pro-His-Val-Met-Ser-Gln and said sequence is derived from a human ZP3 protein.

\* \* \* \* \*

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
    ( A ) LENGTH: 1317 base pairs
    ( B ) TYPE: nucleic acid
    ( C ) STRANDEDNESS: both
    ( D ) TOPOLOGY: linear ( i i ) MOLECULE TYPE: cDNA ( x i ) SEQUENCE DESCRIPTION: SEQ ID NO:1:

```
CTGAGCCCAG CTGTACTCCA GGCGGGACCA TGGCGTCAAG CTATTTCCTC TTCCTTTGTC      60
TCCTGCTGTG TGGAGGCCCC GAGCTGTGCA ATTCCAGAC  TCTGTGGCTT TTGCCGGGTG     120
GAACTCCCAC CCCAGTGGGG TCCTCATCAC CTGTGAAGGT GGAGTGTCTG AAGCTGAAC      180
TAGTGGTGAC TGTCAGTAGA GACCTTTTTG GCACGGGGAA GCTGGTGCAG CCCGGGGACC     240
TCACCCTTGG CTCAGAGGGT TGTCAGCCCC GGGTGTCCTT GGATACCGAC GTGGTCAGGT     300
TCAACGCCCA GTTGCACGAG TGCAGCAGCA GGGTGCAGAT GACGAAAGAT GCCCTGGTGT     360
ACAGCACCTT CCTACTCCAC GACCCTCGCC CTGTGAGTGG CCTGTCCATC CTCAGGACTA     420
ACCGTGTGGA GGTACCCATT GAGTGCCGAT ACCCCAGGCA GGGCAATGTG AGCAGCCACC     480
CTATCCAGCC CACCTGGGTT CCCTTCAGAG CCACTGTGTC CTCAGAGGAG AAACTGGCTT     540
TCTCTCTTCG CCTGATGGAG GAGAACTGGA ATACTGAGAA ATCGGCTCCC ACCTTCCACC     600
TGGGAGAGGT AGCCCACCTC CAGGCAGAAG TCCAGACTGG AAGCCACCTG CCGCTGCAGC     660
TGTTTGTGGA CCACTGCGTG GCCACGCCTT CACCTTTGCC AGACCCGAAC TCCTCCCCCT     720
ATCACTTCAT CGTGGACTTC CACGGTTGCC TTGTGGATGG TCTATCTGAG AGCTTTTCGG     780
CATTTCAAGT CCCCAGACCC CGGCCAGAGA CTCTCCAGTT CACGGTGGAT GTATTCCATT     840
TTGCCAACAG CTCCAGAAAT ACGCTCTACA TCACCTGCCA TCTCAAAGTC GCGCCAGCTA     900
ACCAGATCCC CGATAAGCTC AACAAAGCCT GTTCGTTCAA CAAGACTTCC CAGAGTTGGT     960
TGCCAGTAGA GGGTGATGCT GACATCTGTG ATTGCTGCAG CCATGGCAAC TGTAGTAATT    1020
CAAGCTCTTC ACAGTTCCAG ATCCATGGAC CCCGCCAGTG GTCCAAGCTA GTTTCTCGAA    1080
ACCGCAGGCA CGTGACCGAT GAAGCTGATG TCACTGTAGG GCCCCTGATA TTCCTTGGAA    1140
AGGCCAACGA CCAGACTGTG GAAGGCTGGA CTGCTTCTGC TCAAACCTCT GTGGCTCTTG    1200
GGTTAGGCCT GGCCACAGTG GCATTCCTGA CCCTGGCAGC TATAGTCCTT GCTGTCACCA    1260
GGAAGTGTCA CTCCTCTTCC TACCTTGTAT CCCTTCCGCA ATAAAGAAG  AAACTCA       1317
```

( 2 ) INFORMATION FOR SEQ ID NO:2:

( i ) SEQUENCE CHARACTERISTICS:
    ( A ) LENGTH: 424 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:2:

```
Met Ala Ser Ser Tyr Phe Leu Phe Leu Cys Leu Leu Leu Cys Gly Gly
 1               5                  10                  15
Pro Glu Leu Cys Asn Ser Gln Thr Leu Trp Leu Leu Pro Gly Gly Thr
                20                  25                  30
Pro Thr Pro Val Gly Ser Ser Ser Pro Val Lys Val Glu Cys Leu Glu
            35                  40                  45
Ala Glu Leu Val Val Thr Val Ser Arg Asp Leu Phe Gly Thr Gly Lys
        50                  55                  60
```

| | | | | | | | | | | | | | | | |
|---|---|---|---|---|---|---|---|---|---|---|---|---|---|---|---|
|Leu|Val|Gln|Pro|Gly|Asp|Leu|Thr|Leu|Gly|Ser|Glu|Gly|Cys|Gln|Pro|
|65| | | |70| | | |75| | | |80| | | |
|Arg|Val|Ser|Val|Asp|Thr|Asp|Val|Val|Arg|Phe|Asn|Ala|Gln|Leu|His|
| | | | |85| | | |90| | | |95| | | |
|Glu|Cys|Ser|Ser|Arg|Val|Gln|Met|Thr|Lys|Asp|Ala|Leu|Val|Tyr|Ser|
| | | |100| | | |105| | | |110| | | | |
|Thr|Phe|Leu|Leu|His|Asp|Pro|Arg|Pro|Val|Ser|Gly|Leu|Ser|Ile|Leu|
| | |115| | | |120| | | | |125| | | | |
|Arg|Thr|Asn|Arg|Val|Glu|Val|Pro|Ile|Glu|Cys|Arg|Tyr|Pro|Arg|Gln|
| |130| | | |135| | | | |140| | | | | |
|Gly|Asn|Val|Ser|Ser|His|Pro|Ile|Gln|Pro|Thr|Trp|Val|Pro|Phe|Arg|
|145| | | |150| | | | |155| | | | |160| |
|Ala|Thr|Val|Ser|Ser|Glu|Glu|Lys|Leu|Ala|Phe|Ser|Leu|Arg|Leu|Met|
| | | |165| | | | |170| | | |175| | | |
|Glu|Glu|Asn|Trp|Asn|Thr|Glu|Lys|Ser|Ala|Pro|Thr|Phe|His|Leu|Gly|
| | | |180| | | | |185| | | |190| | | |
|Glu|Val|Ala|His|Leu|Gln|Ala|Glu|Val|Gln|Thr|Gly|Ser|His|Leu|Pro|
| |195| | | | |200| | | | |205| | | | |
|Leu|Gln|Leu|Phe|Val|Asp|His|Cys|Val|Ala|Thr|Pro|Ser|Pro|Leu|Pro|
| |210| | | | |215| | | | |220| | | | |
|Asp|Pro|Asn|Ser|Ser|Pro|Tyr|His|Phe|Ile|Val|Asp|Phe|His|Gly|Cys|
|225| | | |230| | | | |235| | | | | |240|
|Leu|Val|Asp|Gly|Leu|Ser|Glu|Ser|Phe|Ser|Ala|Phe|Gln|Val|Pro|Arg|
| | | |245| | | | |250| | | | |255| | |
|Pro|Arg|Pro|Glu|Thr|Leu|Gln|Phe|Thr|Val|Asp|Val|Phe|His|Phe|Ala|
| | |260| | | | |265| | | | |270| | | |
|Asn|Ser|Ser|Arg|Asn|Thr|Leu|Tyr|Ile|Thr|Cys|His|Leu|Lys|Val|Ala|
| |275| | | | |280| | | | |285| | | | |
|Pro|Ala|Asn|Gln|Ile|Pro|Asp|Lys|Leu|Asn|Lys|Ala|Cys|Ser|Phe|Asn|
|290| | | |295| | | | |300| | | | | | |
|Lys|Thr|Ser|Gln|Ser|Trp|Leu|Pro|Val|Glu|Gly|Asp|Ala|Asp|Ile|Cys|
|305| | | |310| | | | |315| | | | | |320|
|Asp|Cys|Cys|Ser|His|Gly|Asn|Cys|Ser|Asn|Ser|Ser|Ser|Ser|Gln|Phe|
| | | |325| | | | |330| | | | |335| | |
|Gln|Ile|His|Gly|Pro|Arg|Gln|Trp|Ser|Lys|Leu|Val|Ser|Arg|Asn|Arg|
| | |340| | | | |345| | | | |350| | | |
|Arg|His|Val|Thr|Asp|Glu|Ala|Asp|Val|Thr|Val|Gly|Pro|Leu|Ile|Phe|
| | |355| | | | |360| | | | |365| | | |
|Leu|Gly|Lys|Ala|Asn|Asp|Gln|Thr|Val|Glu|Gly|Trp|Thr|Ala|Ser|Ala|
| |370| | | | |375| | | | |380| | | | |
|Gln|Thr|Ser|Val|Ala|Leu|Gly|Leu|Gly|Leu|Ala|Thr|Val|Ala|Phe|Leu|
|385| | | | |390| | | | |395| | | | |400|
|Thr|Leu|Ala|Ala|Ile|Val|Leu|Ala|Val|Thr|Arg|Lys|Cys|His|Ser|Ser|
| | | | |405| | | | |410| | | | |415| |
|Ser|Tyr|Leu|Val|Ser|Leu|Pro|Gln| | | | | | | | |
| | | |420| | | | | | | | | | | | |

( 2 ) INFORMATION FOR SEQ ID NO:3:

( i ) SEQUENCE CHARACTERISTICS:
        ( A ) LENGTH: 1299 base pairs
        ( B ) TYPE: nucleic acid
        ( C ) STRANDEDNESS: both
        ( D ) TOPOLOGY: linear ( i i ) MOLECULE TYPE: cDNA ( x i ) SEQUENCE DESCRIPTION: SEQ ID NO:3:

| | | | | | |
|---|---|---|---|---|---|
| TGCAGGTACC | ATGGAGCTGA | GCTATAGGCT | CTTCATCTGC | CTCCTGCTCT | GGGGTAGTAC | 60 |
| TGAGCTGTGC | TACCCCCAAC | CCCTCTGGCT | CTTGCAGGGT | GGAGCCAGCC | ATCCTGAGAC | 120 |
| GTCCGTACAG | CCCGTACTGG | TGGAGTGTCA | GGAGGCCACT | CTGATGGTCA | TGGTCAGCAA | 180 |
| AGACCTTTTT | GGCACCGGGA | AGCTCATCAG | GGCTGCTGAC | CTCACCTTGG | GCCCAGAGGC | 240 |
| CTGTGAGCCT | CTGGTCTCCA | TGGACACAGA | AGATGTGGTC | AGGTTTGAGG | TTGGACTCCA | 300 |
| CGAGTGTGGC | AACAGCATGC | AGGTAACTGA | CGATGCCCTG | GTGTACAGCA | CCTTCCTGCT | 360 |
| CCATGACCCC | CGCCCCGTGG | GAAACCTGTC | CATCGTGAGG | ACTAACCGCG | CAGAGATTCC | 420 |
| CATCGAGTGC | CGCTACCCCA | GGCAGGGCAA | TGTGAGCAGC | CAGGCCATCC | TGCCCACCTG | 480 |
| GTTGCCCTTC | AGGACCACGG | TGTTCTCAGA | GGAGAAGCTG | ACTTTCTCTC | TGCGTCTGAT | 540 |
| GGAGGAGAAC | TGGAACGCTG | AGAAGAGGTC | CCCCACCTTC | CACCTGGGAG | ATGCAGCCCA | 600 |
| CCTCCAGGCA | GAAATCCACA | CTGGCAGCCA | CGTGCCACTG | CGGTTGTTTG | TGGACCACTG | 660 |
| CGTGGCCACA | CCGACACCAG | ACCAGAATGC | CTCCCCTTAT | CACACCATCG | TGGACTTCCA | 720 |
| TGGCTGTCTT | GTCGACGGTC | TCACTGATGC | CTCTTCTGCA | TTCAAAGTTC | CTCGACCCGG | 780 |
| GCCAGATACA | CTCCAGTTCA | CAGTGGATGT | CTTCCACTTT | GCTAATGACT | CCAGAAACAT | 840 |
| GATATACATC | ACCTGCCACC | TGAAGGTCAC | CCTAGCTGAG | CAGGACCCAG | ATGAACTCAA | 900 |
| CAAGGCCTGT | TCCTTCAGCA | AGCCTTCCAA | CAGCTGGTTC | CCAGTGGAAG | CCCGGCTGA | 960 |
| CATCTGTCAA | TGCTGTAACA | AAGGTGACTG | TGGCACTCCA | AGCCATTCCA | GGAGGCAGCC | 1020 |
| TCATGTCATG | AGCCAGTGGT | CCAGGTCTGC | TTCCCGTAAC | CGCAGGCATG | TGACAGAAGA | 1080 |
| AGCAGATGTC | ACCGTGGGGC | CACTGATCTT | CCTGGACAGG | AGGGGTGACC | ATGAAGTAGA | 1140 |
| GCAGTGGGCT | TTGCCTTCTG | ACACCTCAGT | GGTGCTGCTG | GGCGTAGGCC | TGGCTGTGGT | 1200 |
| GGTGTCCCTG | ACTCTGACTG | CTGTTATCCT | GGTTCTCACC | AGGAGGTGTC | GCACTGCCTC | 1260 |
| CCACCCTGTG | TCTGCTTCCG | AATAAAAGAA | GAAAGCAAT | | | 1299 |

( 2 ) INFORMATION FOR SEQ ID NO:4:

( i ) SEQUENCE CHARACTERISTICS:
  ( A ) LENGTH: 424 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:4:

```
Met Glu Leu Ser Tyr Arg Leu Phe Ile Cys Leu Leu Leu Trp Gly Ser
1               5                   10                  15

Thr Glu Leu Cys Tyr Pro Gln Pro Leu Trp Leu Leu Gln Gly Gly Ala
            20                  25                  30

Ser His Pro Glu Thr Ser Val Gln Pro Val Leu Val Glu Cys Gln Glu
        35                  40                  45

Ala Thr Leu Met Val Met Val Ser Lys Asp Leu Phe Gly Thr Gly Lys
    50                  55                  60

Leu Ile Arg Ala Ala Asp Leu Thr Leu Gly Pro Glu Ala Cys Glu Pro
65                  70                  75                  80

Leu Val Ser Met Asp Thr Glu Asp Val Val Arg Phe Glu Val Gly Leu
            85                  90                  95

His Glu Cys Gly Asn Ser Met Gln Val Thr Asp Asp Ala Leu Val Tyr
        100                 105                 110
```

```
Ser  Thr  Phe  Leu  Leu  His  Asp  Pro  Arg  Pro  Val  Gly  Asn  Leu  Ser  Ile
          115                 120                           125

Val  Arg  Thr  Asn  Arg  Ala  Glu  Ile  Pro  Ile  Glu  Cys  Arg  Tyr  Pro  Arg
          130                 135                 140

Gln  Gly  Asn  Val  Ser  Ser  Gln  Ala  Ile  Leu  Pro  Thr  Trp  Leu  Pro  Phe
145                      150                      155                      160

Arg  Thr  Thr  Val  Phe  Ser  Glu  Glu  Lys  Leu  Thr  Phe  Ser  Leu  Arg  Leu
                    165                 170                      175

Met  Glu  Glu  Asn  Trp  Asn  Ala  Glu  Lys  Arg  Ser  Pro  Thr  Phe  His  Leu
               180                 185                           190

Gly  Asp  Ala  Ala  His  Leu  Gln  Ala  Glu  Ile  His  Thr  Gly  Ser  His  Val
          195                 200                           205

Pro  Leu  Arg  Leu  Phe  Val  Asp  His  Cys  Val  Ala  Thr  Pro  Thr  Pro  Asp
     210                      215                      220

Gln  Asn  Ala  Ser  Pro  Tyr  His  Thr  Ile  Val  Asp  Phe  His  Gly  Cys  Leu
225                      230                      235                      240

Val  Asp  Gly  Leu  Thr  Asp  Ala  Ser  Ser  Ala  Phe  Lys  Val  Pro  Arg  Pro
               245                      250                      255

Gly  Pro  Asp  Thr  Leu  Gln  Phe  Thr  Val  Asp  Val  Phe  His  Phe  Ala  Asn
               260                      265                      270

Asp  Ser  Arg  Asn  Met  Ile  Tyr  Ile  Thr  Cys  His  Leu  Lys  Val  Thr  Leu
          275                 280                           285

Ala  Glu  Gln  Asp  Pro  Asp  Glu  Leu  Asn  Lys  Ala  Cys  Ser  Phe  Ser  Lys
     290                      295                      300

Pro  Ser  Asn  Ser  Trp  Phe  Pro  Val  Glu  Gly  Pro  Ala  Asp  Ile  Cys  Gln
305                      310                      315                      320

Cys  Cys  Asn  Lys  Gly  Asp  Cys  Gly  Thr  Pro  Ser  His  Ser  Arg  Arg  Gln
                    325                 330                           335

Pro  His  Val  Met  Ser  Gln  Trp  Ser  Arg  Ser  Ala  Ser  Arg  Asn  Arg  Arg
               340                 345                           350

His  Val  Thr  Glu  Glu  Ala  Asp  Val  Thr  Val  Gly  Pro  Leu  Ile  Phe  Leu
          355                 360                           365

Asp  Arg  Arg  Gly  Asp  His  Glu  Val  Glu  Gln  Trp  Ala  Leu  Pro  Ser  Asp
     370                      375                      380

Thr  Ser  Val  Val  Leu  Leu  Gly  Val  Gly  Leu  Ala  Val  Val  Val  Ser  Leu
385                      390                      395                      400

Thr  Leu  Thr  Ala  Val  Ile  Leu  Val  Leu  Thr  Arg  Arg  Cys  Arg  Thr  Ala
               405                      410                      415

Ser  His  Pro  Val  Ser  Ala  Ser  Glu
               420
```

( 2 ) INFORMATION FOR SEQ ID NO:5:

( i ) SEQUENCE CHARACTERISTICS:
        ( A ) LENGTH: 424 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

```
Met  Ala  Ser  Ser  Tyr  Phe  Leu  Phe  Leu  Cys  Leu  Leu  Leu  Cys  Gly  Gly
1                   5                   10                          15

Pro  Glu  Leu  Cys  Asn  Ser  Gln  Thr  Leu  Trp  Leu  Leu  Pro  Gly  Gly  Thr
               20                      25                      30
```

```
Pro  Thr  Pro  Val  Gly  Ser  Ser  Pro  Val  Lys  Val  Glu  Cys  Leu  Glu
     35                       40                  45

Ala  Glu  Leu  Val  Val  Thr  Val  Ser  Arg  Asp  Leu  Phe  Gly  Thr  Gly  Lys
50                            55                       60

Leu  Val  Gln  Pro  Gly  Asp  Leu  Thr  Leu  Gly  Ser  Glu  Gly  Cys  Gln  Pro
65                       70                  75                            80

Arg  Val  Ser  Val  Asp  Thr  Asp  Val  Val  Arg  Phe  Asn  Ala  Gln  Leu  His
                    85                       90                            95

Glu  Cys  Ser  Ser  Arg  Val  Gln  Met  Thr  Lys  Asp  Ala  Leu  Val  Tyr  Ser
               100                      105                  110

Thr  Phe  Leu  Leu  His  Asp  Pro  Arg  Pro  Val  Ser  Gly  Leu  Ser  Ile  Leu
          115                      120                       125

Arg  Thr  Asn  Arg  Val  Glu  Val  Pro  Ile  Glu  Cys  Arg  Tyr  Pro  Arg  Gln
     130                      135                       140

Gly  Asn  Val  Ser  Ser  His  Pro  Ile  Gln  Pro  Thr  Trp  Val  Pro  Phe  Arg
145                           150                      155                      160

Ala  Thr  Val  Ser  Ser  Glu  Glu  Lys  Leu  Ala  Phe  Ser  Leu  Arg  Leu  Met
                    165                      170                           175

Glu  Glu  Asn  Trp  Asn  Thr  Glu  Lys  Ser  Ala  Pro  Thr  Phe  His  Leu  Gly
               180                      185                           190

Glu  Val  Ala  His  Leu  Gln  Ala  Glu  Val  Gln  Thr  Gly  Ser  His  Leu  Pro
               195                      200                      205

Leu  Gln  Leu  Phe  Val  Asp  His  Cys  Val  Ala  Thr  Pro  Ser  Pro  Leu  Pro
     210                      215                       220

Asp  Pro  Asn  Ser  Ser  Pro  Tyr  His  Phe  Ile  Val  Asp  Phe  His  Gly  Cys
225                           230                      235                      240

Leu  Val  Asp  Gly  Leu  Ser  Glu  Ser  Phe  Ser  Ala  Phe  Gln  Val  Pro  Arg
               245                      250                           255

Pro  Arg  Pro  Glu  Thr  Leu  Gln  Phe  Thr  Val  Asp  Val  Phe  His  Phe  Ala
               260                      265                           270

Asn  Ser  Ser  Arg  Asn  Thr  Leu  Tyr  Ile  Thr  Cys  His  Leu  Lys  Val  Ala
          275                      280                       285

Pro  Ala  Asn  Gln  Ile  Pro  Asp  Lys  Leu  Asn  Lys  Ala  Cys  Ser  Phe  Asn
290                           295                      300

Lys  Thr  Ser  Gln  Ser  Trp  Leu  Pro  Val  Glu  Gly  Asp  Ala  Asp  Ile  Cys
305                           310                      315                      320

Asp  Cys  Cys  Ser  His  Gly  Asn  Cys  Ser  Asn  Ser  Ser  Ser  Ser  Gln  Phe
                    325                      330                           335

Gln  Ile  His  Gly  Pro  Arg  Gln  Trp  Ser  Lys  Leu  Val  Ser  Arg  Asn  Arg
               340                      345                      350

Arg  His  Val  Thr  Asp  Glu  Ala  Asp  Val  Thr  Val  Gly  Pro  Leu  Ile  Phe
          355                      360                      365

Leu  Gly  Lys  Ala  Asn  Asp  Gln  Thr  Val  Glu  Gly  Trp  Thr  Ala  Ser  Ala
     370                      375                      380

Gln  Thr  Ser  Val  Ala  Leu  Gly  Leu  Gly  Leu  Ala  Thr  Val  Ala  Phe  Leu
385                           390                      395                      400

Thr  Leu  Ala  Ala  Ile  Val  Leu  Ala  Val  Thr  Arg  Lys  Cys  His  Ser  Ser
                    405                      410                           415

Ser  Tyr  Leu  Val  Ser  Leu  Pro  Gln
               420
```

(2) INFORMATION FOR SEQ ID NO:6:

(i) SEQUENCE CHARACTERISTICS:
(A) LENGTH: 2201 base pairs (B) TYPE: nucleic acid
(C) STRANDEDNESS: both
(D) TOPOLOGY: linear (ii) MOLECULE TYPE: cDNA (xi) SEQUENCE DESCRIPTION: SEQ ID NO:6:

| | | | | | | |
|---|---|---|---|---|---|---|
| CACCTCGGCG | CTTTGGTGGT | ACCTTCCAAC | ATGGCGAGGT | GGCAGAGGAA | AGCATCTGTA | 60 |
| AGCTCTCCGT | GCGGCAGGAG | CATCTACAGG | TTTCTTTCCC | TCTTATTCAC | CCTTGTGACT | 120 |
| TCAGTGAACT | CAGTAAGCCT | TCCTCAGTCC | GAGAATCCTG | CCTTCCCAGG | CACTCTCATT | 180 |
| TGTGACAAAG | ACGAAGTGAG | AATTGAATTT | TCAAGCAGAT | TGACATGGA | AAAATGGAAT | 240 |
| CCTTCTGTGG | TGGATACCCT | TGGTAGTGAA | ATTTTGAACT | GCACTTATGC | TCTGGACTTG | 300 |
| GAAAGGTTCG | TCCTGAAGTT | CCCTTACGAG | ACCTGCACTA | TAAAAGTGGT | TGGTGGATAC | 360 |
| CAGGTGAACA | TCAGAGTGGG | GGACACCACC | ACTGATGTGA | GATATAAAGA | TGACATGTAT | 420 |
| CATTTCTTCT | GTCCAGCTAT | TCAAGCAGAG | ACCCATGAGA | TTTCAGAAAT | TGTTGTCTGC | 480 |
| AGGAGAGATC | TAATATCTTT | TTCTTTCCCA | CAACTTTTCT | CTAGGCTTGC | TGATGAAAAC | 540 |
| CAGAATGTAT | CTGAGATGGG | ATGGATTGTT | AAGATTGGCA | ATGGTACAAG | AGCCCACATT | 600 |
| CTGCCCTTGA | AGGATGCCAT | AGTACAAGGA | TTTAATCTTC | TGATTGACAG | CCAGAAAGTG | 660 |
| ACTCTCCACG | TGCCAGCCAA | TGCTACTGGA | ATAGTTCACT | ATGTGCAAGA | GAGCAGCTAT | 720 |
| CTCTATACTG | TGCAGCTGGA | GCTCTTGTTC | TCAACCACTG | GGCAGAAGAT | CGTCTTCTCA | 780 |
| TCACACGCTA | TCTGCGCACC | AGATCTTTCT | GTGGCTTGTA | ATGCTACACA | CATGACTCTC | 840 |
| ACTATACCAG | AATTTCCTGG | GAAGCTAGAG | TCTGTGGACT | TTGGACAATG | GAGCATCCT | 900 |
| GAGGACCAAT | GGCATGCCAA | TGGAATTGAC | AAAGAAGCAA | CAAATGGCTT | GAGATTGAAT | 960 |
| TTCAGAAAAT | CTCTCCTGAA | AACTAAACCC | TCTGAAAAAT | GTCCATTCTA | CCAGTTCTAC | 1020 |
| CTCTCTTCAC | TCAAGCTGAC | CTTCTACTTC | CAAGGGAACA | TGCTATCCAC | AGTGATAGAT | 1080 |
| CCTGAGTGCC | ACTGTGAGTC | ACCAGTCTCT | ATAGATGAAC | TGTGTGCACA | GGATGGGTTT | 1140 |
| ATGGACTTTG | AGGTCTACAG | CCACCAAACA | AAACCCGCAC | TGAACCTGGA | CACCCTCCTG | 1200 |
| GTGGGAAATT | CCTCTTGCCA | GCCTATTTTC | AAGGTGCAGT | CTGTGGGGCT | TGCAAGGTTT | 1260 |
| CACATACCTC | TGAATGGATG | TGGAACAAGG | CAGAAATTTG | AAGGTGATAA | AGTCATCTAT | 1320 |
| GAGAATGAAA | TACATGCTCT | CTGGGAAAAC | CCACCCTCCA | ACATTGTATT | CAGAAACAGC | 1380 |
| GAGTTCAGGA | TGACAGTAAG | ATGCTATTAC | ATCAGAGACA | GTATGCTACT | AAATGCCCAT | 1440 |
| GTCAAAGGAC | ATCCTTCTCC | AGAGGCCTTT | GTAAAGCCAG | GCCCACTGGT | GTTGGTCCTA | 1500 |
| CAAACATACC | CAGACCAATC | CTACCAACGG | CCTTACAGGA | AGGATGAGTA | CCCTCTAGTG | 1560 |
| AGGTACCTCC | GCCAGCCAAT | CTACATGGAA | GTGAAGGTCT | TGAGCAGGAA | CGATCCCAAC | 1620 |
| ATCAAGCTGG | TCTTAGATGA | CTGCTGGGCA | ACTTCTTCTG | AGGACCCGGC | TCTGCGCCT | 1680 |
| CAGTGGCAGA | TTGTCATGGA | TGGCTGTGAA | TATGAACTGG | ACAACTACCG | CACTACTTTC | 1740 |
| CACCCAGCTG | GCTCCTCTGC | AGCCCATTCC | GGTCACTACC | AGAGGTTTGA | TGTGAAGACT | 1800 |
| TTTGCCTTTG | TATCAGAGGC | ACGGGGCTC | TCCAGCCTGA | TCTACTTCCA | CTGCAGTGCC | 1860 |
| TTGATCTGTA | ACCAAGTCTC | TCTTGACTCC | CCTCTGTGCT | CTGTGACTTG | CCCTGCATCA | 1920 |
| CTGAGGAGCA | AACGAGAGGC | CAACAAAGAA | GACACAATGA | CGGTTAGCCT | TCCAGGACCT | 1980 |
| ATTCTCTTGC | TGTCAGATGT | CTCTTCATCC | AAAGGTGTTG | ACCCCAGCAG | CTCTGAGATT | 2040 |
| ACCAAGGATA | TTATTGCCAA | GGATATTGCT | TCTAAAACAC | TGGGTGCTGT | GGCTGCACTA | 2100 |
| GTGGGCTCAG | CTGTCATTCT | AGGCTTCATC | TGTTACCTGT | ATAAGAAAAG | AACTATAAGG | 2160 |

TTCAATCACT GATTGGACTT GCAAATAAAG AGACTGCAGT C                        2201

( 2 ) INFORMATION FOR SEQ ID NO:7:

( i ) SEQUENCE CHARACTERISTICS:
        ( A ) LENGTH: 713 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

```
Met Ala Arg Trp Gln Arg Lys Ala Ser Val Ser Ser Pro Cys Gly Arg
 1               5                  10                  15
Ser Ile Tyr Arg Phe Leu Ser Leu Leu Phe Thr Leu Val Thr Ser Val
                20                  25                  30
Asn Ser Val Ser Leu Pro Gln Ser Glu Asn Pro Ala Phe Pro Gly Thr
            35                  40                  45
Leu Ile Cys Asp Lys Asp Glu Val Arg Ile Glu Phe Ser Ser Arg Phe
        50                  55                  60
Asp Met Glu Lys Trp Asn Pro Ser Val Val Asp Thr Leu Gly Ser Glu
65                  70                  75                  80
Ile Leu Asn Cys Thr Tyr Ala Leu Asp Leu Glu Arg Phe Val Leu Lys
                85                  90                  95
Phe Pro Tyr Glu Thr Cys Thr Ile Lys Val Val Gly Gly Tyr Gln Val
                100                 105                 110
Asn Ile Arg Val Gly Asp Thr Thr Asp Val Arg Tyr Lys Asp Asp
            115                 120                 125
Met Tyr His Phe Phe Cys Pro Ala Ile Gln Ala Glu Thr His Glu Ile
        130                 135                 140
Ser Glu Ile Val Val Cys Arg Arg Asp Leu Ile Ser Phe Ser Phe Pro
145                 150                 155                 160
Gln Leu Phe Ser Arg Leu Ala Asp Glu Asn Gln Asn Val Ser Glu Met
                165                 170                 175
Gly Trp Ile Val Lys Ile Gly Asn Gly Thr Arg Ala His Ile Leu Pro
                180                 185                 190
Leu Lys Asp Ala Ile Val Gln Gly Phe Asn Leu Leu Ile Asp Ser Gln
            195                 200                 205
Lys Val Thr Leu His Val Pro Ala Asn Ala Thr Gly Ile Val His Tyr
        210                 215                 220
Val Gln Glu Ser Ser Tyr Leu Tyr Thr Val Gln Leu Glu Leu Leu Phe
225                 230                 235                 240
Ser Thr Thr Gly Gln Lys Ile Val Phe Ser Ser His Ala Ile Cys Ala
                245                 250                 255
Pro Asp Leu Ser Val Ala Cys Asn Ala Thr His Met Thr Leu Thr Ile
            260                 265                 270
Pro Glu Phe Pro Gly Lys Leu Glu Ser Val Asp Phe Gly Gln Trp Ser
        275                 280                 285
Ile Pro Glu Asp Gln Trp His Ala Asn Gly Ile Asp Lys Glu Ala Thr
        290                 295                 300
Asn Gly Leu Arg Leu Asn Phe Arg Lys Ser Leu Leu Lys Thr Lys Pro
305                 310                 315                 320
Ser Glu Lys Cys Pro Phe Tyr Gln Phe Tyr Leu Ser Ser Leu Lys Leu
                325                 330                 335
Thr Phe Tyr Phe Gln Gly Asn Met Leu Ser Thr Val Ile Asp Pro Glu
                340                 345                 350
```

```
Cys His Cys Glu Ser Pro Val Ser Ile Asp Glu Leu Cys Ala Gln Asp
    355                 360                 365

Gly Phe Met Asp Phe Glu Val Tyr Ser His Gln Thr Lys Pro Ala Leu
    370                 375                 380

Asn Leu Asp Thr Leu Leu Val Gly Asn Ser Ser Cys Gln Pro Ile Phe
385                     390                 395                 400

Lys Val Gln Ser Val Gly Leu Ala Arg Phe His Ile Pro Leu Asn Gly
                405                 410                 415

Cys Gly Thr Arg Gln Lys Phe Glu Gly Asp Lys Val Ile Tyr Glu Asn
                420             425                 430

Glu Ile His Ala Leu Trp Glu Asn Pro Pro Ser Asn Ile Val Phe Arg
        435                 440                 445

Asn Ser Glu Phe Arg Met Thr Val Arg Cys Tyr Tyr Ile Arg Asp Ser
    450                 455                 460

Met Leu Leu Asn Ala His Val Lys Gly His Pro Ser Pro Glu Ala Phe
465                 470                 475                 480

Val Lys Pro Gly Pro Leu Val Leu Val Leu Gln Thr Tyr Pro Asp Gln
                485                 490                 495

Ser Tyr Gln Arg Pro Tyr Arg Lys Asp Glu Tyr Pro Leu Val Arg Tyr
            500                 505                 510

Leu Arg Gln Pro Ile Tyr Met Glu Val Lys Val Leu Ser Arg Asn Asp
        515                 520                 525

Pro Asn Ile Lys Leu Val Leu Asp Asp Cys Trp Ala Thr Ser Ser Glu
530                 535                 540

Asp Pro Ala Ser Ala Pro Gln Trp Gln Ile Val Met Asp Gly Cys Glu
545                 550                 555                 560

Tyr Glu Leu Asp Asn Tyr Arg Thr Thr Phe His Pro Ala Gly Ser Ser
                565                 570                 575

Ala Ala His Ser Gly His Tyr Gln Arg Phe Asp Val Lys Thr Phe Ala
            580                 585                 590

Phe Val Ser Glu Ala Arg Gly Leu Ser Ser Leu Ile Tyr Phe His Cys
        595                 600                 605

Ser Ala Leu Ile Cys Asn Gln Val Ser Leu Asp Ser Pro Leu Cys Ser
    610                 615                 620

Val Thr Cys Pro Ala Ser Leu Arg Ser Lys Arg Glu Ala Asn Lys Glu
625                 630                 635                 640

Asp Thr Met Thr Val Ser Leu Pro Gly Pro Ile Leu Leu Leu Ser Asp
                645                 650                 655

Val Ser Ser Ser Lys Gly Val Asp Pro Ser Ser Ser Glu Ile Thr Lys
            660                 665                 670

Asp Ile Ile Ala Lys Asp Ile Ala Ser Lys Thr Leu Gly Ala Val Ala
        675                 680                 685

Ala Leu Val Gly Ser Ala Val Ile Leu Gly Phe Ile Cys Tyr Leu Tyr
    690                 695                 700

Lys Lys Arg Thr Ile Arg Phe Asn His
705                 710
```

( 2 ) INFORMATION FOR SEQ ID NO:8:

( i ) SEQUENCE CHARACTERISTICS:
        ( A ) LENGTH: 713 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:8:

| | | | | | | | | | | | | | | |
|---|---|---|---|---|---|---|---|---|---|---|---|---|---|---|
| Met | Ala | Arg | Trp | Gln | Arg | Lys | Ala | Ser | Val | Ser | Ser | Pro | Cys | Gly | Arg |
| 1 | | | | 5 | | | | | 10 | | | | | 15 |
| Ser | Ile | Tyr | Arg | Phe | Leu | Ser | Leu | Leu | Phe | Thr | Leu | Val | Thr | Ser | Val |
| | | | 20 | | | | | 25 | | | | | 30 | | |
| Asn | Ser | Val | Ser | Leu | Pro | Gln | Ser | Glu | Asn | Pro | Ala | Phe | Pro | Gly | Thr |
| | | 35 | | | | | 40 | | | | | 45 | | | |
| Leu | Ile | Cys | Asp | Lys | Asp | Glu | Val | Arg | Ile | Glu | Phe | Ser | Ser | Arg | Phe |
| | | 50 | | | | 55 | | | | | 60 | | | | |
| Asp | Met | Glu | Lys | Trp | Asn | Pro | Ser | Val | Val | Asp | Thr | Leu | Gly | Ser | Glu |
| 65 | | | | | 70 | | | | | 75 | | | | | 80 |
| Ile | Leu | Asn | Cys | Thr | Tyr | Ala | Leu | Asp | Leu | Glu | Arg | Phe | Val | Leu | Lys |
| | | | | 85 | | | | | 90 | | | | | | 95 |
| Phe | Pro | Tyr | Glu | Thr | Cys | Thr | Ile | Lys | Val | Val | Gly | Gly | Tyr | Gln | Val |
| | | | 100 | | | | | 105 | | | | | 110 | | |
| Asn | Ile | Arg | Val | Gly | Asp | Thr | Thr | Thr | Asp | Val | Arg | Tyr | Lys | Asp | Asp |
| | | 115 | | | | | 120 | | | | | 125 | | | |
| Met | Tyr | His | Phe | Phe | Cys | Pro | Ala | Ile | Gln | Ala | Glu | Thr | His | Glu | Ile |
| 130 | | | | | 135 | | | | | 140 | | | | | |
| Ser | Glu | Ile | Val | Val | Cys | Arg | Arg | Asp | Leu | Ile | Ser | Phe | Ser | Phe | Pro |
| 145 | | | | | 150 | | | | | 155 | | | | | 160 |
| Gln | Leu | Phe | Ser | Arg | Leu | Ala | Asp | Glu | Asn | Gln | Asn | Val | Ser | Glu | Met |
| | | | | 165 | | | | | 170 | | | | | 175 | |
| Gly | Trp | Ile | Val | Lys | Ile | Gly | Asn | Gly | Thr | Arg | Ala | His | Ile | Leu | Pro |
| | | | 180 | | | | | 185 | | | | | 190 | | |
| Leu | Lys | Asp | Ala | Ile | Val | Gln | Gly | Phe | Asn | Leu | Leu | Ile | Asp | Ser | Gln |
| | | 195 | | | | | 200 | | | | | 205 | | | |
| Lys | Val | Thr | Leu | His | Val | Pro | Ala | Asn | Ala | Thr | Gly | Ile | Val | His | Tyr |
| 210 | | | | | | 215 | | | | | 220 | | | | |
| Val | Gln | Glu | Ser | Ser | Tyr | Leu | Tyr | Thr | Val | Gln | Leu | Glu | Leu | Leu | Phe |
| 225 | | | | | 230 | | | | | 235 | | | | | 240 |
| Ser | Thr | Thr | Gly | Gln | Lys | Ile | Val | Phe | Ser | Ser | His | Ala | Ile | Cys | Ala |
| | | | | 245 | | | | | 250 | | | | | 255 | |
| Pro | Asp | Leu | Ser | Val | Ala | Cys | Asn | Ala | Thr | His | Met | Thr | Leu | Thr | Ile |
| | | | 260 | | | | | 265 | | | | | 270 | | |
| Pro | Glu | Phe | Pro | Gly | Lys | Leu | Glu | Ser | Val | Asp | Phe | Gly | Gln | Trp | Ser |
| | | 275 | | | | | 280 | | | | | 285 | | | |
| Ile | Pro | Glu | Asp | Gln | Trp | His | Ala | Asn | Gly | Ile | Asp | Lys | Glu | Ala | Thr |
| | 290 | | | | | 295 | | | | | 300 | | | | |
| Asn | Gly | Leu | Arg | Leu | Asn | Phe | Arg | Lys | Ser | Leu | Leu | Lys | Thr | Lys | Pro |
| 305 | | | | | 310 | | | | | 315 | | | | | 320 |
| Ser | Glu | Lys | Cys | Pro | Phe | Tyr | Gln | Phe | Tyr | Leu | Ser | Ser | Leu | Lys | Leu |
| | | | | 325 | | | | | 330 | | | | | 335 | |
| Thr | Phe | Tyr | Phe | Gln | Gly | Asn | Met | Leu | Ser | Thr | Val | Ile | Asp | Pro | Glu |
| | | | 340 | | | | | 345 | | | | | 350 | | |
| Cys | His | Cys | Glu | Ser | Pro | Val | Ser | Ile | Asp | Glu | Leu | Cys | Ala | Gln | Asp |
| | | 355 | | | | | 360 | | | | | 365 | | | |
| Gly | Phe | Met | Asp | Phe | Glu | Val | Tyr | Ser | His | Gln | Thr | Lys | Pro | Ala | Leu |
| | | 370 | | | | | 375 | | | | | 380 | | | |
| Asn | Leu | Asp | Thr | Leu | Leu | Val | Gly | Asn | Ser | Ser | Cys | Gln | Pro | Ile | Phe |
| 385 | | | | | 390 | | | | | 395 | | | | | 400 |
| Lys | Val | Gln | Ser | Val | Gly | Leu | Ala | Arg | Phe | His | Ile | Pro | Leu | Asn | Gly |
| | | | | 405 | | | | | 410 | | | | | 415 | |

|       |     |     |     |     |     |     |     |     |     |     |     |     |     |
|-------|-----|-----|-----|-----|-----|-----|-----|-----|-----|-----|-----|-----|-----|
| Cys   | Gly | Thr | Arg | Gln | Lys | Phe | Glu | Gly | Asp | Lys | Val | Ile | Tyr | Glu | Asn |
|       |     |     | 420 |     |     |     |     | 425 |     |     |     |     | 430 |

Cys Gly Thr Arg Gln Lys Phe Glu Gly Asp Lys Val Ile Tyr Glu Asn
                420                 425                 430

Glu Ile His Ala Leu Trp Glu Asn Pro Pro Ser Asn Ile Val Phe Arg
        435             440                 445

Asn Ser Glu Phe Arg Met Thr Val Arg Cys Tyr Tyr Ile Arg Asp Ser
    450             455                 460

Met Leu Leu Asn Ala His Val Lys Gly His Pro Ser Pro Glu Ala Phe
465             470                 475                 480

Val Lys Pro Gly Pro Leu Val Leu Val Leu Gln Thr Tyr Pro Asp Gln
            485                 490                 495

Ser Tyr Gln Arg Pro Tyr Arg Lys Asp Glu Tyr Pro Leu Val Arg Tyr
        500                 505                 510

Leu Arg Gln Pro Ile Tyr Met Glu Val Lys Val Leu Ser Arg Asn Asp
        515                 520                 525

Pro Asn Ile Lys Leu Val Leu Asp Asp Cys Trp Ala Thr Ser Ser Glu
    530                 535                 540

Asp Pro Ala Ser Ala Pro Gln Trp Gln Ile Val Met Asp Gly Cys Glu
545                 550                 555                 560

Tyr Glu Leu Asp Asn Tyr Arg Thr Thr Phe His Pro Ala Gly Ser Ser
                565                 570                 575

Ala Ala His Ser Gly His Tyr Gln Arg Phe Asp Val Lys Thr Phe Ala
            580                 585                 590

Phe Val Ser Glu Ala Arg Gly Leu Ser Ser Leu Ile Tyr Phe His Cys
        595                 600                 605

Ser Ala Leu Ile Cys Asn Gln Val Ser Leu Asp Ser Pro Leu Cys Ser
    610                 615                 620

Val Thr Cys Pro Ala Ser Leu Arg Ser Lys Arg Glu Ala Asn Lys Glu
625                 630                 635                 640

Asp Thr Met Thr Val Ser Leu Pro Gly Pro Ile Leu Leu Leu Ser Asp
                645                 650                 655

Val Ser Ser Ser Lys Gly Val Asp Pro Ser Ser Ser Glu Ile Thr Lys
            660                 665                 670

Asp Ile Ile Ala Lys Asp Ile Ala Ser Lys Thr Leu Gly Ala Val Ala
        675                 680                 685

Ala Leu Val Gly Ser Ala Val Ile Leu Gly Phe Ile Cys Tyr Leu Tyr
    690                 695                 700

Lys Lys Arg Thr Ile Arg Phe Asn His
705                 710

(2) INFORMATION FOR SEQ ID NO:9:

(i) SEQUENCE CHARACTERISTICS:
        (A) LENGTH: 745 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

Met Ala Cys Arg Gln Arg Gly Gly Ser Trp Ser Pro Ser Gly Trp Phe
1               5                   10                  15

Asn Ala Gly Trp Ser Thr Tyr Arg Ser Ile Ser Leu Phe Phe Ala Leu
            20                  25                  30

Val Thr Ser Gly Asn Ser Ile Asp Val Ser Gln Leu Val Asn Pro Ala
        35                  40                  45

-continued

| | | | | | | | | | | | | | | |
|---|---|---|---|---|---|---|---|---|---|---|---|---|---|---|
| Phe | Pro | Gly | Thr | Val | Thr | Cys | Asp | Glu | Arg | Glu | Ile | Thr | Val | Glu | Phe |
| 50 | | | | | 55 | | | | | 60 | | | | |
| Pro | Ser | Ser | Pro | Gly | Thr | Lys | Lys | Trp | His | Ala | Ser | Val | Val | Asp | Pro |
| 65 | | | | 70 | | | | | 75 | | | | | 80 | |
| Leu | Gly | Leu | Asp | Met | Pro | Asn | Cys | Thr | Tyr | Ile | Leu | Asp | Pro | Glu | Lys |
| | | | | 85 | | | | | 90 | | | | | 95 | |
| Leu | Thr | Leu | Arg | Ala | Thr | Tyr | Asp | Asn | Cys | Thr | Arg | Arg | Val | His | Gly |
| | | | 100 | | | | | 105 | | | | | 110 | | |
| Gly | His | Gln | Met | Thr | Ile | Arg | Val | Met | Asn | Asn | Ser | Ala | Ala | Leu | Arg |
| | | 115 | | | | | 120 | | | | | 125 | | | |
| His | Gly | Ala | Val | Met | Tyr | Gln | Phe | Phe | Cys | Pro | Ala | Met | Gln | Val | Glu |
| | 130 | | | | | 135 | | | | | 140 | | | | |
| Glu | Thr | Gln | Gly | Leu | Ser | Ala | Ser | Thr | Ile | Cys | Gln | Lys | Asp | Phe | Met |
| 145 | | | | | 150 | | | | | 155 | | | | | 160 |
| Ser | Phe | Ser | Leu | Pro | Arg | Val | Phe | Ser | Gly | Leu | Ala | Asp | Asp | Ser | Lys |
| | | | | 165 | | | | | 170 | | | | | 175 | |
| Gly | Thr | Lys | Val | Gln | Met | Gly | Trp | Ser | Ile | Glu | Val | Gly | Asp | Gly | Ala |
| | | | 180 | | | | | 185 | | | | | 190 | | |
| Arg | Ala | Lys | Thr | Leu | Thr | Leu | Pro | Glu | Ala | Met | Lys | Glu | Gly | Phe | Ser |
| | | 195 | | | | | 200 | | | | | 205 | | | |
| Leu | Leu | Ile | Asp | Asn | His | Arg | Met | Thr | Phe | His | Val | Pro | Phe | Asn | Ala |
| | 210 | | | | | 215 | | | | | 220 | | | | |
| Thr | Gly | Val | Thr | His | Tyr | Val | Gln | Gly | Asn | Ser | His | Leu | Tyr | Met | Val |
| 225 | | | | | 230 | | | | | 235 | | | | | 240 |
| Ser | Leu | Lys | Leu | Thr | Phe | Ile | Ser | Pro | Gly | Gln | Lys | Val | Ile | Phe | Ser |
| | | | | 245 | | | | | 250 | | | | | 255 | |
| Ser | Gln | Ala | Ile | Cys | Ala | Pro | Asp | Pro | Val | Thr | Cys | Asn | Ala | Thr | His |
| | | | 260 | | | | | 265 | | | | | 270 | | |
| Met | Thr | Leu | Thr | Ile | Pro | Glu | Phe | Pro | Gly | Lys | Leu | Lys | Ser | Val | Ser |
| | | 275 | | | | | 280 | | | | | 285 | | | |
| Phe | Glu | Asn | Gln | Asn | Ile | Asp | Val | Ser | Gln | Leu | His | Asp | Asn | Gly | Ile |
| | 290 | | | | | 295 | | | | | 300 | | | | |
| Asp | Leu | Glu | Ala | Thr | Asn | Gly | Met | Lys | Leu | His | Phe | Ser | Lys | Thr | Leu |
| 305 | | | | | 310 | | | | | 315 | | | | | 320 |
| Leu | Lys | Thr | Lys | Leu | Ser | Glu | Lys | Cys | Leu | Leu | His | Gln | Phe | Tyr | Leu |
| | | | | 325 | | | | | 330 | | | | | 335 | |
| Ala | Ser | Leu | Lys | Leu | Thr | Phe | Leu | Leu | Arg | Pro | Glu | Thr | Val | Ser | Met |
| | | | 340 | | | | | 345 | | | | | 350 | | |
| Val | Ile | Tyr | Pro | Glu | Cys | Leu | Cys | Glu | Ser | Pro | Val | Ser | Ile | Val | Thr |
| | | | 355 | | | | | 360 | | | | | 365 | | |
| Gly | Glu | Leu | Cys | Thr | Gln | Asp | Gly | Phe | Met | Asp | Val | Glu | Val | Tyr | Ser |
| | 370 | | | | | 375 | | | | | 380 | | | | |
| Tyr | Gln | Thr | Gln | Pro | Ala | Leu | Asp | Leu | Gly | Thr | Leu | Arg | Val | Gly | Asn |
| 385 | | | | | 390 | | | | | 395 | | | | | 400 |
| Ser | Ser | Cys | Gln | Pro | Val | Phe | Glu | Ala | Gln | Ser | Gln | Gly | Leu | Val | Arg |
| | | | | 405 | | | | | 410 | | | | | 415 | |
| Phe | His | Ile | Pro | Leu | Asn | Gly | Cys | Gly | Thr | Arg | Tyr | Lys | Phe | Glu | Asp |
| | | | 420 | | | | | 425 | | | | | 430 | | |
| Asp | Lys | Val | Val | Tyr | Glu | Asn | Glu | Ile | His | Ala | Leu | Trp | Thr | Asp | Phe |
| | | 435 | | | | | 440 | | | | | 445 | | | |
| Pro | Pro | Ser | Lys | Ile | Ser | Arg | Asp | Ser | Glu | Phe | Arg | Met | Thr | Val | Lys |
| | 450 | | | | | 455 | | | | | 460 | | | | |
| Cys | Ser | Tyr | Ser | Arg | Asn | Asp | Met | Leu | Leu | Asn | Ile | Asn | Val | Glu | Ser |
| 465 | | | | | 470 | | | | | 475 | | | | | 480 |

| | | | | | | | | | | | | | | |
|---|---|---|---|---|---|---|---|---|---|---|---|---|---|---|
| Leu | Thr | Pro | Pro 485 | Val | Ala | Ser | Val | Lys 490 | Leu | Gly | Pro | Phe | Thr | Leu 495 | Ile |
| Leu | Gln | Ser | Tyr 500 | Pro | Asp | Asn | Ser | Gln 505 | Gln | Pro | Tyr | Gly 510 | Glu | Asn |
| Glu | Tyr | Pro 515 | Leu | Val | Arg | Phe | Leu 520 | Arg | Gln | Pro | Ile | Tyr 525 | Met | Glu | Val |
| Arg | Val 530 | Leu | Asn | Arg | Asp | Asp 535 | Pro | Asn | Ile | Lys | Leu 540 | Val | Leu | Asp | Asp |
| Cys 545 | Trp | Ala | Thr | Ser | Thr 550 | Met | Asp | Pro | Asp | Ser 555 | Phe | Pro | Gln | Trp | Asn 560 |
| Val | Val | Val | Asp | Gly 565 | Cys | Ala | Tyr | Asp | Leu 570 | Asp | Asn | Tyr | Gln | Thr 575 | Thr |
| Phe | His | Pro | Val 580 | Gly | Ser | Ser | Val | Thr 585 | His | Pro | Asp | His | Tyr 590 | Gln | Arg |
| Phe | Asp | Met 595 | Lys | Ala | Phe | Ala | Phe 600 | Val | Ser | Glu | Ala | His 605 | Val | Leu | Ser |
| Ser | Leu 610 | Val | Tyr | Phe | His | Cys 615 | Ser | Ala | Leu | Ile | Cys 620 | Asn | Arg | Leu | Ser |
| Pro 625 | Asp | Ser | Pro | Leu | Cys 630 | Ser | Val | Thr | Cys | Pro 635 | Val | Ser | Ser | Arg | His 640 |
| Arg | Arg | Ala | Thr | Gly 645 | Ala | Thr | Glu | Ala | Glu 650 | Lys | Met | Thr | Val | Ser 655 | Leu |
| Pro | Gly | Pro | Ile 660 | Leu | Leu | Leu | Ser | Asp 665 | Asp | Ser | Ser | Phe | Arg 670 | Gly | Val |
| Gly | Ser | Ser 675 | Asp | Leu | Lys | Ala | Ser 680 | Gly | Ser | Gly | Glu 685 | Lys | Ser | Arg |
| Ser | Glu 690 | Thr | Gly | Glu | Glu | Val 695 | Gly | Ser | Arg | Gly | Ala 700 | Met | Asp | Thr | Lys |
| Gly 705 | His | Lys | Thr | Ala | Gly 710 | Asp | Val | Gly | Ser | Lys 715 | Ala | Val | Ala | Ala | Val 720 |
| Ala | Ala | Phe | Ala | Gly 725 | Val | Val | Ala | Thr | Leu 730 | Gly | Phe | Ile | Tyr | Tyr 735 | Leu |
| Tyr | Glu | Lys | Arg 740 | Thr | Val | Ser | Asn | His 745 | | | | | | | |

( 2 ) INFORMATION FOR SEQ ID NO:10:

( i ) SEQUENCE CHARACTERISTICS:
        ( A ) LENGTH: 713 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:10:

| | | | | | | | | | | | | | | |
|---|---|---|---|---|---|---|---|---|---|---|---|---|---|---|
| Met 1 | Ala | Arg | Trp | Gln 5 | Arg | Lys | Ala | Ser | Val 10 | Ser | Ser | Pro | Cys | Gly 15 | Arg |
| Ser | Ile | Tyr | Arg 20 | Phe | Leu | Ser | Leu | Leu 25 | Phe | Thr | Leu | Val | Thr 30 | Ser | Val |
| Asn | Ser | Val 35 | Ser | Leu | Pro | Gln | Ser 40 | Glu | Asn | Pro | Ala | Phe 45 | Pro | Gly | Thr |
| Leu | Ile 50 | Cys | Asp | Lys | Asp | Glu 55 | Val | Arg | Ile | Glu | Phe 60 | Ser | Ser | Arg | Phe |
| Asp 65 | Met | Glu | Lys | Trp | Asn 70 | Pro | Ser | Val | Val | Asp 75 | Thr | Leu | Gly | Ser | Glu 80 |

```
Ile Leu Asn Cys Thr Tyr Ala Leu Asp Leu Glu Arg Phe Val Leu Lys
            85                  90                      95

Phe Pro Tyr Glu Thr Cys Thr Ile Lys Val Val Gly Gly Tyr Gln Val
            100                 105                     110

Asn Ile Arg Val Gly Asp Thr Thr Asp Val Arg Tyr Lys Asp Asp
            115                 120                     125

Met Tyr His Phe Phe Cys Pro Ala Ile Gln Ala Glu Thr His Glu Ile
130                         135                 140

Ser Glu Ile Val Val Cys Arg Arg Asp Leu Ile Ser Phe Ser Phe Pro
145                         150                 155                 160

Gln Leu Phe Ser Arg Leu Ala Asp Glu Asn Gln Asn Val Ser Glu Met
                165                 170                     175

Gly Trp Ile Val Lys Ile Gly Asn Gly Thr Arg Ala His Ile Leu Pro
                180                 185                     190

Leu Lys Asp Ala Ile Val Gln Gly Phe Asn Leu Leu Ile Asp Ser Gln
                195                 200                     205

Lys Val Thr Leu His Val Pro Ala Asn Ala Thr Gly Ile Val His Tyr
            210                 215                     220

Val Gln Glu Ser Ser Tyr Leu Tyr Thr Val Gln Leu Glu Leu Leu Phe
225                         230                 235                 240

Ser Thr Thr Gly Gln Lys Ile Val Phe Ser His Ala Ile Cys Ala
                        245                 250                 255

Pro Asp Leu Ser Val Ala Cys Asn Ala Thr His Met Thr Leu Thr Ile
            260                 265                     270

Pro Glu Phe Pro Gly Lys Leu Glu Ser Val Asp Phe Gly Gln Trp Ser
            275                 280                     285

Ile Pro Glu Asp Gln Trp His Ala Asn Gly Ile Asp Lys Glu Ala Thr
290                         295                 300

Asn Gly Leu Arg Leu Asn Phe Arg Lys Ser Leu Leu Lys Thr Lys Pro
305                         310                 315                 320

Ser Glu Lys Cys Pro Phe Tyr Gln Phe Tyr Leu Ser Ser Leu Lys Leu
                        325                 330                     335

Thr Phe Tyr Phe Gln Gly Asn Met Leu Ser Thr Val Ile Asp Pro Glu
                340                 345                     350

Cys His Cys Glu Ser Pro Val Ser Ile Asp Glu Leu Cys Ala Gln Asp
            355                 360                     365

Gly Phe Met Asp Phe Glu Val Tyr Ser His Gln Thr Lys Pro Ala Leu
            370                 375                     380

Asn Leu Asp Thr Leu Leu Val Gly Asn Ser Ser Cys Gln Pro Ile Phe
385                         390                 395                 400

Lys Val Gln Ser Val Gly Leu Ala Arg Phe His Ile Pro Leu Asn Gly
                405                 410                     415

Cys Gly Thr Arg Gln Lys Phe Glu Gly Asp Lys Val Ile Tyr Glu Asn
            420                 425                     430

Glu Ile His Ala Leu Trp Glu Asn Pro Pro Ser Asn Ile Val Phe Arg
            435                 440                     445

Asn Ser Glu Phe Arg Met Thr Val Arg Cys Tyr Tyr Ile Arg Asp Ser
450                         455                 460

Met Leu Leu Asn Ala His Val Lys Gly His Pro Ser Pro Glu Ala Phe
465                         470                 475                 480

Val Lys Pro Gly Pro Leu Val Leu Val Leu Gln Thr Tyr Pro Asp Gln
                        485                 490                     495

Ser Tyr Gln Arg Pro Tyr Arg Lys Asp Glu Tyr Pro Leu Val Arg Tyr
                        500                 505                     510
```

```
Leu Arg Gln Pro Ile Tyr Met Glu Val Lys Val Leu Ser Arg Asn Asp
        515             520             525

Pro Asn Ile Lys Leu Val Leu Asp Asp Cys Trp Ala Thr Ser Ser Glu
530             535             540

Asp Pro Ala Ser Ala Pro Gln Trp Gln Ile Val Met Asp Gly Cys Glu
545             550             555             560

Tyr Glu Leu Asp Asn Tyr Arg Thr Thr Phe His Pro Ala Gly Ser Ser
                565             570             575

Ala Ala His Ser Gly His Tyr Gln Arg Phe Asp Val Lys Thr Phe Ala
            580             585             590

Phe Val Ser Glu Ala Arg Gly Leu Ser Ser Leu Ile Tyr Phe His Cys
        595             600             605

Ser Ala Leu Ile Cys Asn Gln Val Ser Leu Asp Ser Pro Leu Cys Ser
    610             615             620

Val Thr Cys Pro Ala Ser Leu Arg Ser Lys Arg Glu Ala Asn Lys Glu
625             630             635             640

Asp Thr Met Thr Val Ser Leu Pro Gly Pro Ile Leu Leu Leu Ser Asp
            645             650             655

Val Ser Ser Ser Lys Gly Val Asp Pro Ser Ser Ser Glu Ile Thr Lys
        660             665             670

Asp Ile Ile Ala Lys Asp Ile Ala Ser Lys Thr Leu Gly Ala Val Ala
        675             680             685

Ala Leu Val Gly Ser Ala Val Ile Leu Gly Phe Ile Cys Tyr Leu Tyr
    690             695             700

Lys Lys Arg Thr Ile Arg Phe Asn His
705             710
```

(2) INFORMATION FOR SEQ ID NO:11:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Cys Ser Asn Ser Ser Ser Ser Gln Phe Gln Ile His Gly Pro Arg Gln
1               5               10              15
```

(2) INFORMATION FOR SEQ ID NO:12:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

```
Ile Arg Val Gly Asp Thr Thr Thr Asp Val Arg Tyr Lys Asp Asp Met
1               5               10              15
```

(2) INFORMATION FOR SEQ ID NO:13:

(i) SEQUENCE CHARACTERISTICS:
        (A) LENGTH: 16 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:13:

```
Cys Gly Thr Pro Ser His Ser Arg Arg Gln Pro His Val Met Ser Gln
 1               5                  10                  15
```

(2) INFORMATION FOR SEQ ID NO:14:

(i) SEQUENCE CHARACTERISTICS:
      (A) LENGTH: 16 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:14:

```
Ile Arg Val Met Asn Asn Ser Ala Ala Leu Arg His Gly Ala Val Met
 1               5                  10                  15
```